(12) United States Patent
King et al.

(10) Patent No.: US 9,421,266 B2
(45) Date of Patent: Aug. 23, 2016

(54) SAFETY OF PSEUDOEPHEDRINE DRUG PRODUCTS

(71) Applicants: Clifford Riley King, Hendersonville, NC (US); David William Bristol, Mills River, NC (US); Michael L. English, Pisgah Forest, NC (US)

(72) Inventors: Clifford Riley King, Hendersonville, NC (US); David William Bristol, Mills River, NC (US); Michael L. English, Pisgah Forest, NC (US)

(73) Assignee: Pisgah Laboratories, Inc., Pisgah Forest, NC (US)

( * ) Notice: Subject to any disclaimer, the term of this patent is extended or adjusted under 35 U.S.C. 154(b) by 0 days.

(21) Appl. No.: 13/723,370

(22) Filed: Dec. 21, 2012

(65) Prior Publication Data

US 2014/0178480 A1    Jun. 26, 2014

Related U.S. Application Data

(60) Continuation-in-part of application No. 13/313,870, filed on Dec. 7, 2011, and a division of application No. 11/973,252, filed on Oct. 5, 2007, and a continuation-in-part of application No. 12/537,664, filed on Aug. 7, 2009, now abandoned, which is a division of application No. 11/973,252, filed on Oct. 5, 2007.

(51) Int. Cl.

| *A61K 31/137* | (2006.01) |
|---|---|
| *A61K 47/22* | (2006.01) |
| *A61K 47/26* | (2006.01) |
| *A61K 9/00* | (2006.01) |
| *A61K 9/20* | (2006.01) |

(52) U.S. Cl.
CPC ............... *A61K 47/22* (2013.01); *A61K 31/137* (2013.01); *A61K 47/26* (2013.01); *A61K 9/0095* (2013.01); *A61K 9/2013* (2013.01)

(58) Field of Classification Search
CPC .. A16K 31/137; A16K 9/0095; A16K 9/2013
See application file for complete search history.

(56) References Cited

U.S. PATENT DOCUMENTS

| 2,925,417 | A | 2/1960 | Elslager et al. |
|---|---|---|---|
| 3,502,661 | A | 3/1970 | Kasubick et al. |
| 4,622,244 | A | 11/1986 | Lapka et al. |
| 5,225,205 | A | 7/1993 | Orsolini |
| 5,225,267 | A * | 7/1993 | Ochi ..................... B32B 15/08 428/214 |
| 5,232,919 | A | 8/1993 | Scheffler et al. |
| 5,271,946 | A | 12/1993 | Hettche |
| 5,439,688 | A | 8/1995 | Orsolini et al. |
| 5,445,832 | A | 8/1995 | Orsolini et al. |
| 5,776,885 | A | 7/1998 | Orsolini et al. |
| 5,916,590 | A * | 6/1999 | Cody et al. ................ 424/452 |
| 6,203,813 | B1 | 3/2001 | Gooberman |
| 6,673,856 | B1 * | 1/2004 | Mentink ..................... 524/110 |
| 7,105,486 | B2 | 9/2006 | Mickle et al. |
| 2004/0058946 | A1 | 3/2004 | Buchwald et al. |
| 2004/0131552 | A1 | 7/2004 | Boehm |
| 2004/0141966 | A1 * | 7/2004 | Lasky .................. C07K 14/705 424/144.1 |
| 2005/0158382 | A1 | 7/2005 | Cruz et al. |
| 2005/0176645 | A1 | 8/2005 | Mickle et al. |
| 2005/0266070 | A1 | 12/2005 | Mickle |
| 2006/0051298 | A1 | 3/2006 | Groenewoud |
| 2006/0104909 | A1 | 5/2006 | Vaghefi et al. |
| 2007/0246685 | A1 * | 10/2007 | Wyart .................... C07H 15/18 252/182.12 |

FOREIGN PATENT DOCUMENTS

| EP | 0137600 | 7/1994 |
|---|---|---|
| FR | 1461407 | 12/1966 |
| GB | 295656 | 11/1929 |

OTHER PUBLICATIONS

Hamlin, William E.; Northam, Jack I.; and Wagner, John G.—"Relationship Between in Vitro Dissolution Rates and Solubilities of Numerous Compounds Representative of Various Chemical Species", Mar. 31, 1965.
Kilometer. "The Complete Blog for the Preparation of Pharmaceutical Salts". http://www.ustc8312.com/drugnews/messages/209.html, Mar. 2008.
Stedman's Medical Dictionary, 27$^{th}$ ed. Lippincott, Williams & Wilkins, Baltimore, 2000.
Berge SM, Bighley LD, and Monkhouse DC, "Pharmaceutical Salts", Journal of Pharmaceutical Sciences, Jan. 1977, 66(1), 1-19.
Morisette SL, Almarsson O, Peterson ML, Remenar JF, Read MF, Lemmo AV, Ellis S, Cima MJ, Gardner CR, High-throughput crystallization: polymorphs, salts, co-crystals and solvates of pharmaceutical solids. Adv Drug Deliv Rev. Feb. 23, 2004;56(3):275-300.
Grant & Hackh's; Chemical Dictionary: Fifth Edition, completely revised and edited by Roger Grant and Claire Grant; McGraw-Hill Book Company; pp. 258 and 145: copyright © 1987 by McGraw-Hill, Inc.

\* cited by examiner

*Primary Examiner* — Ali Soroush
(74) *Attorney, Agent, or Firm* — Joseph T. Guy; Perkins Law Firm, LLC

(57) ABSTRACT

Drug substances comprising a amine containing pharmaceutically active compound, and at least one of an alditol acetal and an aromatic organic acid as an addition salt or an additive.

48 Claims, 43 Drawing Sheets

SAFETY OF PSEUDOEPHEDRINE DRUG PRODUCTS

CROSS-REFERENCE TO COPENDING APPLICATIONS

The present application is a continuation-in-part of each of U.S. patent application Ser. No. 12/080,513 filed Apr. 3, 2008 which is pending; U.S. patent application Ser. No. 12/080,514 filed Apr. 3, 2008 which is pending; U.S. patent application Ser. No. 12/080,531 filed Apr. 3, 2008 which is pending and U.S. patent application Ser. No. 13/334,842 filed Dec. 22, 2011 which is pending each of which is incorporated herein by reference. Each of U.S. patent application Ser. No. 12/080,513; U.S. patent application Ser. No. 12/080,514; U.S. patent application Ser. No. 12/080,531 and U.S. patent application Ser. No. 13/334,842 is, in turn, a divisional application of abandoned U.S. patent application Ser. No. 11/805,225 filed May 22, 2007 which is incorporated herein by reference. The present application is also a continuation-in-part of pending U.S. patent application Ser. No. 13/313,870 filed Dec. 7, 2011 which is, in-turn, a divisional application of pending U.S. patent application Ser. No. 11/973,252 filed Oct. 5, 2007 each of which is incorporated herein by reference. The present application is also a continuation-in-part of pending U.S. patent application Ser. No. 12/537,664 filed Aug. 7, 2009 which is, in-turn, a divisional application of pending U.S. patent application Ser. No. 11/973,252 filed Oct. 5, 2007 each of which is incorporated herein by reference.

BACKGROUND OF THE INVENTION

The present application is related to pharmaceutically acceptable salts of alkaloids or amine containing compounds, particularly those exhibiting stimulant, appetite suppressant, decongestion, physiological and/or psychological activity in humans. The invention embodies a platform technology for incorporating a targeted release mechanism within an organic-acid addition salt of amine-containing pharmaceutically active compounds. More specifically, many final dose drug products are formulated with active pharmaceutical ingredients (drug substances) that provide pain relief, mood alteration or modification, sense of euphoria, analgesia, sedation, or in addition, affect a psychotropic response. These drug products most often have the highest probability of abuse. As discussed herein, abuse means human use of physiologically or psychologically active compounds for purposes than otherwise intended or legally prescribed. As an example, the drug product Oxycontin® contains the drug substance oxycodone hydrochloride. The U.S. Drug Enforcement Agency (DEA) recognizes Oxycontin® as being implicated in a huge number of drug abuse cases resulting in a substantial societal impact. Beyond the human suffering emanating from drug abuse, the financial costs to society are a well-known burden shared by all citizens. The method of abuse, once the drug product is obtained (usually by illegal means), is to remove any coating on the tablet (often by lemon juice or saliva) followed by grinding the remaining portion into a powder. The powder is then inhaled into the nasal passageway (i.e. sniffed or "snorted") to impart the "high" to the abuser. Alternatively, the powder can be extracted or melted and the drug abuse performed by intravenous injection. Additional routes of administration for abusive purposes include the muscosal surfaces (ocular, nasal, pulmonary, buccal, sublingual, gingival, rectal and vaginal mucosa).

Of significant seriousness with detrimental consequences to society is the illicit production of methamphetamine ("meth"). Frequently, laboratories illegally producing meth are ill-equipped for the required synthetic transformations and as a consequence, introduce significant health risks to the laboratory operators. Serious conflagrations and fires have resulted from poorly operated laboratories and these incidents resulted in burn victims which in turn are overwhelming the resources of citizen-funded burn centers. Further, law enforcement is often exposed to hazardous chemical situations and local environmental damage occurs because of the lack of containment of toxic and/or hazardous chemicals. Key raw materials used to produce "meth" include ephedrine and pseudoephedrine which are most often found as the active ingredient in legitimate, useful cough and cold, and allergy medicines. Pseudoephedrine or ephedrine is easily extracted from these medicines by preferentially dissolving the active ingredient pseudoephedrine hydrochloride or ephedrine hydrochloride into, for example, isopropyl ("rubbing") alcohol followed by isolation and recovery by evaporation of the solvent. These beneficial products are now receiving more scrutiny and market restriction because of their illicit use to manufacture methamphetamine, "meth".

In a report dated July 2005 from the National Center on Addiction and Substance Abuse (CASA) at Columbia University and entitled "Under the Counter: The Diversion and Abuse of Controlled Prescription Drugs in the US", a recommendation was extolled for the FDA to require controlled drug manufacturers to take measures, where possible, to minimize the abuse potential of the drugs they manufacture. The suggested route for accomplishing this task was to formulate or reformulate the drug products to retain the desired therapeutic effect while preventing abuse. Also contained within the report are the disturbing data representing severe societal repercussions that in the period 1992 to 2003, drug abuse cases increased seven times faster than the increase in the US population.

Prior to the CASA report, the pharmaceutical industry recognized the severity of the drug abuse problem and innovative techniques to mitigate or control non-medical uses of drug substances and products have been published. Essentially, three mechanisms have been reported which minimize the potential for drug abuse: 1) encase within the drug product's formulation an antagonist to the drug substance, 2) chemically modify the drug substance to yield a prodrug, and 3) employ formulation techniques to yield products resistant to drug abuse.

The combination product wherein the drug substance prone to abuse is simultaneously delivered with an antagonist which is activated only under special circumstances typically employed by abusers (crushing, chewing, or dissolving) has received significant attention. Successful clinical trials were announced by the company Alpharma and reported in FDAnews Drug Pipeline Alert™ (Volume 4, No. 193, Oct. 3, 2006). The capsule formulation consists of an extended-release opioid with a sequestered core of naltrexone, an opioid antagonist. The sequestering subunit enabling this technology is described by Boehm in United States Patent Application Publication US 2004/01341552 A1, and is totally incorporated herein by reference.

Similarly, Elite Pharmaceuticals is reportedly initiating a Phase II clinical trial of its abuse resistant pain drug also employing the antagonist naltrexone hydrochloride. The report found in FDAnews Drug Pipeline Alert™ (Volume 4, No. 179, Sep. 13, 2006) states the previous Phase 1 trial confirmed the technical approach such that when the drug product was taken as intended, no antagonist was measured in the blood stream. However, if the drug product was crushed, the antagonist was released into the blood stream and the euphoria normally experience by oxycodone hydrochloride abusers was reduced.

Alternatives to the preceding agonist/antagonist approach include the preparation of prodrugs that exhibit their therapeutic value only when used for their intended purpose. Buchwald, et al. in United States Patent Application Publication (US 2004/0058946 A1), the disclosure of which is totally incorporated herein by reference, identifies modified oxycodone derivatives (prodrug) such that its physiological activity is only observed after the prodrug is converted to the drug in the mammalian gastrointestinal tract. Mickle, et al. in United States Patent Application Publication (US 2005/0266070 A1), the disclosure of which is totally incorporated herein by reference, identifies hydrocodone conjugates that release the drug substance following oral administration yet are resistant to intravenous or intranasal abuse.

Similarly, U.S. Pat. No. 7,105,486 B2 (Mickle et al.) the disclosure of which is totally incorporated herein by reference, describes the covalent attachment of L-lysine to the drug substance, amphetamine, to provide compounds and compositions exhibiting abuse-resistant properties and useful for the treatment of disorders including attention deficit hyperactivity disorder (ADHD), attention deficit disorder (ADD), narcolepsy and obesity.

In regard to formulation techniques, Vaghefi, et al. in United States Patent Application Publication (US 2006/0104909 A1), the disclosure of which is totally incorporated herein by reference, describes the creation of a matrix of discrete particles within which an active ingredient susceptible to abuse is distributed. The particles are coated with a water insoluble coating material creating the matrix from which the active ingredient is difficult to separate. The methodology provides a controlled release pharmaceutical composition having a reduced potential for abuse.

Another formulation technique is described in Unites States Patent Application Publication US 2006/0051298 A1, (Groenewoud), the disclosure of which is totally incorporated herein by reference. The abuse resistant pharmaceutical dosage consists of an active ingredient and at least one gel forming granule, and the granule possesses an outer brittle coating. Should the outer coating be crushed (for the purpose of abusing the drug), the subsequent exposure to an aqueous media creates a gel and inhibits extraction of the active ingredient.

Yet another formulation technique, but from the perspective of utilizing an agonist, is described in U.S. Pat. No. 4,622,244 (Lapka et al.), the disclosure of which is totally incorporated herein by reference. In Lapka et al. the inventors recommend the exposure of the drug substance, naltrexone pamoate, and a bioabsorbable polymer material to humidity before a microencapsulation process occurs. The equilibration in a humid environment of a hydrophobic drug and other materials impacts important effects on the nature of the microcapsule thus formed.

Similarly, in U.S. Pat. No. 6,203,813 B1 (Gooberman), the disclosure of which is totally incorporated herein by reference, the authors make reference to the controlled release of an opiate antagonist implant of naltrexone pamoate in a linear poly(ortho) ester.

The three mechanistic approaches presented above (antagonist, prodrug and formulation) attempt to address abuse potential by impacting the route of administration, or to differentiate the physiological environment in which the drug fulfills its intended purpose versus the drug's misuse. The release of the antagonist by illicit mechanical or physical manipulations effectively "neutralizes" the attempted abuse by the perpetrator. Alternatively, addiction could be treated by the implant of a slow-release of an antagonist as in Gooberman. A fundamental disadvantage to this combination drug/anti-drug technology is the presence of two drug substances in a product formulation for which an equivalent pharmacokinetic profile must fit potential users (or abusers) of the drug. There is also the added cost of the additional antagonist. As a technology, the antagonist approach does not offer a platform methodology to the many controlled substances having medicinal benefit. While the opioids as a class may have readily available antagonists (e.g naltrexone and naloxone), other controlled substances may not have effective antagonists. From a marketing and patient perspective, many perceived problems may arise particularly if the reliability or the intended effect of the drug is questioned.

In regard to the prodrug approach (for which not all abused drugs are susceptible to this approach), elegant chemistry is employed as an anti-abuse technology. In this case, release of the drug substance is controlled by physiological, enzymatic cleavage of the covalently bound protecting group attached to the drug substance. Theoretically, the drug is only released when the prodrug is in the intended environment for its absorption. Unfortunately, drug abusers and those illicitly supplying drugs for abuse understand free-basing techniques which are directly applicable to liberating a drug from its prodrug analog. Further the physiological aspects of the prodrug may alter the drug's anticipated pharmacokinetic profile and sufficient concentrations may not be available in certain patient populations to achieve the legitimate therapeutic effect.

The third mechanism employed for providing abuse-resistant drug products is through formulation techniques. Sophisticated manufacturing techniques are employed to produce products whose anti-abuse mechanism relies on forming a matrix from which the drug substance cannot easily be extracted. As with all formulated products, content uniformity becomes a dominating factor at the commercial scale. In the formulation process during commercial scale product manufacture, the assurance that each individual dose is identical is of critical importance. The matrix technology has inherent limitations for achieving content uniformity from a chemical assay perspective. In addition, the anti-abuse property must be maintained for every single dosage presentation and performance (anti-abuse) uniformity is likely challenged. Here too, encasing the drug in a matrix inherently alters the drug's pharmacokinetic profile and sufficient concentration may not be obtainable to achieve the desired therapeutic effect.

Historically, the preparation of mineral acid salts of basic drugs has been the preferred choice for imparting immediate release characteristics to drug substances. A drug substance's dissolution profile can influence its absorption characteristics, and in the case of a drug with a potential for abuse by snorting into the nasal cavity, rapid dissolution in nasal fluid would be required. Other factors influencing the absorption of the drug include the physiological pH encountered, the drug substance's morphology, the particle size and the particle size distribution. Typically, the nasal cavity pH is about 4.5 which provides for the rapid dissolution and absorption of highly soluble, mineral acid salts of drug substances.

U.S. Pat. No. 5,232,919 (Scheffler, et al.), the disclosure of which is totally incorporated herein by reference, discloses azelastine embonate and pharmaceutical formulations/compositions which contain it; the embonate salt to eliminate the bitter taste of azelastine alone. The term embonate is a synonym for pamoate.

French Patent 1,461,407 (Saias, et al.), the disclosure of which is totally incorporated herein by reference, discloses a process for the preparation of amine pamoates where the amine component includes piperazine, promethazine, papaverine, pholocodine, codeine, noracotine and chlorpheniramine.

The United Kingdom Patent Specification No. 295,656, the disclosure of which is totally incorporated herein by reference, discloses a process for the manufacture of difficulty soluble salts of organic bases and alkaloids. The disclosure further indicates the process for manufacture provides sparingly soluble and tasteless salts of organic nitrogenous basic compounds including alkaloids.

U.S. Pat. No. 3,502,661 (Kasubick, et al.), the disclosure of which is totally incorporated herein by reference, discloses a process for the preparation of variously substituted pyridinium and imidazolines along with their acid addition salts. Some examples indicate pamoate salts were prepared for select organic bases.

U.S. Pat. No. 2,925,417 (Elslager, et al.), the disclosure of which is totally incorporated herein by reference, discloses quinolinium salts of pamoic acid and a process for their manufacture.

U.S. Pat. No. 5,776,885 (Orsolini, et al.), the disclosure of which is totally incorporated herein by reference, discloses a pharmaceutical composition for the sustained and controlled release of water insoluble polypeptides whereby the therapeutically active peptide is in the form of its pamoate, tannate or stearate salt.

U.S. Pat. No. 5,445,832 (Orsolini, et al.), the disclosure of which is totally incorporated herein by reference, discloses a process for the preparation of microspheres made of a biodegradable polymeric material whereby a water soluble peptide or peptide salt is converted into a corresponding water-insoluble peptide salt selected from pamoates, stearates or palmitates of the peptide.

U.S. Pat. No. 5,439,688 (Orsolini, et al.), the disclosure of which is totally incorporated herein by reference, discloses a process for preparing a pharmaceutical composition in the form of microparticles designed for the controlled release of a drug that includes a biodegradable polymer and where the active ingredient can be selected from a group of possible salts, one being a pamoate.

U.S. Pat. No. 5,271,946 (Hettche) the disclosure of which is totally incorporated herein by reference, discloses a controlled release azelastine containing pharmaceutical composition whereby azelastine is incorporated into the formulation as its pamoate or other pharmaceutically active salt.

U.S. Pat. No. 5,225,205 (Orsolini, et al.), the disclosure of which is totally incorporated herein by reference, discloses a pharmaceutical composition in the form of microparticles; the formulation consisting of a peptide as its pamoate, tannate, stearate or palmitate salt; the formulation to provide a controlled release, pharmaceutical composition for the prolonged release of a medicamentous substance.

The illicit manufacture and consumption of methamphetamine has reached epidemic proportion in the Nation. This aspect of drug abuse has contributed to a number of society's ills beyond the detrimental effects to those people abusing the drug. Increased levels of crime are perpetrated to support the raw material supply and subsequent conversion of over-the-counter or easily obtained legitimate drug products to methamphetamine. Often, the chemical conversion, for instance, of pseudoephedrine to methamphetamine, is performed by those inexperienced or ignorant of the severe danger and potential for substantial physical harm and property damage. The news media regularly reports of dwellings used for illicit methamphetamine production catching on fire or are so severely contaminated with chemicals so as to prevent inhabitation. Often the conflagration of fire and chemical exposure injures the illicit processors to the extent they require substantial medical treatment (particularly in expensive burn centers); on other occasions, injury leads directly to death. The demand on a community's limited resources can be overwhelming—to law enforcement, fire departments, medical services and social services.

Administrative actions to suppress illicit methamphetamine production have also had negative consequences. Removing pseudoephedrine from immediate consumer access deprives legitimate use of a needed medicine to the general population. Further, the restrictions on pseudoephedrine availability may suppress some small scale "local" production, but have the effect of creating an industry for organized criminal activity. Arguably, the restriction on legitimate drug product created additional negative consequences for the consumer and the taxpayer: to the consumer, pricing has escalated on the restricted products, and to the taxpayer, the problem has been escalated to an international concern.

Drug products formulated with pseudoephedrine or ephedrine represent products serving legitimate medical needs, and as such, should be readily available to the discerning consumer without impedance—however well-intended the bureaucratic imposition to move these products to "behind-the-counter" availability. The invention described herein provides a chemical means to interrupt the reduction of pseudoephedrine, ephedrine or similar precursors and thereby prevent or restrict the formation of methamphetamine.

In spite of the long history of research directed at prohibiting the illicit use of pharmaceutical compounds the problem remains. There has yet to be a suitable solution which is widely applicable, easily implemented and applicable to a wide range of active pharmaceutical ingredients. The present invention provides a platform technology to address this long standing problem.

SUMMARY OF THE INVENTION

It is an object of the present invention to provide a method for supplying a pharmaceutical formulation which is bioavailable by an oral administration route but is bio-unavailable when illicit or abuse-intended routes of administration are attempted.

It is another object of the present invention to provide a method for supplying a pharmaceutical formulation which prohibits or impedes de-formulation to a degree sufficient to alter the manner in which the active pharmaceutical ingredient can be absorbed physiologically beyond its intended, legal, absorption route.

It is another object of the present invention to provide a pharmaceutical composition possessing anti-abuse characteristics attributable to targeted release properties.

It is another object of the present invention to provide drug substances and drug products having orthogonal dual property combinations wherein a binary differentiation is observed between the intended, or legal, and the abusive, illegal/illilcit, use of the drug substance or product. The patient receives the intended dosage when used properly, but the desired effect is not obtained if not used properly.

It is another object of the present invention to provide a method for supplying a pharmaceutical formulation where the active pharmaceutical ingredient is resistant to direct extraction techniques either into an aqueous solution or into an organic solvent.

It is another object of the present invention to inhibit and/or prevent de-formulation of a drug product by increasing the technical difficulty of isolating the active pharmaceutical ingredient from its carrier matrix such as excipients, binders and the like. This feature of the invention further decreases the economic viability of isolating the API for illicit purposes.

It is another object of the present invention to provide drug products employing the pharmaceutical salt methodology described herein whereby the potential for abuse of either the drug substance and/or the drug product is eliminated or greatly reduced when abuse is attempted via the mucosal surfaces or by injection or by illicit de-formulation to allow use via the muscosal surfaces or by injection.

It is an object of the present invention to provide organic acid addition salts of amine-containing active pharmaceutical ingredients which simultaneously provides for: a) a means to impart a chemical identifier for the active pharmaceutical ingredient (drug substance) enabling track and trace provisions of federal, state and/or local regulations governing narcotics or other controlled substances, b) the drug substance to be bio-available when used as intended but bio-unavailable when used in a non-therapeutic administration, c) interruption and/or prevention of the chemical reduction of the active pharmaceutical ingredient, and d) a compatible platform for use with formulation techniques which inhibit isolation and/or reduction of the drug substance from a formulated drug product.

It is another object of the invention to prevent preparation of methamphetamine by the chemical reduction of ephedrine or pseudoephedrine, the chemical reduction occurring by employing dissolving metal methodologies or the use of hydriodic acid/red phosphorous or iodine and phosphorous.

It is another object of the present invention to provide a means to restrict and impede the conversion of pseudoephedrine or ephedrine to methamphetamine.

It is another object of the present invention to provide an abuse deterrent feature to pseudoephedrine or ephedrine to inhibit its conversion to methamphetamine.

It is another object of the invention to provide formulation compatible drug substances of pseudoephedrine or ephedrine specific for, and assignable to a commercial distribution system.

It is another object of the invention to enable safe and efficacious administration of pseudoephedrine or ephedrine via direct-to-consumer sales of drug product and products containing pseudoephedrine.

It is another object of the present invention to provide formulations of the organic acid addition salts of pseudoephedrine or ephedrine wherein additional amounts of an organic acid or the acid's alkalai metal salt are present in the formulation.

It is another object of the present invention to provide API organic acid addition salts and formulations thereof which upon subjection to chemical reduction processes, the organic acid component of the API salt, or the addition of excess organic acid component competitively challenges the rate of the reduction of the API.

It is another object of the present invention to provide API organic acid addition salts and formulations thereof, optionally containing additional amounts of the organic acid component identical to or different to the one forming the API salt, the additional amounts present as the free acid, alkali salt or mono-alkali salt, the API and/or formulation resistant to extraction techniques to yield the API in its free base form.

It is yet another object of the invention to identify a chemical marker for forensic assessment benefit of attempts to chemically reduce pseudoephedrine or ephedrine as their pamoate salts.

Yet another feature of the invention is to provide API salts and formulations thereof which consume lithium or other active metal species employed to reduce the drug substance to another species.

It is a feature of the invention to utilize dibenzylidene sorbitol and its analogues as a functional excipient in abuse-potential drug products and thereby impart abuse-deterrent features to the drug product.

It is a feature of the invention to provide a secondary extraction and reduction inhibitor beyond that available from the drug substance organic acid addition salt, the inhibitor used as a functional excipient to hinder extraction and consume reducing agent during attempts to convert the drug substance to another pharmacologically active compound.

These and other advantages, as will be realized are provided in a drug substance with a pharmaceutically acceptable organic acid addition salt of an amine containing pharmaceutically active compound useful for the treatment of a therapeutic ailment administration and exhibiting prophylactic properties when employed in non-therapeutic administration.

Yet another embodiment is provided in a drug substance as a pharmaceutically acceptable organic acid addition salt of an amine containing pharmaceutically active compound exhibiting at least two dissolution profiles one of which provides for drug efficacy when administered in a formulated oral dosage and one which does not provide drug efficacy when administered as a non-oral dosage.

Yet another embodiment is provided in a drug substance with an organic acid addition salt of an amine containing pharmaceutically active compound used to treat a combination of two or more therapeutic ailments, at least one of which is drug abuse.

Yet another embodiment is provided in the prescribing of a drug product containing at least one drug substance as an organic acid addition salt of an amine containing API to a patient by a defined method of administration wherein the drug substance is a prophylactic in a different method of administration.

Yet another embodiment is provided in the prescribing of a drug product containing at least one drug substance comprising an organic acid addition salt of an amine containing active pharmaceutical ingredient to a patient for the purpose of treating an ailment by a specific administration mechanism wherein the drug product is rendered ineffective by a different administration mechanism.

Yet another embodiment is provided in prescribing a drug product containing at least one drug substance as an organic acid addition salt of an amine containing Drug Enforcement Administration controlled substance to a patient for the purpose of treating a legitimate ailment of the patient wherein the patient has a history of drug abuse meaning they have been clinically diagnosed as having drug abuse propensity.

Yet another embodiment is provided in prescribing a drug product containing at least one drug substance as an organic acid addition salt of an amine containing DEA controlled substance to a patient for the purpose of treating a legitimate ailment while simultaneously interrupting the potential for mental and physical addiction through the patient inadvertently or deliberately using the drug substance for other than the intended purpose.

Yet another embodiment is provided in a process for preparing organic acid addition salts of amine containing pharmaceutically active compounds comprising the steps of:

dissolving of an amine containing pharmaceutically active compound in a suitable solvent;
preparing a solution of an organic acid of Structure A

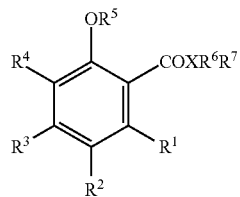

Structure A wherein $R^1$-$R^4$ are independently selected from H, alkyl of 1-6 carbons, adjacent groups may be taken together to form a cyclic alkyl or cyclic aryl moiety;
$R^5$ is selected from H, or an alkali earth cation;
$R^6$ is selected from H, alkyl of 1-6 carbons, an alkali earth cation, and aryl of 6 to 12 carbons, in a number sufficient to complete the valence bonding of X, and
wherein X is selected from nitrogen, oxygen or sulfur,
combining the solutions of amine containing pharmaceutically active compound, and the organic acid to form the reaction mixture wherein said organic acid has at least one mole of organic acid per mole of amine containing pharmaceutically active compound;
allowing said reaction mixture to react;
isolating said organic acid salt of amine containing pharmaceutically active compound by filtration, centrifugation or concentration, and
drying the isolated or purified material to remove reaction solvent.

Yet another embodiment is provided in a process for preparing the organic acid addition salts of amine-containing pharmaceutically active compound exhibiting targeted release properties comprising the steps of:
combining a pH adjusted solution of said amine-containing pharmaceutically active compound with an organic acid having at least one aromatic ring and possessing carboxyl and hydroxyl functionality in an ortho relationship or their synthetic equivalent to form a reaction solution;
cooling and precipitating solids from said reaction solution;
collecting said precipitated solid; and
drying said solids.

Yet another embodiment is provided in a process for preparing a pharmaceutically acceptable drug product exhibiting drug abuse prevention properties comprising the steps of:
selecting an organic acid addition salt of an amine containing active pharmaceutical ingredient,
combining the organic acid salt with excipients and processing aids to yield a mixture;
mixing the combined ingredients to provide blend uniformity;
sieving, screening or milling the mixture to obtain a uniform consistency; and
adding ingredients to the mixture for desired proportions of each ingredient to yield a final formulated mix.

Yet another embodiment is provided in an organic acid addition salt of amine-containing pharmaceutically active compounds wherein the organic acid comprises a compound of Formula A:

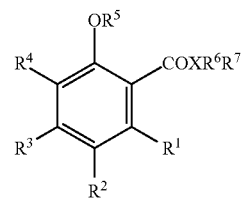

Structure A wherein $R^1$-$R^4$ are independently selected from H, alkyl of 1-6 carbons, adjacent groups may be taken together to form a cyclic alkyl or cyclic aryl moiety;
$R^5$ is selected from H, or an alkali earth cation;
$R^6$ is selected from H, alkyl of 1-6 carbons, an alkali earth cation, and aryl of 6 to 12 carbons, in a number sufficient to complete the valence bonding of X, and
wherein X is selected from nitrogen, oxygen or sulfur.

Yet another embodiment is provided in organic acid addition salts of amine-containing pharmaceutically active compounds selected for their targeted release characteristic in the gastro intestinal tract and bio-unavailability in mucosal membranes, and formulated into a drug product wherein the amine-containing pharmaceutically active compounds can not be directly isolated.

Yet another embodiment is provided in a tamper resistant oral dosage drug product comprising an organic acid salt of an amine-containing pharmaceutically active compound formulated wherein said organic acid and said amine-containing pharmaceutically active compound can not be directly isolated.

Yet another embodiment is provided in a method of administering an amine-containing pharmaceutically active compound formulation comprising:
preparing an organic acid salt of said compound;
preparing an oral dose formulation comprising said organic acid salt;
wherein upon oral digestion said compound forms a bio-available amine-containing pharmaceutically active compound; and
wherein upon use for administration via a mucosal membrane said amine-containing pharmaceutically active compound is ineffective.

Yet another embodiment is provided in a pharmaceutically active compound comprising the organic acid addition salt of an amine-containing pharmaceutically active material wherein the compound is essentially bio-unavailable when exposed to mucosal membranes and exhibits recovery from aqueous solution at pH 4.5 of at least 85 weight percent.

Yet another embodiment is provided in a pharmaceutically active compound comprising the organic acid addition salt of an amine-containing pharmaceutically active material wherein the compound is essentially bio-unavailable when exposed to human mucosal membranes and exhibits recovery from aqueous solution at pH 7.0 of at least 85 weight percent.

Yet another embodiment is provided in a pharmaceutically active compound comprising an organic acid addition salt of an amine-containing pharmaceutically active material wherein the compound is essentially bio-unavailable when exposed to mucosal membranes unless processed by the steps of:
dissolution in an aqueous solution of pH greater than 8;
extraction of the active pharmaceutical ingredient into a water immiscible solvent;

separation of the aqueous layer from the solvent;
washing of the solvent layer with an aqueous solution of pH greater than 8; and drying the solvent layer to remove traces of water.

Yet another embodiment is provided in a pharmaceutically active compound comprising an organic acid addition salt of an amine-containing pharmaceutically active material wherein the compound is essentially bio-unavailable when exposed to mucosal membranes unless processed by the steps of:

dissolution in an aqueous solution of pH greater than about 1;

filtration of the precipitated organic acid;

adjustment of the filtrate to a pH of about 8;

addition of a water immiscible solvent in which the pharmaceutically active compound is soluble;

separation of the aqueous layer from the solvent;

washing of the solvent layer with an aqueous solution of pH greater than 8; and drying the solvent layer to remove traces of water.

Yet another embodiment is provided in the use of a drug product containing at least one drug substance as an organic acid addition salt of an amine containing DEA controlled substance wherein oral administration of the drug substance provides an efficacious dosage and non-oral administration does not provide an efficacious dosage.

Yet another embodiment is provided in an oral dosage drug product comprising a pharmaceutically active compound and an alditol acetal.

Yet another embodiment is provided in a drug product. The drug product has:

a drug substance consisting of an organic acid addition salt of an active pharmaceutical wherein the active pharmaceutical is selected from the group consisting of pseudoephedrine and ephedrine and said organic acid addition salt is defined by Structure A

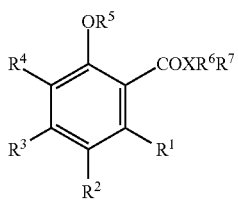

Structure A wherein $R^1$-$R^4$ are independently selected from H, alkyl of 1-6 carbons, adjacent groups may be taken together to form a cyclic alkyl, cyclic alkyl-aryl, or cyclic aryl moiety;

$R^5$ is selected from H, or an alkali earth cation;

$R^6$ and $R^7$ are independently selected from H, alkyl of 1-6 carbons, an alkali earth cation, and aryl of 6 to 12 carbons, in a number sufficient to complete the valence bonding of X, and wherein X is selected from nitrogen, oxygen or sulfur; and an additive selected from the group consisting of alditol acetal and an organic acid defined by Structure H:

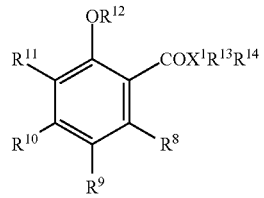

Structure H wherein $R^8$-$R^{11}$ are independently selected from H, alkyl or substituted alkyl of 1-6 carbons, adjacent groups may be taken together to form a cyclic alkyl, cyclic alkyl-aryl, or cyclic aryl moiety;

$R^{12}$ is selected from H, or an alkali earth cation;

$R^{13}$ and $R^{14}$ are independently selected from H, alkyl of 1-6 carbons, an alkali earth cation, and aryl of 6 to 12 carbons, in a number sufficient to complete the valence bonding of $X^1$; and wherein $X^1$ is selected from nitrogen, oxygen or sulfur.

Yet another embodiment is provided in a method for mitigating drug product tampering comprising:

providing a drug product comprising:

a pharmaceutically active compound having a first chemical reduction potential; an alditol actetal having a second chemical reduction potential; and an organic acid having a third chemical reduction potential wherein at least one of the second chemical reduction potential or the third chemical reduction potential is less than the first chemical reduction potential.

DETAILED DESCRIPTION

Figure 1:
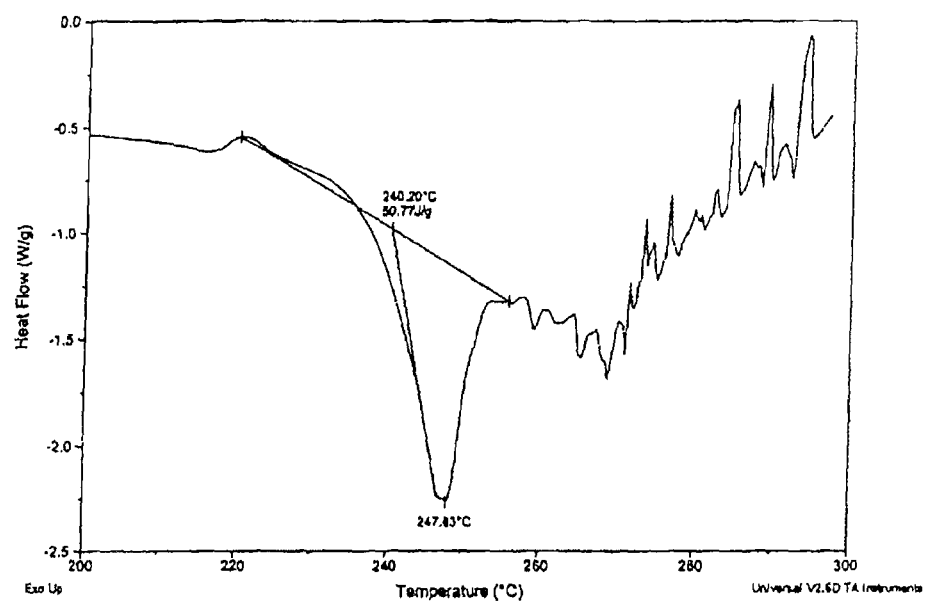
FIG. 1 is an DSC thermogram of phentermine pamoate.

The present invention is related to pseudoephedrine drug products with improved safety. More specifically, the present invention is related to pseudoephedrine or ephedrine drug products wherein illicit use, and particularly conversion to methamphetamine, is significantly thwarted through the use of alditol acetals and the additional use of organic acid addition salts as more specifically defined herein.

The invention disclosed herein provides an entirely new mechanism for providing abuse resistant drug substances and drug products whereby the conversion to methamphetamine and the method of inhalation, smoking, intravenous injection, and mucosal surface abuse are eliminated or reduced by forming an organic acid addition salt of the active ingredient having release properties incompatible with the normal administration routes for drug abuse and employing a targeted release mechanism and the chemical reaction limitations provided by alditol acetal and, in some embodiments, additional organic acid or their salts. This platform technology is widely applicable to amine containing alkaloid drug substances including but not limited to those drug substances categorized by the DEA as Controlled Substances. To elaborate on the invention's mode of action, but without relying on any particular theory or principle, drugs that are abused require that the active ingredient be bio-available in the mucosal membranes and particularly the ocular, nasal, pulmonary, buccal, sublingual, gingival, rectal or vaginal mucosa. In effect, a drug must first be released and have sufficient permeability in its biological environment for it to be bio-available. Therefore, by altering the dissolution profile to restrict, limit, reduce or eliminate release of the drug substance at physiological pH the potential for abuse is decreased. Simply stated, the drug cannot be abused without involved and technically sophisticated chemical transformations and isolation prior to the behavioral act of drug abuse. Simultaneously, the invention as described serves valuable and beneficial purposes in society by preventing drug abuse yet the invention retains the medicinal properties of the drug product when used for the intended purpose. The following discussion illustrates the design features for producing commercial drug substances and products. The benefits of the present invention are those described above and can be practiced while retaining the complex requirements reviewed below.

The reduction of pseudoephedrine or ephedrine with a chemical reducing agent removes the benzylic alcohol functionality within these molecules to yield methamphetamine. Similarly, the reductive removal of the N-benzyl moiety of benzphetamine provides methamphetamine. The chemical reductions of pseudoephedrine or of its diastereomer, ephedrine, are most often performed either by dissolving metal methodologies or with hydriodic acid in the presence of (red) phosphorous. These techniques are well known in the chemical literature and have been routinely employed by those intent upon the illicit manufacture of methamphetamine. Even to a chemical novice, a casual perusal of references cited in an internet search reveals the ease of obtaining recipes for the reduction of important drugs to yield methamphetamine. To cite but a few with self-explanatory titles: 1) "Synthetic Reduction in Clandestine Amphetamine and Methamphetamine Laboratories—A Review", Andrew Allen and Thomas S. Cantrell published in Forensic Science International, Vol. 42, 183-199 (1989); 2) "Methamphetamine Synthesis Via HI/Red Phosphorous Reduction of Ephedrine", Harry F. Skinner, published in Forensic Science International, Vol. 48, 128-134 (1990); 3) "Investigation of the Impurities Found in Methamphetamine Synthesized from Pseudoephedrine by Reduction with Hydriodic Acid and Red Phosphorous", K. L. Windahl, M. J. McTigue, J. R. Pearson, S. J. Pratt, J. E. Rowe and E. M.

Sear, Forensic Science International, Vol. 76, 97-114 (1995), and 4) "Reduction of Phenylephrine with Hydriodic Acid/Red Phosphorous or Iodine/Red Phosphorous: 3-Hydroxy-N-methylphenethylamine", Lisa M. Kitlinski, Amy L. Narman, Michael M. Brousseau and Harry F. Skinner, available online at the U.S. Department of Justice, Drug Enforcement Administration. This last article also cites the Combat Methamphetamine Epidemic Act of 2005 (as enacted in March 2006) which placed federal restriction on the sale of ephedrine-, pseudoephedrine-, and phenylpropanolamine-containing over-the-counter products. The restrictions included purchase limits, access restrictions, and identification/signature requirements. The authors assert the combination of the federal act and state imposed restrictions "have dramatically reduced the number of methamphetamine laboratories in some states". Indeed, this observation may be supportable by law enforcement statistics; however the abuse of methamphetamine has not surrendered to such administrative efforts and there remains a need to address the epidemic by employing scientific solutions.

One such solution is presented in U.S. Pat. No. 6,359,011 B1 [Bess, et al.] which issued on Mar. 19, 2002 and is incorporated herein in its entirety. The inventors recognized the need to address principal components necessary for interrupting conversion of pseudoephedrine to methamphetamine; these being reaction and separation inhibition. Ideally, both inhibition components could be achieved in combination to first prevent the isolation of pseudoephedrine from the formulated drug product and then to chemically interfere with pseudoephedrine's reduction to methamphetamine. The inventors achieved their goals by a formulation technique wherein pseudoephedrine hydrochloride drug substance was formulated with excipients and an aminoalkyl methacrylate co-polymer which they termed a denaturant. An attempt to extract pseudoephedrine from the formulated product leads to inclusion of the co-polymer (separation inhibition) along with the pseudoephedrine. Subsequent attempts to reduce the pseudoephedrine/co-polymer mixture are interrupted by consuming the reducing agent (reduction inhibition).

Unlike the invention disclosed by Bess, et al., the present invention does not rely on formulation techniques to achieve both reduction and separation inhibition. Disclosed by Bristol, et al. in U.S. Pat. No. 8,334,322 and incorporated by reference herein in its entirety, the inventors compared extractability differences of pseudoephedrine, ephedrine and benzphetamine (among others) as their hydrochloride salts with the extraction results of these drug substances present as their pamoate salts. The extraction studies were conducted under various pH conditions to represent reasonable conditions an intended abuser may employ. In each case the drug substance as its pamoate salt was essentially quantitatively recovered while the comparable hydrochloride salts were universally isolated as their free base and subject to (illicit) conversion to methamphetamine. Consequently, as the pamoate salt, the drug substance is not easily isolated for purposes of chemical reaction.

Should a potential abuser isolate the drug substance pamoate and subject the compound to chemical reduction, the reaction is further inhibited by the presence of the pamoate moiety which in itself, is susceptible to reduction. To the illicit drug preparer, consumption of additional, and significant quantities of reducing agent, e.g. lithium and ammonia, are likely prohibitive for any reasonable economic return.

The utility of the present invention is to provide a salt form of methamphetamine precursors, (pseudoephedrine, ephedrine, benzphetamine) which is: a) resistant to solvent extraction from a formulated, drug product matrix, b) poorly soluble as a drug substance (active pharmaceutical ingredient), c) difficult to convert and isolate the salt form back to its free base, and d) susceptible to chemical reduction only with significant and excessive amounts of reducing agent.

Three families of acid components are useful in preparing the salt form resistant to reduction. These are the pamoates, the hydroxy-naphthoic acid isomeric series (e.g. 3-hydroxy-2-naphthoic acid known as BON acid), and salicylates. An important aspect of the invention is to simultaneously satisfy chemical and physical requirements of the salt to impede the potential for drug abuse and hence the recitation above regarding solubility, extraction and isolation requirements prior to attempting a reduction. The pamoate class of salts has been disclosed as imparting abuse deterrent features to amine-containing active pharmaceutical ingredients when prepared as the pamoate salt. Now, in addition to these properties the pamoates and analogous acid salt formers are shown to interrupt the chemical reduction process needed to convert pseudoephedrine or ephedrine to methamphetamine. The synergistic combination of abuse-deterrence features enjoins conversion of these legitimate drug substances to methamphetamine.

In a laboratory setting, or in a clandestine drug lab, conversion of pseudoephedrine or ephedrine to methamphetamine would occur after isolation of the drug substance as the free base from the formulated drug product. When employing salts as described herein and disclosed by Bristol, et al., the isolation of the active ingredient as its free base or perhaps mineral acid salt has significant complications. Consequently, attempts to reduce the pseudoephedrine pamoate, or the like with a chemical reducing agent requires competitive reduction processes to occur between the pamoate moiety and the desired benzylic alcohol functionality of the active ingredient. Reduction recipes correctly employed by clandestine laboratories generally use about three equivalents of lithium metal in liquid ammonia for each equivalent of benzylic alcohol to yield the reduced product, methamphetamine. This stoichiometric relationship is dramatically altered when reduction of pseudoephedrine or ephedrine pamoate is attempted with the same procedure. Indeed, only about 5% of the potentially available methamphetamine is obtained. Complete conversion is only achieved in the presence of about twelve equivalents of lithium metal. The invention's utility is to attack the illicit conversion of pseudoephedrine and related compounds by creating an unfavorable economic condition: four times the amount of lithium metal is required to produce an equal quantity of methamphetamine originating from pseudoephedrine mineral acid salt. Indeed, all quantities of reagents increase to accommodate the stoichiometric change to the drug substance starting material when present as the pamoate salt.

A similar situation arises when pseudoephedrine pamoate reduction is attempted with hydriodic acid and red phosphorous. In this case however, the acid is consumed in converting the pamoate moiety to pamoic acid—an insoluble fine particle suspension, highly hydrated and presenting a reaction mixture that's very thick, gummy and tacky. Besides being difficult to stir, the bi-phasic reaction mixture sluggishly responds to the phosphorous catalyzed reduction (perhaps because of chelation of the phosphorous to the pamoic acid). Ultimately, reduction does occur to yield methamphetamine, but only after reaction periods at least twice as long as otherwise required when drug substance mineral acid salts are employed. Upon reaction completion, the difficult extraction process must be performed which is significantly beyond what the normal clandestine laboratory operator is accustomed.

It has now been surprisingly realized that the addition of alditol acetals inhibit abuse of drugs by inhibiting both isolation and reduction of the drug. Additional abuse protection can be achieved by employing these organic acid addition salts defined by Formula A herein, and exemplified by the pamoate salts.

Exemplary alditol acetals are selected from the group consisting of 1,3:2,4-dibenzylidene sorbitol; 1,3:2,4-bis(p-methylbenzylidene) sorbitol; 1,3:2,4-bis(p-chlorobenzylidene)sorbitol; 1,3:2,4-bis(2,4-dimethyldibenzylidene) sorbitol; 1,3:2,4-bis(p-ethylbenzylidene)sorbitol, abbreviated as EDBS; 1,3:2,4-bis(3,4-dimethyldibenzylidene)sorbitol, abbreviated as 3,4-DMDBS; 1,3:2,4-bis (3,4-diethylbenzylidene)sorbitol; 1,3:2,4-bis(3-ethyl4-methylbenzylidene)sorbitol; 1,3:2,4-bis(4-chloro-3-methylbenzylidene)sorbitol, 1,3:2,4-bis(3-chloro-4-methylbenzylidene)sorbitol, 1,3:2,4-bis(3-bromo-4-isopropylbenzylidene)sorbitol, 1,3:2,4-bis(3-bromo-4-methylbenzylidene)sorbitol, and 1,3:2,4-bis(3-bromo-4-ethylbenzylidene)sorbitol. Other compounds include monoacetal derivatives, such as, without limitation 2,4-mono(3,4-dimethylbenzylidene)sorbitol, 2,4-mono(4-fluoro-3-methylbenzylidene)sorbitol, and the like (e.g., instead of two moles of aromatic aldehyde, only one is reacted with the alditol) and tri-acetals (e.g., three moles of aromatic aldehyde to one of alditol). Furthermore, asymmetrical compounds may be produced, such as, without limitation: 1,3-O-(3,4-dichlorobenzylidene):2,4-O-(3,4-dimethylbenzylidene)sorbitol, 1,3-O-(3,4-difluorobenzylidene):2,4-O-(3,4-dimethylbenzylidene)sorbitol, 1,3-O-(3,4-dichlorobenzylidene):2,4-O-(3,4-dimethoxybenzylidene)sorbitol, 1,3-O-(3,4-dichlorobenzylidene):2,4-O-(5-indanylidene)sorbitol, 1,3-O-(4-nitrobenzylidene):2,4-O-(3,4dimethylbenzylidene) sorbitol, and 1,3-O-(4-nitrobenzylidene):2,4-O-(3,4-methylenedioxybenzylidene)sorbitol, 1,3-O-(4-fluoro-3-methylbenzylidene): 2,4-O-(3,4-dimethylbenzylidene) sorbitol, 1,3-O-(3,4-dimethylbenzylidene): 2,4-O-(4-fluoro-3-methylbenzylidene)sorbitol, 1,3-O-(4-fluoro-3-methylbenzylidene): 2,4-O-(3-fluoro-4-methyl benzylidene) sorbitol, 1,3-O-(3-fluoro-4-methylbenzylidene): 2,4-O-(4-fluoro-3-methylbenzylidene)sorbitol, 1,3-O-(4-fluoro-3-methylbenzylidene):2,4-O-(4-chlorobenzylidene)sorbitol, 1,3-O-(4-chlorobenzylidene):2,4-O-(4-fluoro-3-methylbenzylidene)sorbitol, 1,3-O-(4-chloro-3-methylbenzylidene): 2,4-O-(3-chloro-4-methylbenzylidene)sorbitol, 1,3-O-(3-chloro-4-methylbenzylidene): 2,4-O-(4-chloro-3-methylbenzylidene)sorbitol, 1,3-O-(4-fluoro-3-methylbenzylidene): 2,4-O-(5',6',7',8tetrahydro-2-napthylidene) sorbitol, 1,3-O-(5',6',7',8'-tetrahydronapthylidene): 2,4-O-fluoro-3-methylbenzylidene)sorbitol, 1,3-O-(4-Chloro-3-methylbenzylidene)-2,4-O-(5',6', 7',8'-tetrahydro-2-napthylidene)sorbitol, 1,3-O-(5',6',7',8'-tetrahydronapthylidene): 2,4-O-(4-chloro-3-methylbenzylidene)sorbitol, 1,3-O-(3-bromo-4-ethylbenzylidene): 2,4-O-(3,4-dimethylbenzylidene) sorbitol, 1,3-O-(3-bromo-4-isopropylbenzylidene): 2,4-O-(3,4-dimethylbenzylidene)sorbitol, 1,3-O-(3-bromo-4-methylbenzylidene): 2,4-O-(3,4-dimethylbenzylidene) sorbitol, 1,3-O-(4-chlorobenzylidene): 2,4-O-(3-bromo-4-isopropylbenzylidene)sorbitol, 1,3-O-(4-t-butylbenzylidene):2,4-O-(3,4-dimethylbenzylidene) sorbitol, 1,3-O-(3,4-dimethylbenzylidene):2,4-O-(t-butylbenzylidene)sorbitol, 1,3-O-(3,4-dimethoxybenzylidene):2,4-O-(3,4-dimethylbenzylidene) sorbitol, 1,3-O-(3,4-dimethylbenzylidene):2,4-O-(3,4-dimethoxybenzylidene)sorbitol, 1,3-O-(3,4-methylenedioxybenzylidene): 2,4-O-(3,4-dimethylbenzylidene)sorbitol, 1,3-O-(3,4-dimethylbenzylidene): 2,4-O-(3,4-methylenedioxybenzylidene)sorbitol, 1,3-O-(4-isopropylbenzylidene):2,4-O-(3,4-dimethylbenzylidene) sorbitol, 1,3-O-(3,4-dimethylbenzylidene):2,4-O-(4-isopropylbenzylidene)sorbitol, 1,3-O-(3,4-dimethylbenzylidene):2,4-O-(2-naphthylbenzylidene) sorbitol, 1,3-O-(2-naphthylbenzylidene):2,4-O-(3,4-dimethylbenzylidene)sorbitol, 1,3:2,4-bis(4-ethylbenzylidene)-1-allyl-sorbitol, 1,3,2,4-bis)3'methyl-4'fluorobenzylidene)-1-propyl-sorbitol, 1,3,2,4-bis(5'6'7'8'-tetrahydro-2-naphthaldehydebenzylidene)-1-allyl-xylitol, bis-1,3,2,4-(3'4'-dimethylbenzylbenzylidene-1"-methyl-2"-propyl-sorbitol and 1,3,2,4-bis(3',4'-dimethylbenzylidene-1-proplyl-xylitol.

A particularly preferred alditol acetal is represented by bis(3,4-dialkylbenzylidene of formula:

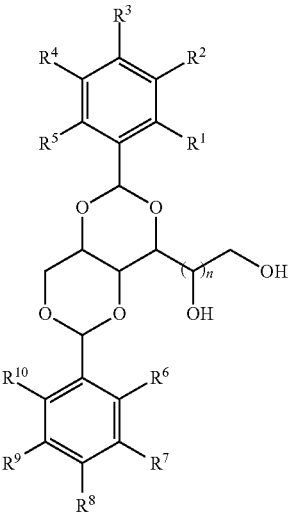

wherein $R^1$-$R^{10}$ are each independently selected from hydrogen, lower alkyl groups containing 1-18 carbon atoms, hydroxy, methoxy, mono- or dialkylamino, nitro and halogen or together form a heterocyclic ring containing up to 5 carbon atoms and n may be 0, 1 or 2.

Alditol acetals, as exemplified by dibenzylidene sorbitol and its analogues have a tendency to gel solvents during extractions or manipulations. Herein, dibenzylidene sorbitol is disclosed as an exemplary functional excipient to inhibit the chemical reduction of a drug substance. In addition, various analogues of dibenzylidene sorbitol are also disclosed wherein the aryl moiety is substituted with alkyl substituents. A preferred embodiment comprises two equivalents of 4-methyl benzaldehyde condensed with sorbitol to produce the desired analogue.

Alditol acetals, such as dibenzylidene sorbitol and its analogues, will consume chemical reducing agents used to illicitly convert pseudoephedrine to methamphetamine. In the context of the present invention, a drug substance as its pamoate salt can be formulated with alditol acetal and other excipients to form a dosage drug product. Attempts to isolate the drug substance from this dosage would be complicated by both the organic acid addition salt, as exemplified by pamoate, effect on extractability and the gelling tendency of the alditol acetal. Further, chemical reduction either prior to or after drug substance isolation would be inhibited by both the organic acid addition salt and the alditol acetal consuming reducing agent resulting in a complex mixture.

The alditol acetal, and preferably the organic acid exemplified by Formula A when used as the addition salt or Formula H when used as an additive, each have a chemical reduction potential which is lower than the chemical reduction potential of the amine-containing pharmaceutical. Therefore, in addition to the difficulty associated with isolation of the amine-containing pharmaceutical the reduction to form methamphetamine is significantly hindered.

The organic acid can be an additive to a drug product comprising an amine-containing pharmaceutically active compound. As an additive the organic acid is defined by Structure H:

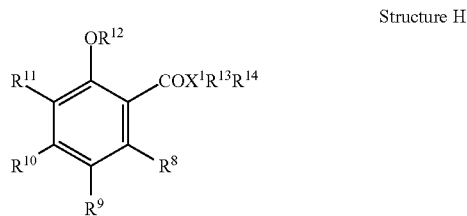

Structure H wherein $R^8$-$R^{11}$ are independently selected from H, alkyl or substituted alkyl of 1-6 carbons, adjacent groups may be taken together to form a cyclic alkyl, cyclic alkyl-aryl, or cyclic aryl moiety;
$R^{12}$ is selected from H, or an alkali earth cation;
$R^{13}$ and $R^{14}$ are independently selected from H, alkyl of 1-6 carbons, an alkali earth cation, and aryl of 6 to 12 carbons, in a number sufficient to complete the valence bonding of $X^1$; and
wherein $X^1$ is selected from nitrogen, oxygen or sulfur.

The additive defined by Formula H is preferably selected from the group consisting of pamoic acid, an alkali earth salt of pamoate, bon acid and an alkali earth salt of bon acid.

The additive defined by Formula H is preferably and amine-containing pharmaceutically active are preferably present in a molar ratio of at least 0.5:1 and more preferably in a molar ratio of between 0.5:1 and 1:1.

In one embodiment the additive defined by Formula H and the amine-containing pharmaceutically active are in a molar ratio of at least 2:1 and preferably no more than 3:1.

Pseudoephedrine, ephedrine, and benzphetamine drug substances can each be used as starting materials for the preparation of methamphetamine. These drug substances are principally available as their hydrochloride salts which are easily isolated from dosage preparations. This property enables the illicit production of methamphetamine in clandestine laboratories. The invention described herein provides physical and chemical barriers to this illicit methamphetamine production at the drug substance and the drug product levels. These barriers are imposed at the drug substance level by the use of organic acid addition salts and at the drug product level by incorporating functional excipients such as dibenzylidene sorbitol and/or its analogues.

Figure 33:
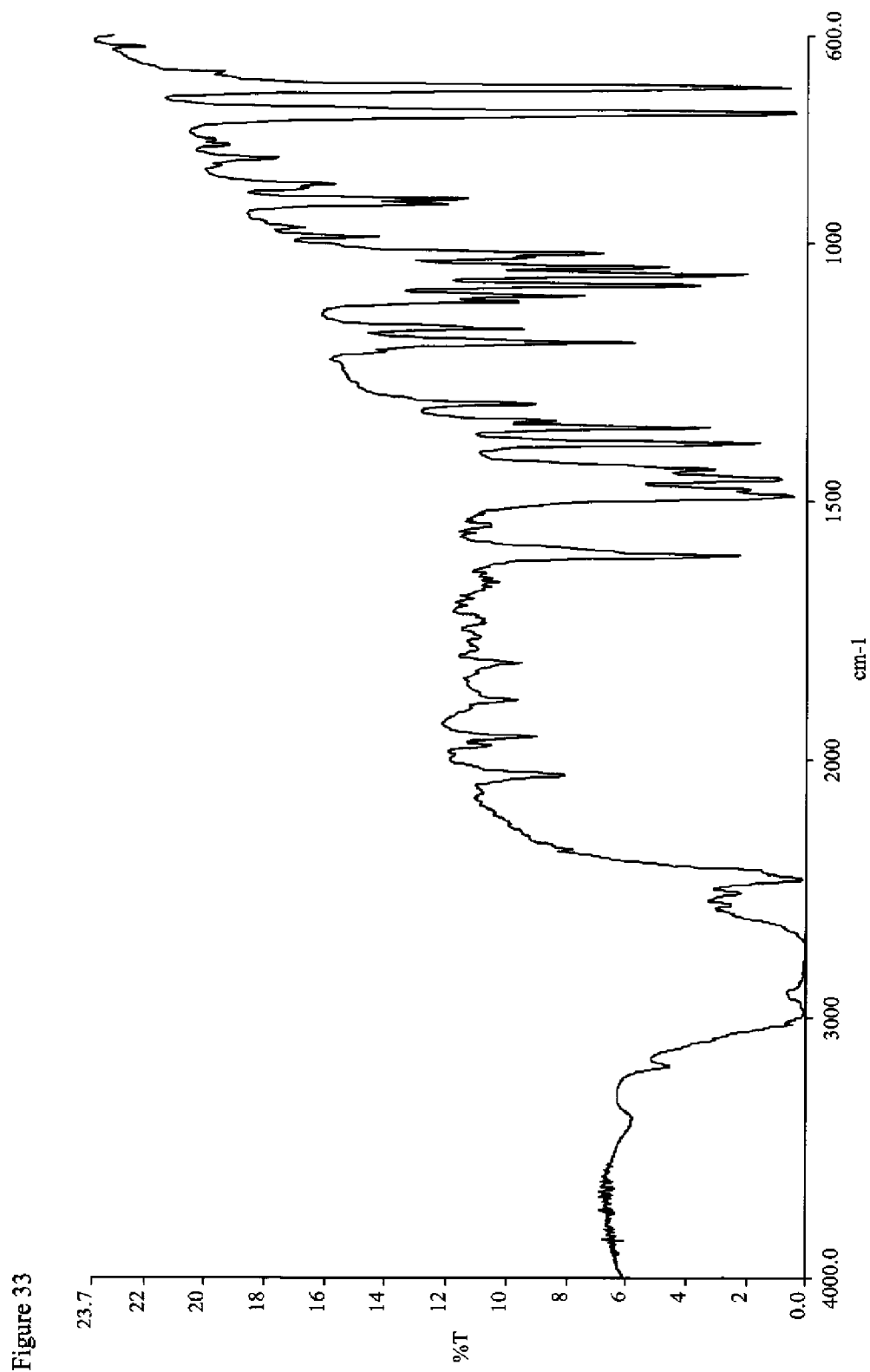
FIG. 33 the Fourier Transform Infrared (FTIR) spectrum of methamphetamine hydrochloride.
Figure 34:
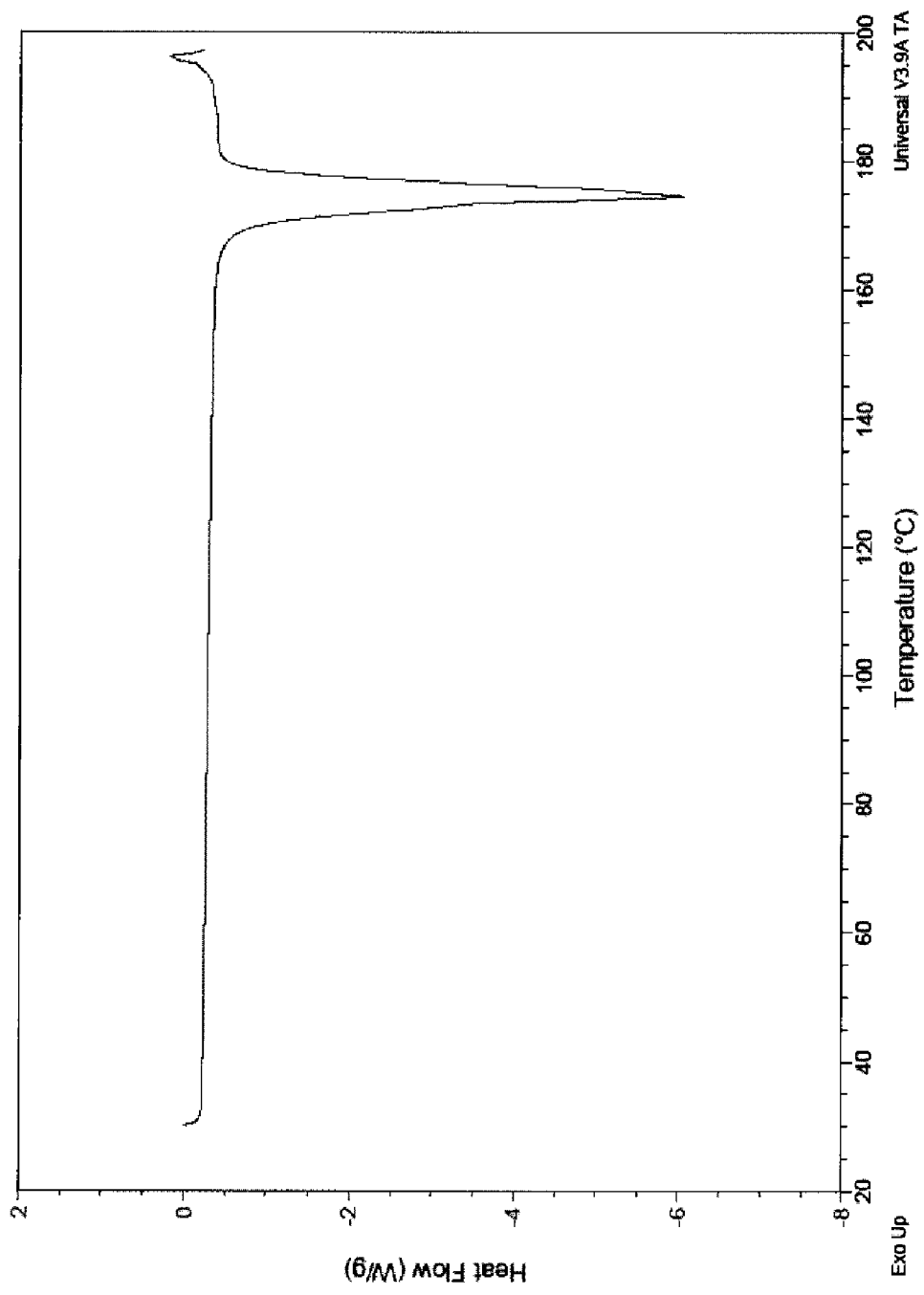
FIG. 34 is the Differential Scanning calorimetry (DSC) thermogram of methamphetamine hydrochloride.
Figure 35:
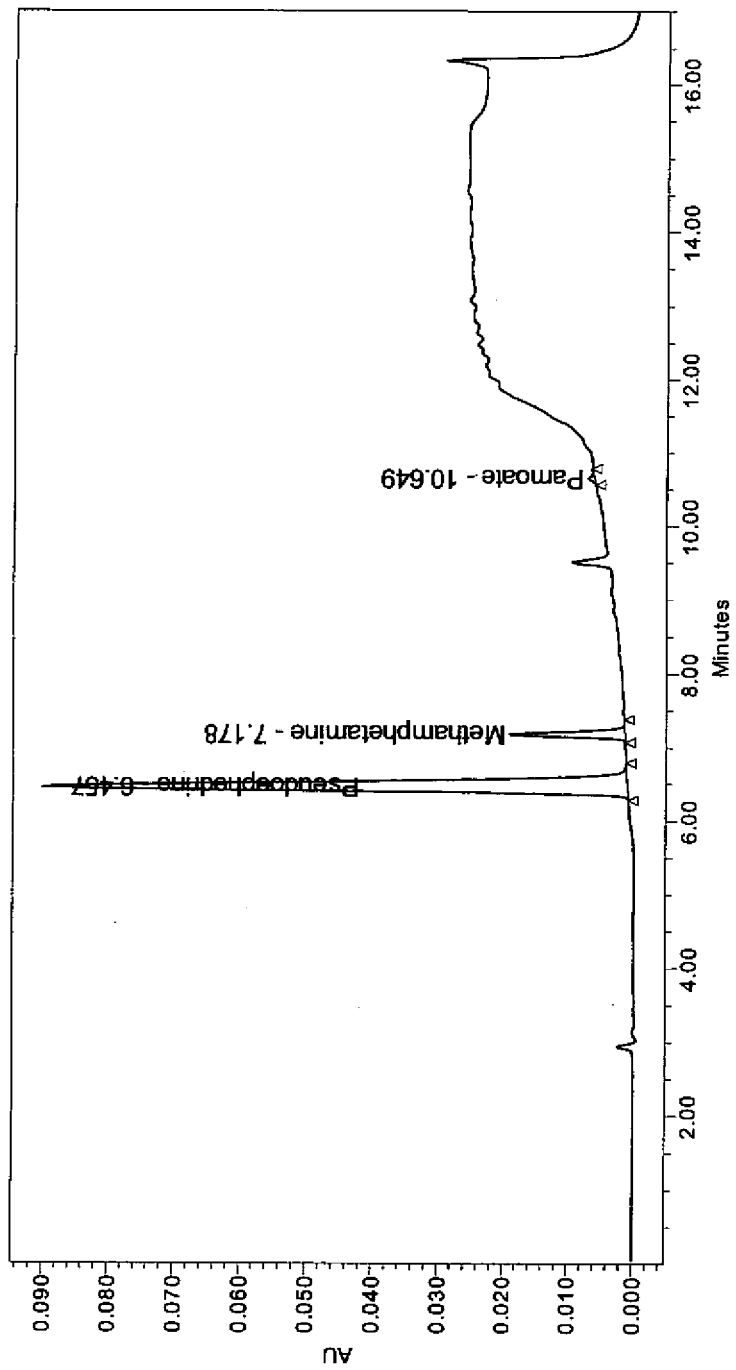
FIG. 35 is the High Performance Liquid Chromatography (HPLC) chromatogram of partially reduced pseudoephedrine pamoate.
Figure 36:
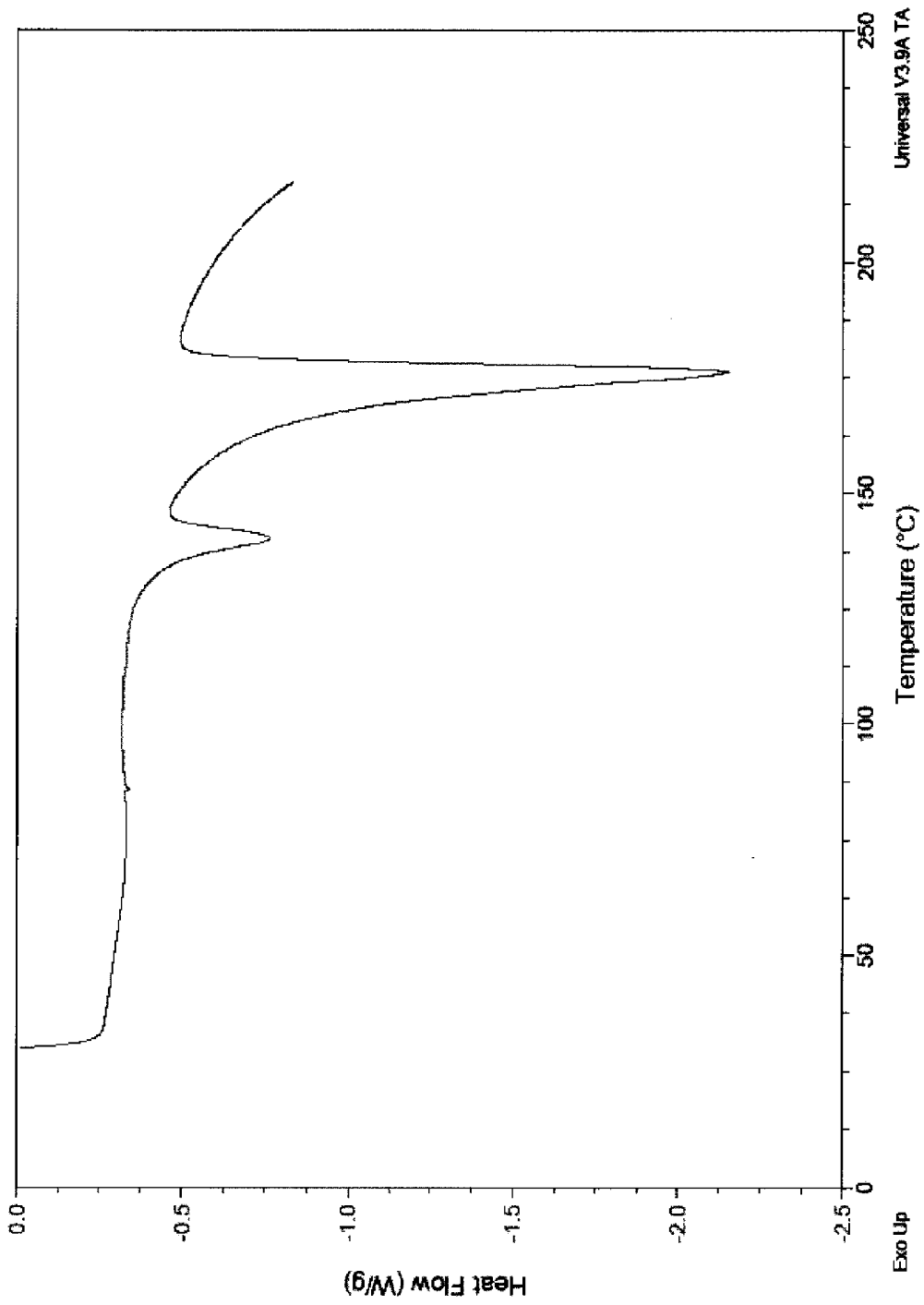
FIG. 36 is the DSC thermogram of the partially reduced pseudoephedrine pamoate.
Figure 37:
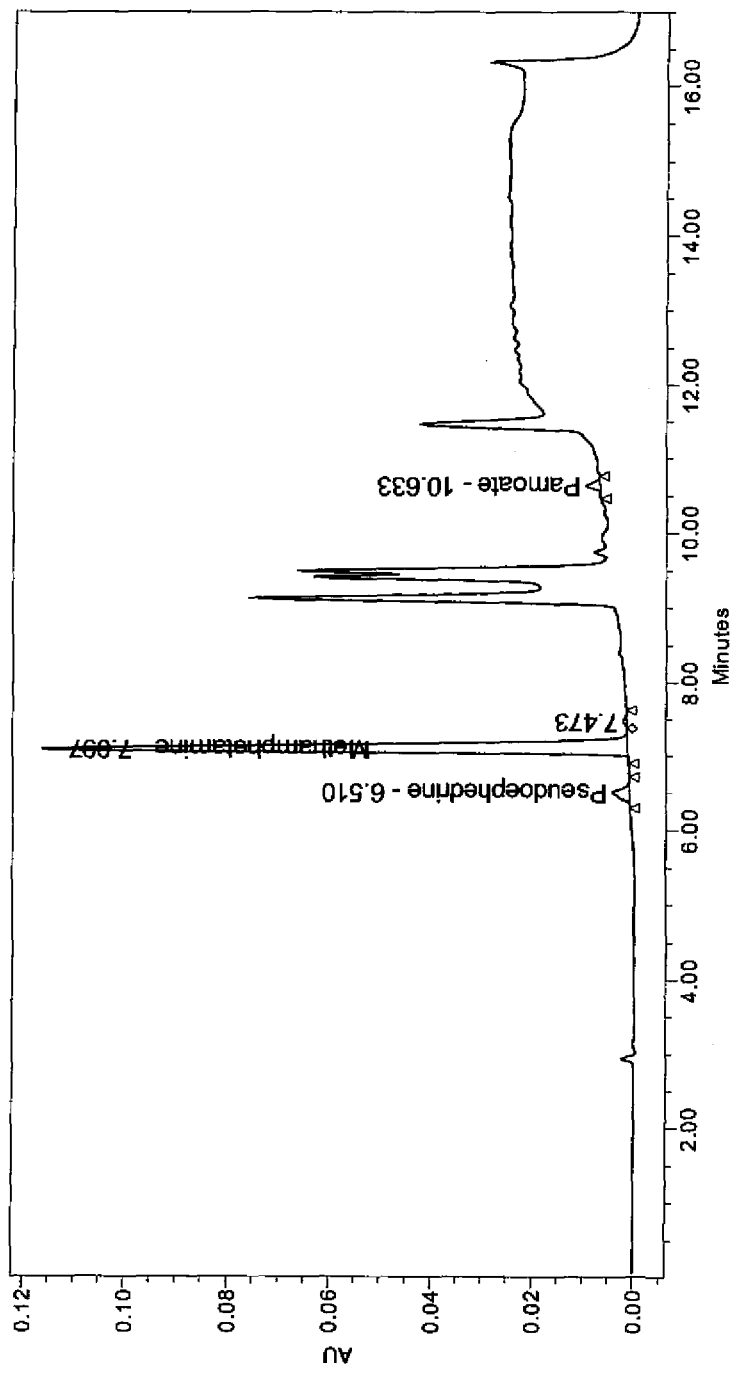
FIG. 37 is the HPLC chromatogram of the reduced pseudoephedrine pamoate.
Figure 38:
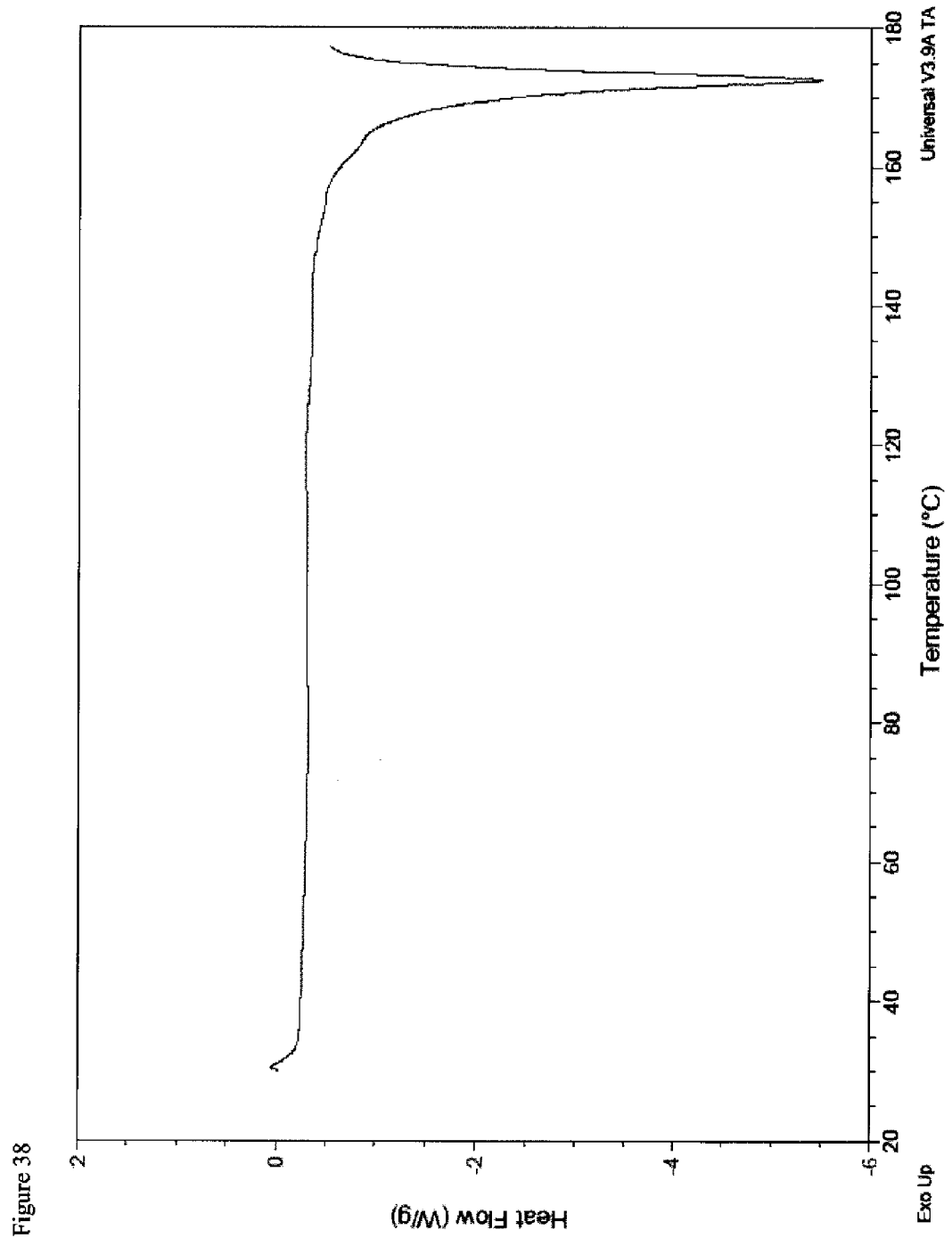
FIG. 38 is the DSC thermogram of the reduced pseudoephedrine pamoate.
Figure 39:
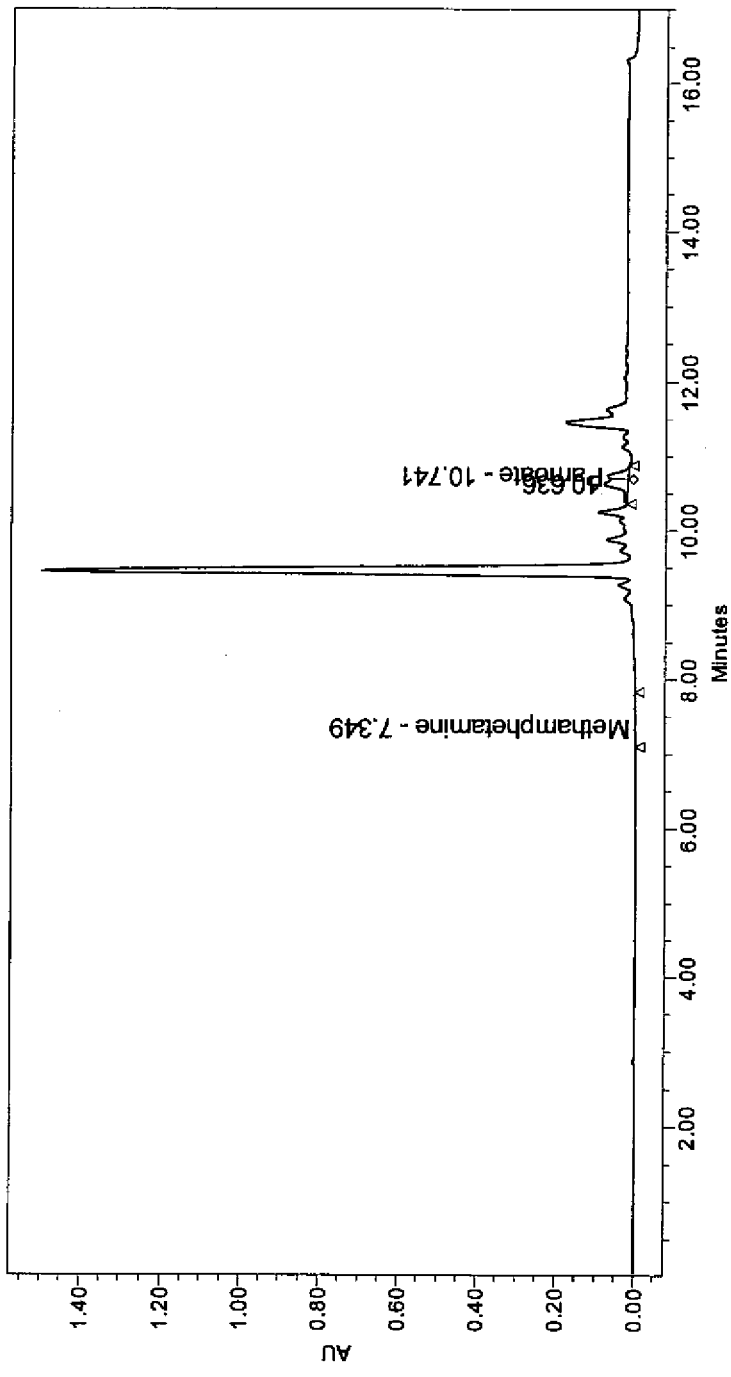
FIG. 39 is the HPLC chromatogram of reduced pamoic acid.

Analytical confirmation of the invention is provided from the experimental results. First, pseudoephedrine hydrochloride was reduced to provide methamphetamine which was characterized as its hydrochloride salt. FIG. 33 is the Fourier Transform Infrared Spectrum of methamphetamine hydrochloride; FIG. 34 is the Differential Scanning calorimetry thermogram of the material (phase transition observed at about 175° C.; lit. 170-175° C.). With the methamphetamine reaction marker in-hand, the attempted reduction of pseudoephedrine pamoate was performed using about twice the number of equivalents of lithium that would be prescribed for pseudoephedrine. FIG. 35 is the High Performance Liquid Chromatography (HPLC) chromatogram of the reaction product which indicates the reaction did not go to completion. FIG. 36 is the associated DSC of the reaction product isolated. In contrast, when an approximately four-fold stoichiometric excess of lithium was employed over that employed to reduce pseudoephedrine, pseudoephedrine pamoate could be reduced to methamphetamine. FIG. 37 is the HPLC chromatogram of the product isolated and is indicative of a practical conversion of pseudoephedrine pamoate to methamphetamine. Again, this conversion is only accomplished when a large excess of reducing agent is employed. FIG. 38 is the DSC thermogram of the isolated methamphetamine hydrochloride. FIG. 39 is the HPLC chromatogram of reduced pamoic acid, confirming that the pamoate moiety is susceptible to the reduction conditions and interferes with the "desired" reduction of pseudoephedrine.

Figure 40:
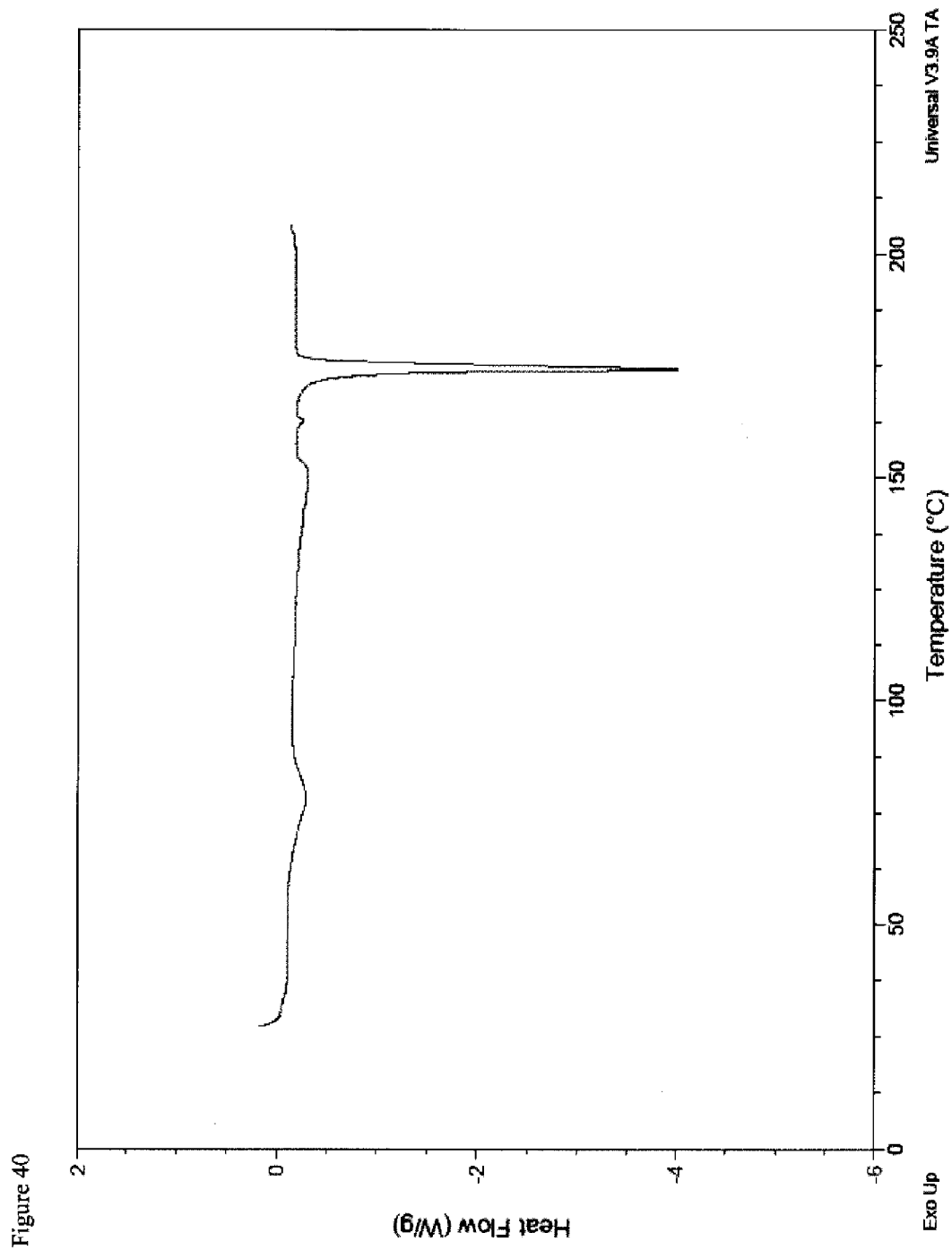
FIG. 40 is the DSC thermogram of HI/red phosphorous reduced pseudoephedrine hydrochloride.
Figure 41:
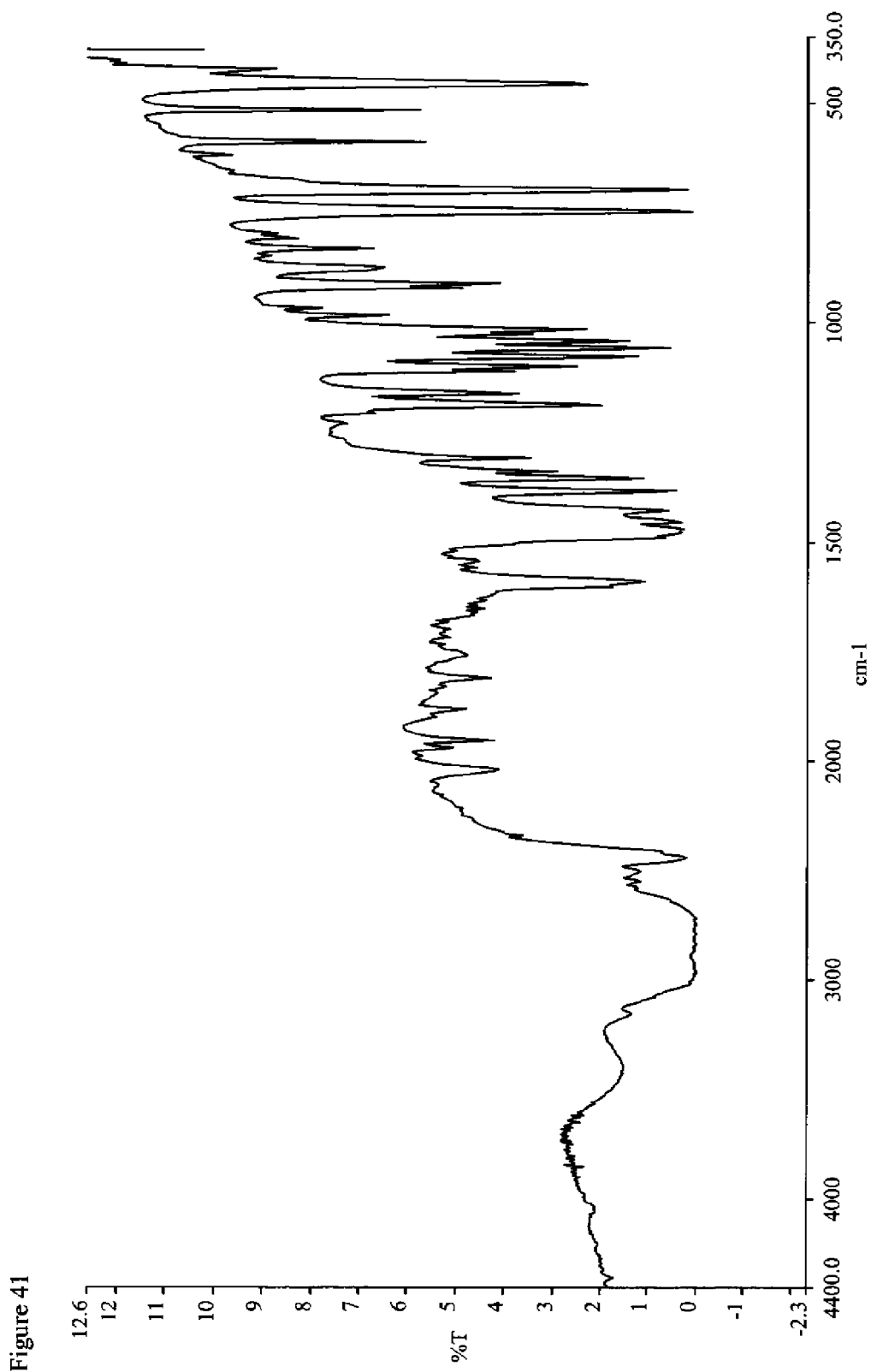
FIG. 41 is the FTIR spectrum of HI/red phosphorous reduced pseudoephedrine hydrochloride.
Figure 42:
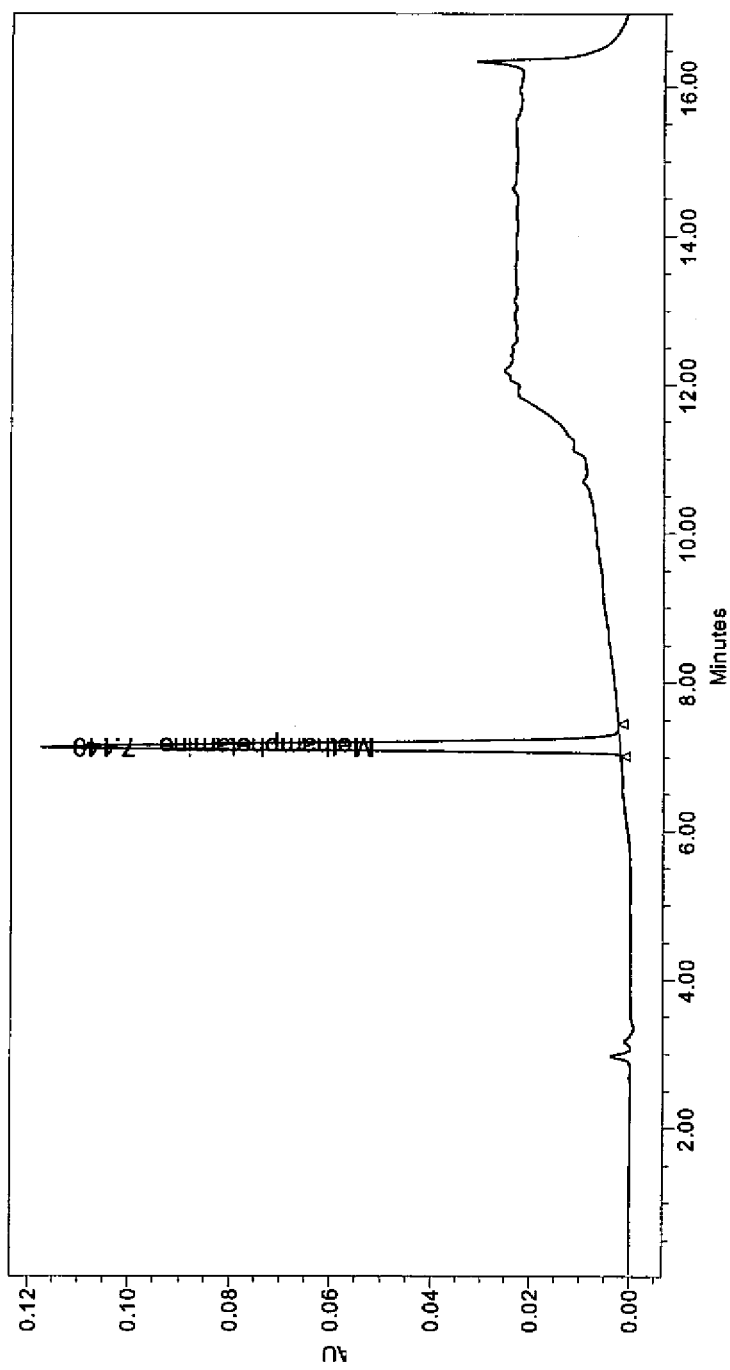
FIG. 42 is the HPLC chromatogram of the HI/red phosphorous reduced pseudoephedrine hydrochloride.
Figure 43:
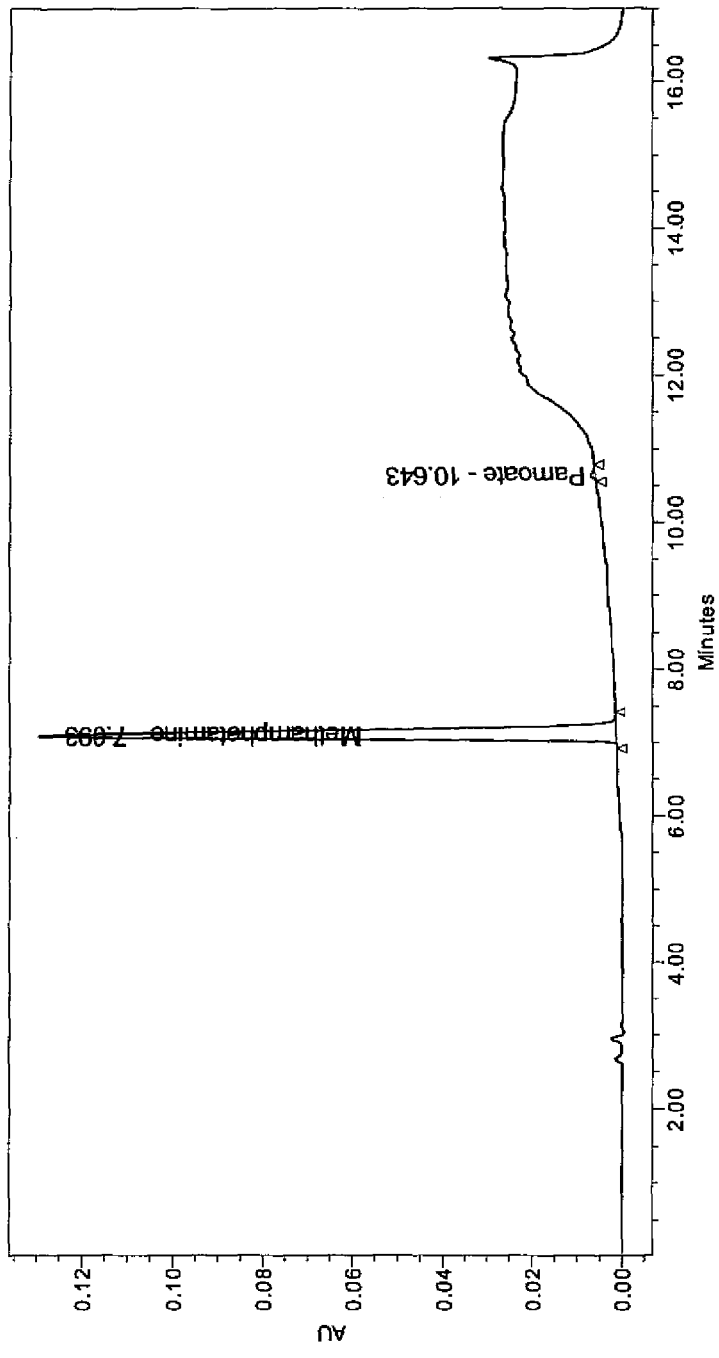
FIG. 43 is the HPLC chromatogram of the HI/red phosphorous reduced pseudoephedrine pamoate.

The red phosphorous/hydriodic acid reduction pathway was similarly explored for pseudoephedrine hydrochloride and pseudoephedrine pamoate. FIGS. 40, 41, and 42 represent the DSC thermogram, FTIR spectrum and HPLC chromatogram, respectively, of the methamphetamine hydrochloride obtained from the reduction of pseudoephedrine. The reduction medium's acidic nature (containing hydriodic acid) complicates the reduction of pseudoephedrine pamoate causing precipitation of pamoic acid. Under these conditions, the competitive reduction of pseudoephedrine versus reduction of the pamoate moiety is preferential to the drug substance. FIG. 43 is the HPLC chromatogram confirming the presence of methamphetamine.

The alditol acetal may be employed in the formulation with pseudoephedrine hydrochloride or with pseudoephedrine present as its organic acid addition salt, such as pseudoephedrine pamoate. Dibenzylidene sorbitol, as a representative alditol acetal, was subjected to the dissolving metal (Birch) reduction procedure and the reaction mixture analyzed by gas chromatography. The presence of toluene was confirmed which demonstrated the acetal moieties initially present in dibenzylidene sorbitol had been reduced.

The disclosure herein should not be construed to limit the scope of the invention, but are presented to demonstrate the utility of organic acid addition salts in providing useful medications to the public without the liability of the illicit production of methamphetamine. Additionally, the organic acid addition salts may be formulated with functional excipients which further provide a barrier to the reductive processes leading to methamphetamine. A substantial commercial application is available by the implementation of this invention to restore over-the-counter medications to the general public.

Independent of the route of administration, it is axiomatic that a drug substance must be bio-available in its intended physiological environment in order for it to elicit the desired pharmaceutical effect. Indeed, the number of pharmaceutical products based on insoluble amine salts is very limited and not surprisingly, the pharmaceutical literature describing the absorption benefits of otherwise insoluble amine salts is essentially non-existent. Basically, the literature teaches that higher solubility in general implies better bio-availability. While entirely speculative, the use of insoluble salts was probably avoided because practitioners of the art incorrectly correlated poor API aqueous solubility with poor bio-availability. Indeed, the commercial success of mineral acid salts of amine-containing APIs suggests a negative teaching away from insoluble salts. An unexpected observation and correct correlation pertaining to the current invention is that selective, or engineered API aqueous release properties inhibits illicit use, or drug abuse, of the API and its associated products while retaining the bio-availability when employed for its intended purpose. And indeed, these features can be provided by employing a host of organic acids.

The actual basis for the invention is more complex than an insolubility feature of an API pamoate salt (or associated family of organic acid salts). As mentioned in the introduction and as will be shown in the experimental section and associated figures, the dissolution behavior of these organic acid salts of amine-containing APIs provide the unanticipated observation that these compounds can be employed in targeted release applications, and in particular to address drug abuse. As performed according to test procedures recognized by the United States Food and Drug Administration and documented within the United States Pharmacopeia (USP), dissolution properties are established as a function of time, temperature, concentration and pH. In particular, one test established the saturation solubility of the drug substance and is performed over a pH range to correlate with the physiological pH ranges the drug may encounter during use. For instance, the test employs a pH of about 1 to represent simulated gastric fluid. At the other end of the range, a pH of about 7.4 is employed to represent blood pH. Intermediate pH's are also tested to evaluate the drug's dissolution properties over the entire range.

The present invention is applicable to a variety of drug delivery presentations including solid oral dose, parenteral dosage forms (depo-type products) and by devices and formulations suitable for transdermal delivery and nasal/inhalation administration. It is responsibly acknowledged that many factors may influence the overall pharmacokinetic profile of a drug product, for instance, the particle size distribution of the drug substance may markedly influence drug substance bioavailability. Hence, the optimum practice of this invention when employed for a specific drug product must account for the multitude of additional factors. The benefit of the current invention is a means to provide a dominating or controlling factor to prevent abuse while achieving efficacious and therapeutic patient dosages to which refinements, adjustments or modifications can be asserted to yield an optimal response.

The three alternate mechanistic approaches presented earlier, (antagonist, prodrug and formulation, attempt to address abuse potential by impacting the route of administration, or to differentiate the physiological environment in which the drug fulfills its intended purpose versus the drug's misuse. Each of these routes was shown to possess inherent limitations for mitigating drug abuse. For the purposes of additional clarity and completeness, the mineral acid salts, which are typically abused, do not exhibit a suitable means to prevent abuse. The dissolution properties of the mineral acid salts of the physiologically active and/or controlled substance amines consistently exhibit high dissolution rates and substantial achievable release rates (85-100%) over the entire physiological pH range.

In contrast, it is relevant to the present invention to note the importance of pH in controlling the release of a drug substance from its product formulation to achieve absorption and consequently, the medicinal effect. The pH of the gastrointestinal tract essentially remains highly acidic with the exception of the lower colon which reaches pH 8; vaginal pH is typically around 5.8 and the nasal cavity is approximately pH 4.5. More generally, each of the mucosal surfaces, particularly ocular, nasal, pulmonary, buccal, sublingual, gingival, rectal and vaginal are receptive to drug absorption if release can occur. A dominating feature of the present invention is the severely retarded release of the controlled substance, particularly amine-containing pamoate salt (or related salt family) in the pH range of about 4 to 9 which encompasses the physiological pH of the mucosa. These release properties were an unexpected finding recognized and observed after performing dissolution tests over a wide pH range on several unrelated compounds. The release properties and saturation solubility profiles are a means to evaluate a reasonable dosage application to the mucosa. The non-release of the drug in the 4 to 9 pH range negates absorption and prevents the physical act of abuse. For the amine-containing hydrochloride salts, an abuse mechanism remains operative since these salts do not exhibit the discriminating "on/off" switch of the present invention.

An experimental refinement of the dissolution tests was performed on several compounds to better represent the physiological conditions encountered during abuse attempts and to account for the saturation solubility factor. Further, control experiments were included in the experimental design to compare the organic acid addition salts of the current invention with the hydrochloride salts of identical amine-containing controlled substances. In some cases, model compounds were used to demonstrate the principles of the invention instead of using compounds legally designated as controlled substances. Side-by-side dissolution experiments on hydrochloride salts versus those of the present invention were conducted at three different pH conditions: a) a pH of about 1 to simulate gastric conditions, b) pH of about 4.5 to simulate mucosal surface pH, and c) a pH of about 7 to evaluate a potential pH range of mucosal surfaces and blood pH for purposes of simulating injection. In addition, the experimentation was designed to demonstrate the equivalence of the organic acid addition salts to the mineral acid salts if used by their intended route of oral administration route and hence the concentration effects were included in the study. For oral administration of a dosage form, the United States Pharmacopeia (USP) recommends the immediate release testing procedure on a unit dosage to be performed on a simulated stomach "solution" volume of 900 mL. For the mucosal membranes, the available mucous fluid may be better approximated at 10 mL. Hence, dissolution tests were conducted at different concentrations at the different pH levels. Besides temperature, pH and concentration, the time factor was also evaluated under the presumption that an individual abusing a drug will want to obtain their anticipated physiological response within an hour.

It was observed that the organic acid addition salts under simulated mucosal conditions were not released whereas the hydrochloride salts released rapidly (refer to FIGS. 26-32). Therefore, recovery studies from the simulated mucosal environments were more appropriate for demonstrating the inability of the organic acid salt to release the active ingredient and thereby prevent a physiological response. Therefore, the abuse mechanism was inoperative. For simulated gastric ingestion, the organic acid addition salts exhibited a release property during dissolution testing essentially equivalent to the hydrochloride salts' dissolution properties in that both presentations were essentially immediately available (refer to FIGS. 16 through 25). To summarize the trends, the organic acid addition salts were highly available for absorption at gastric pH. Secondly, the organic acid addition salts exhibit a low release rate under mucosal conditions. And lastly, the organic acid addition salts exhibit a low level of release under the mucosal conditions (see FIGS. 26-32). These definitive examples support the present invention's duality of providing an abuse controlling mechanism and yet retaining the desired medicinal benefit of the drug substance when used in the intended manner.

For confirming tests and to demonstrate general applicability of the targeted release properties of the amine-containing organic acid addition salts, a model compound was selected to challenge the hypothesis. Imipramine was chosen as a representative amine-containing compound for study comparison of its hydrochloride and organic acid addition salts, namely pamoate, xinafoate and salicylate salts. The selection of imipramine was based on practical considerations since working with controlled substances has legal and moral responsibilities and imipramine fulfilled the structural features associated with many amine-containing controlled substances. These structural features often include: at least one nitrogen; at least one aromatic ring; ideally the multi-ring/fused ring/heterocyclic sub-structures observed in many controlled substances; lipophilicity as the free base; the salts exhibit sufficient stability for the duration of the test regimens so as to minimize interference and potentially incorrect conclusions attributed to degradation products or impurities and the various salts employed in the tests could be readily synthesized and characterized. Clearly, the controlled substance designation to an amine-containing compound having physiological activity is a legal assignment/ assessment and has little to no relevance to chemical structure or physical behavior. Hence, the scope of the invention is well supported by the selection of controlled and non-controlled substances exhibiting structural variation to evaluate the novel and unexpected observations disclosed herein.

Also disclosed herein are processes for the preparation of drug substances and DEA controlled drug substances (APIs) using organic acid addition salts of the active pharmaceutical ingredient (API) which are optionally formulated with other non-therapeutic materials to aid in delivery, stability, efficacy, targeted release and to engineer a pharmacokinetic profile of the organic acid addition salts as compared to other salt forms, including inorganic (mineral) acid salt forms. The present invention provides for release of the API for its intended purpose and prevents availability of the drug substance for typical routes of abuse. The present invention describes a method for evaluating, and formulations for, the organic acid addition salts of appropriate APIs to provide an efficacious and therapeutic dosage to animals and humans.

The present invention practically and financially thwarts efforts to convert drug substances to their corresponding mineral acid salt(s). This severely restricts, limits, reduces or eliminates the efforts of purposeful de-formulation of commercially available drug products into a form suitable for physiological absorption in a manner different than intended by the original commercial formulation. The drug substance cannot be easily modified for alternate routes of administration without numerous, involved and technically sophisticated chemical transformations and isolations. Simultaneously, many of these drug products prone to abuse serve valuable and beneficial purposes in society and the invention retains the properties of the drug product (and in some cases enhances them) when used for the intended purpose. The benefits of the present invention are those described above and can be practiced while retaining the complex requirements reviewed below.

A drug formulation which is selected for the prevention of drug abuse is specifically a drug which is bio-unavailable or not isolable if efforts to alter the intended or established route of administration are undertaken. In a preferred embodiment the drug formulation is not released under aqueous conditions at a pH of about 4 to about 9 and generates a solid of an organic acid at pH below about 4. At pH above about 9, the organic acid (as its inorganic salt) and the amine containing active pharmaceutical ingredient (as its free base) are sufficiently soluble as to prevent separation of the components and thus inhibiting direct isolation of the API (as its free base) without additional processing.

In the present invention a drug product can be prescribed and administered in a manner wherein proper administration provides a therapeutic effect and the function of the API is realized. With a different manner of administration, in other words, a non-therapeutic administration the API does not enter the bloodstream in an amount sufficient to be active. To be effective the API must be bio-available. For the purposes of the present invention, one method of establishing a compound's bio-availability is by determining the percentage of weight API recovered from an aqueous solution at a pH representative of the method of administration described herein. For the purposes of the present invention a compound is considered to be effective when at least 85 wt % of the compound is recovered from an aqueous solution at a pH representative of the method of administration. If, for example, 85 weight percent or more of a drug compound is recovered from a solution at a pH of 4-9, pH 7 for example, the material is considered to be bio-unavailable at a mucosal membrane and is considered non-permeable at the mucosal membrane and the compound exhibits prophylactic properties. If, for example, less than 85 weight percent of a drug compound is recovered from a solution at a pH of less than 4, pH 1 for example, the material is considered to be bio-available under oral administration and is considered permeable in, for example, the gastrointestinal tract due to the release of the API at the pH of the gastrointestinal tract.

A particularly preferred embodiment and method of administering the amine-containing pharmaceutically active compound is by oral dose. The oral dose is prepared by first preparing an organic acid salt of the active compound. The organic salt is then formulated into a carrier matrix to provide an oral dose drug product. The carrier matrix is composed of ingredients (excipients) optionally selected from the group, but not limited to binders, fillers, flow enhancers, surfactants, disintegrants, buffers, and the like, typically employed in the art and found in the "Handbook of Pharmaceutical Excipients", Rowe, Sheskey and Owen (Editors), Fifth Edition, 2006, Pharmaceutical Press (publishers). When the oral dose is ingested the organic salt dissociates under physiological conditions. The organic acid portion of the amine-containing organic acid addition salt forms the insoluble (organic) acid while the active compound is liberated and becomes bio-available. Efforts to directly isolate the active compound from the oral dose would be thwarted as described herein.

A common technique for de-formulating drug products, particularly for illicit use, is to isolate the active ingredient by organic phase extraction and separation from an aqueous environment. An example of such illicit activity is extraction of highly soluble ephedrine hydrochloride or pseudoephedrine hydrochloride with isopropanol, which is more commonly known as rubbing alcohol. In an embodiment of the present invention, both pseudoephedrine pamoate and ephedrine pamoate and their related family of salts are insoluble in isopropanol and other organic solvents such as acetone and toluene.

In an embodiment of the present invention, the controlled substance is an amine-containing organic salt which does not release in the pH window of about 4 to about 9. At a pH of less than about 4, the subject organic salts become protonated with the concomitant precipitation of organic acid. At pH greater than about 9, the addition salt is soluble yet it is quite difficult to distinguish between the organic acid component and the active amine by organic solvent extraction.

The organic acids of the present invention are those forming salts with amine-containing active pharmaceutical ingredients which do not release in an aqueous solution within a pH window of about 4 to about 9 and which interfere with the direct isolation of the API outside of the central pH window.

The organic acid is defined by the following Structures A through G wherein Structure A represents the general family compounds embodied within the invention listed as a Markush Group. Structure B represents the subset of salicylic acid and its derivatives conceived as a component of this invention. Structures C, D and E are regio-isomeric variations on Compound A wherein two adjacent substituents on Compound A form a fused aryl ring (i.e. $R^1+R^2$; $R^2+R^3$; and $R^3+R^4$). Structures F and G represent a further sub-category of dimer-like compounds derived from Structure A. In Structure F, dimerization has occurred through $R^4$ of two Structure A compounds with both possessing fused-aryl ring systems formed via $R^2+R^3$. In Structure G, dimerization has again occurred through $R^4$ of two Structure A compounds however both Structure A residues possess fused-aryl ring systems formed via $R^1+R^2$.

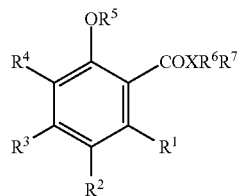

Structure A

Wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X (e.g. to provide a mixed anhydride or carbamate); X is selected from nitrogen, oxygen or sulfur, and when X=O, $R^6+R^7$ may represent an alkali earth cation, ammonium or together form a heterocyclic moiety;

Particularly preferred organic acids include Structures B through E.

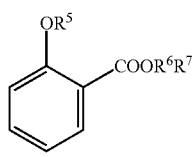

Structure B wherein $R^5$, $R^6$ and $R^7$ remain as defined above for Structure A;

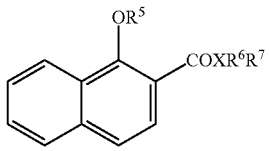

Structure C wherein X, $R^5$, $R^6$ and $R^7$ remain as defined above for Structure A and more preferably X is O;

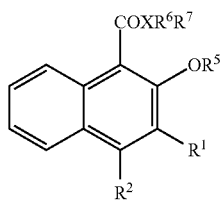

Structure D wherein X, $R^1$, $R^2$, $R^5$, $R^6$ and $R^7$ remain as defined above for Structure A and more preferably X is O; $R^1$ and $R^2$ are hydrogen;

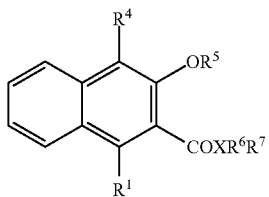

Structure E wherein X, $R^1$, $R^4$, $R^5$, $R^6$ and $R^7$ remain as defined above for Structure A and more preferably X is O, $R^1$ and $R^4$ are hydrogen;

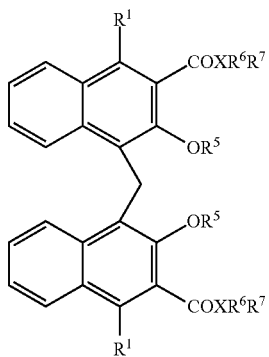

Structure F wherein X, $R^1$, $R^5$, $R^6$ and Rare independently defined as above for Structure A and more preferably at least one X is O and at least one $R^1$ is hydrogen; and

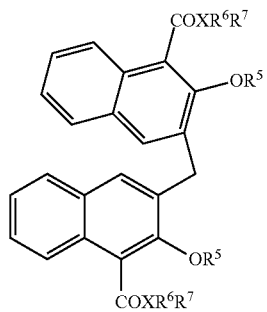

Structure G wherein X, $R^5$, $R^6$ and $R^7$ are independently defined as above for Structure A and more preferably X is O and $R^5$ is hydrogen.

Pamoic acid, or a synthetic equivalent of pamoic acid, is the preferred embodiment. Pamoic acid has a formula corresponding to Structure F wherein X is O; $R^5$, $R^6$ and $R^7$ are hydrogen.

A synthetic equivalent of pamoic acid is a material that provides the structural moiety independent of its particular salt, ester, or amide form and that upon pH adjustment yields pamoate functionality suitable for reaction, optionally with one or two equivalents of an amine-containing active pharmaceutical ingredient to form a pamoate salt. Examples of synthetic equivalents of pamoic acid capable of manipulation to produce pamoate salts include but are not limited to, disodium pamoate, di-ammonium pamoate, di-potassium pamoate, lower molecular weight di-alkyl and/or di-aryl amine pamoate, lower molecular weight di-alkyl and/or di-aryl esters of pamoic acid, and lower molecular weight di-alkylacyl and/or di-arylacyl O-esters of pamoic acid, i.e. those alkylacyl and arylacyl esters formed using the hydroxyl moiety of pamoic acid and not the carboxylic acid functional group. The descriptor phrase "lower molecular weight" used above means the indicated moiety has a molecular mass contribution within the pamoate derivative of less than about 200 amu.

For clarity, the use of lower molecular weight di-alkyl or di-aryl amine pamoate allows for the exchange of higher molecular weight amines, or drug free bases, to be exchanged for the lower molecular weight amine component during the salt formation reaction. Similarly, the use of lower molecular weight di-alkylacyl and/or di-arylacyl pamoates allow for their conversion through ester hydrolysis to the pamoic/pamoate moiety followed by reaction with the desired drug free base.

In a preferred embodiment of the invention, at least one equivalent of the amine containing drug substance is reacted per mole of disodium pamoate to yield the drug substance pamoic acid salt. Preferably, 2:1, 1:1, or mixtures thereof, equivalents of amine per mole pamoic acid moiety or related organic acid are prepared. Typically, an aqueous acidic solution of the amine containing drug substance is combined with a basic solution of pamoic acid or disodium pamoate. The acid/base reaction ensues and the insoluble organic acid salt precipitates from the aqueous solution. Optionally, the salt can be purified, dried and milled to obtain a drug substance ready for formulation into the desired delivery format. The drug product formulated with the drug substances then possesses the targeted delivery characteristics of the drug substance and the potential for abuse of either the drug substance and/or drug product is eliminated or greatly reduced when abuse is attempted via the mucosal surfaces or by injection.

Another feature of the invention is the preparation of pamoate salts for legitimate active pharmaceutical ingredients wherein the active pharmaceutical ingredient is otherwise used as a synthetic raw material in the illegal or illicit production of dangerous drugs. More specifically, the invention encompasses the preparation and composition of pseudoephedrine pamoate and ephedrine pamoate. The insolubility of these compounds in organic solvents thwarts attempts to extract pseudoephedrine and/or ephedrine from drug products. These compounds when subjected to the illicit activities of methamphetamine production, a first step of which is to attempt extraction of the pseudoephedrine pamoate or ephedrine pamoate from tablets or capsules usually with an alcohol solvent, results in an intractable residue of insoluble excipients and pseudoephedrine pamoate or ephedrine pamoate. Here too, the pamoate salts are for illustration and a broader family of organic acid salts (vide supra) may be employed for practicing the invention.

For the purposes of the present invention an API of a drug product is not directly isolable if it can not be isolated by solubilizing the drug product to form a solubilized drug substance and filtering the solubilized drug substance without further chemical processing.

Another feature of the invention addresses a significant commercial and long-felt need to return the availability of traditional over-the-counter (OTC) drug products to the unrestricted aisles and shelves of drug stores and pharmacies. Historically, products containing pseudoephedrine and/or ephedrine were readily available to the general public and served to provide relief for cold, cough, decongestion, and allergy symptoms. Commerce has been severely impeded for these products due to governmental controls placed on their sale and distribution in an attempt to mitigate diversion for the production of methamphetamine. When intended for the preparation of methamphetamine, pseudoephedrine or ephedrine must be obtained in reasonably pure form prior to the chemical reduction step of benzylic hydroxyl removal. This chemical reduction step provides a second active pharmaceutical ingredient, methamphetamine, usually intended for illicit use or for the behavioral act of drug abuse.

Isolation of pseudoephedrine or ephedrine from drug products formulated with the insoluble organic acid additional salts of the present invention such as pseudoephedrine pamoate or ephedrine pamoate require tedious and costly multi-step isolation techniques comprising the steps of:
a) suspension of the drug product in an aqueous medium;
b) careful pH adjustment
c) filtration of the insoluble excipients and the pamoic acid moiety
d) extraction of the active ingredient into a water immiscible solvent;
e) washing the water immiscible solvent containing the active ingredient;
f) drying the solvent;
g) optionally evaporating the solvent to obtain the active ingredient; or
h) optionally precipitating the active ingredient by forming its mineral acid salt, followed by:
i) isolating the active ingredient as its mineral acid salt by filtration; and
j) drying the mineral acid salt;
wherein the excipients may include starch, talc, lactose or another sugar or sugar derivatives, magnesium stearate, gelatin, colorants, dyes, flow enhancers, anti-statics, preservatives, compression aids, buffers and the like. The presence of these inert ingredients or formulation additives severely complicates and impedes the isolation of purified pseudoephedrine or ephedrine employing the processing steps listed above.

An "alkaloid" is an amine nitrogen containing natural product, or synthetically modified or derivatized natural product, or wholly synthesized analog of a natural product, or an amine containing compound that exhibits biological activity in animals or humans. The amine nitrogen can be present as a primary, secondary, tertiary or quaternary amine moiety and a given compound may contain more than one type of amine functionality. Examples of these materials are the US Drug Enforcement Agency's (DEA) Form 225 of Schedule I through V controlled substances, generally divided between narcotic and non-narcotic materials. There are also other compounds applicable to the present invention not found on the DEA list or which may be added to it in the future. Further, the compounds applicable to the present invention may arise from plant or animal origin, or may be totally obtained through human effort of design and synthesis. A reference to compound classes (pharmocophores) applicable to the invention are found within *Strategies for Organic Drug Synthesis*, by Daniel Lednicer, published by John Wiley and Sons, Inc. © 1998, Chapters 7 through 13 inclusive and individually, Chapter's 13 and 15. Classes of compounds subject to this invention include but are not limited to opiates, morphinoids, tropinoids, amphetamines, compounds containing a piperidine or substituted piperidine sub-structure within the molecule, benzodiazepines, benzazepines, and compounds containing a phenethyl amine or substituted phenethylamine sub-structure within the molecule. The common characteristic to each compound is the presence of an amine nitrogen whereby the amine nitrogen is either a primary, secondary or tertiary amine group and is capable of forming a salt with an inorganic or organic acid, or combinations thereof. Within the description of the invention, the term alkaloid or amine may be used interchangeably to identify a compound possessing, or suspected of possessing, biological activity in humans or animals, in its free base (non-salt form) or in a salt form. The differentiating factor defining the invention is the alkaloid's ability to form an organic acid salt that will retain the expected biological activity when used as intended for legitimate therapeutic purposes, but is not readily accessible for abuse by inhalation (smoking), mucosal application, nasal absorption (snorting) or by intravenous injection (shooting).

A "drug substance" is a molecular entity or compound, also known as an active pharmaceutical ingredient (API) that exhibits biological activity for the purpose of providing human or animal medication to treat disease, pain or any medically diagnosed condition. It is possible for a drug substance to be used in combination with one or more different drug substances to ultimately impart a biological response in humans or animals. A drug substance is typically formulated with other, non-biologically active compounds to provide a means of predictable and quantitative dosage delivery, or perhaps to impart acceptable stability features to the drug product. What is meant by a drug product is a formulation, mixture or admixture of the drug substance with combinations of excipients, processing aids, buffers and perhaps other inert ingredients that allow delivery of the drug substance by the selected delivery mechanism to the patient at a predictable dosage (the carrier matrix). Various delivery mechanisms include solid oral dosage, for example, pills, tablets, or capsules. Additional delivery systems can include solution or suspension injection dosage forms (including depo drug products), transdermal patches, and nasal or inhalation devices. The dosage is the actual concentration delivered to the patient, and depending upon many factors and the actual delivery system selected, the dosage may be available for essentially immediate release, release over time, or manipulated by additional means for stimulated release such as for example, by irradiation. Immediate release is defined as a drug substance wherein under simulated gastric conditions at least 85% is released within 1 hour.

It is a well-known chemical principle that an acid and a base will react to form a salt. It is sometimes possible to predict the physical and chemical properties of these compounds in generalized concepts such as which way a melting point will change compared to the un-reacted acid or base. Dissolution and dissociation rates of drug salts and their associated achievable solution concentrations are substantially less predictable when attempting to correlate this experimental data to some anticipated bio-availability of the drug. For instance, at a given pH, an observed dissolution rate and the associated solution concentration of the drug may be dissociation controlled (i.e. ionization) rather than governed strictly by solubility parameters. Indeed, different salts of the same amine-containing active ingredient are likely to display diverging mechanisms of bio-availability as a function of pH. As such, an evaluation of amine-containing active ingredients and their different salts would help elucidate their bio-availability mechanisms. This approach could be incorporated into a broader design feature to address drug abuse.

For instance, by manipulating the bio-availability mechanism of a particular API by incorporating functional properties into the API's salt, a design feature is introduced. This feature can also extend to eliminating the ability to simply extract the active ingredient from a finished dosage form and abuse the drug by injection. For illustration, the attempted separation of the active ingredient as the free base from orally administered pharmaceutical product with the intent for injection abuse would require filtrations, toxic solvent removal and multiple extraction procedures including careful pH adjustments to separate the amine free base from the pamoic acid component. Without an involved and technically sophisticated separation, followed by purification, the administration of the drug for the behavioral act of abuse is physically, practically and financially precluded.

Classes of compounds subject to this invention include but are not limited to opiates, morphinoids, tropinoids, amphetamines, compounds containing a pyrrolidine, piperidine or a substituted sub-structure of either or both pyrrolidine and piperidine within the molecule, benzodiazepines, benzazepines, and compounds containing a phenethyl amine or substituted phenethylamine sub-structure within the molecule.

The opiates, or those compounds isolated from opium, or analogous to the principle isolate, morphine, generally serve as narcotic analgesics. Similarly, cocaine, a representative tropinoid, was isolated from coca leaves, and as a class of compounds exhibit anesthetic qualities. Various amphetamines impact processes of the central nervous system and are often employed as stimulants and appetite suppressants (anorexics). The piperidines and pyrrolidines are often employed as useful psychotropic drugs. The benzodiazepines have been employed as antianxiety agents (anxiolytics), as hypnotics and occasionally as muscle relaxants. Clearly, many synthetic and semi-synthetic compounds of each of these classes have been prepared and have shown utility in a broad range of therapeutic ailment administration.

A table of controlled substances is readily available on the United States Drug Enforcement Agency's website at www.DEA.gov. As representative examples, amines from that table which are applicable to the present invention, but without restricting the scope of the invention, include acetorphine, acetylmethadol, allylprodine, alphacetylmethadol, bufotenine, dextromoramide, diethyltryptamine, etorphine, heroin, ibogaine, ketobemidone, lysergic acid diethylamide, mescaline, methaqualone, 3,4-methylenedioxyamphetamine, 3,4-methylenedioxymethamphetamine, N-ethyl-1-phenylcyclohexylamine, peyote, 1-(1-phenylcyclohexyl) pyrrolidine, psilocybin, psilocin, 1-{1-(2-thienyl)-cyclohexyl}-piperidine, alphaprodine, anileridine, cocaine, dextropropoxyphene, diphenoxylate, ethylmorphine, glutethimide, hydrocodone, hydromorphone, levo-alphaaceytlmethadol, levorphanol, meperidine, methadone, morphine, opium, oxycodone, oxymorphone, poppy straw, thebaine, amphetamine, pseudoephedrine, methamphetamine, methylphenidate, phencyclidine, codeine, benzphetamine, ketamine, alprazolam, chlorodiazepoxide, clorazepate, diethylpropion, fenfluramine, flurazepam, halazepam, lorazepam, mazindol, mebutamate, midazolam, oxazepam, pemoline, pentazocine, phentermine prazepam, quazepam, temazepam, triazolam, zolpidem, and buprenorphine. Other amines that receive considerable legal attention are potential and known precursors to methamphetamine, specifically, ephedrine and pseudoephedrine.

The Merck Manual of Diagnosis and Therapy, 18$^{th}$ Edition, published by the Merck Research Laboratories (2006) is an excellent source for cross-referencing the cited drug substances, their derivatives, the various classifications and categories of drug substances, and how these compounds are employed for beneficial medical purposes. It is a legal distinction to classify some drugs substances as "controlled substances" as per the DEA's requirements versus the medical benefits available through administration of a specific drug. Within the context of this invention, the legal distinction does not limit, or impose limitations upon the invention. The invention provides a chemical solution to the societal need for beneficial medications while preventing the aberrant human behavior or intention to incorrectly administer, participate in substance use disorder or to deliberately abuse these drugs. Most controlled substances fall within the following therapeutic categories: anorexics, anxiolytics, analgesics, anesthetics, antihypertensives, anticonvulsants, sedatives, hypnotics and hallucinogens. Of special interest are ephedrine (a bronchodilator) and pseudoephedrine (a decongestant), both of which can serve as suitable precursors to methamphetamine.

The Merck Manual indicates the following opioids have analgesic properties: codeine, hydrocodone, propoxyphene, fentanyl, hydromorphone, levorphanol, meperidine, methadone, morphine, oxycodone, oxymorphone, buprenorphine, butorphanol, nalbuphine, and pentazocine. The Manual further lists classes of non-opioid analgesics also applicable to the present invention and include: indoles, naphthylalkanones, oxicam, para-aminophenol derivatives, fenamates, pyrazaoles, pyrrolo-pyrrolo derivatives, and selective COX-2 inhibitors. Dextromoramide, pentazocine, buprenorphine, alphaprodine phencyclidine, ketobemidone, heroin, allylprodine, acetylmethadol, and anileridine also exhibit analgesic properties.

The Merck Manual also describes several anesthetic compounds to which the current invention is applicable. These compounds include but are not limited to lidocaine, bupivacaine, tetracaine and epinephrine.

Antipsychotic compounds are prone to abuse or deliberate mis-administration. Classes of these compounds listed in the Merck Manual include: phenothiazines, piperidines, piperazines, dibenzoxazepines, dihydroindolones, thioxanthenes, butyrophenones, diphenylbutylpiperidines, dibenzodiazepines, benzisoxazoles, theinobenzodiazepines, dibenzothiazepines, benzisothiazolylpiperazine, and dihydrocarostyrils.

Obesity is often treated with anorexics such as benzphetamine, and similar phenethylamine derivatives, for example, phentermine. Other therapeutic agents for treating obesity include sibutramine, mazindol, diethylpropion and fenfluramine.

With regard to psychiatric disorders, the Merck Manual discusses drug use and the potential for subsequent dependence of: amphetamines, anxiolytics and sedatives (hypnotics), cocaine, gamma hydroxybutyrates, hallucinogens, ketamine, marijuana, methylenedioxymethamphetamine, and opioids. Most interestingly, the Merck Manual states, "Drug abuse is definable only in terms of societal disapproval". The phrase, "substance use disorder" is applied concerning children and adolescents using controlled substances whereas, experimental or recreational use of drugs, while usually illegal, are the terms used for adult use of controlled substances. The amphetamines include amphetamine and methamphetamine. The Manual states, "Methamphetamine is the chief type of amphetamine abuse in North America". Unfortunately, the cough, cold and sinus medications pseudoephedrine and ephedrine have received close commercial scrutiny because of the ability to convert these compounds to methamphetamine. Anxiolytics include the barbiturates and benzodiazepines. The latter category includes drug substances such as alprazolam, lorazepam and triazolam. Other anxiolytics include halazepam, oxazepam, prazepam, diazepam, chlorazepate and chlordiazepoxide. Cocaine can cause euphoric excitement or schizophrenic like symptoms whereas ketamine exhibits anesthetic properties. Methylenedioxymethamphetamine produces a feeling of excitement, disinhibition and accentuates physical sensation.

The Merck Manual reports that learning and developmental disorders are often treated with the controlled substances, methylphenidate or dextroamphetamine.

Compounds included within the sedative or hypnotic therapeutic category include but are not limited to: quazepam, temazepam, triazolam, zolpidem, glutethimide and flurazepam.

Compounds included within the hallucinogenic category include N-ethyl-1-phenylcyclohexylamine, peyote, 1-(1-phenylcyclohexyl)pyrrolidine, psilocybin, psilocin, mescaline, 1-[1-(2-thienyl)-cyclohexyl]piperidine, bufotenine, ibogaine, and lysergic acid diethylamide.

With respect to a specific list of controlled substances, the list is maintained by the DEA and as a legal action occurring through due process of law, compounds may be added to or deleted from the list. In context of this invention, the compounds of interest may be categorized and/or classified according to a number of names as the preceding discussion indicates. Specific compounds will fall within a general class and to that particular class, new derivatives may be synthesized yielding similar therapeutic indications and consequently, the potential for abuse. Additionally, dosage levels of a particular compound may also impact its therapeutic indication. By way of example, midazolam has a therapeutic indication as an anesthetic, anticonvulsant, sedative and hypnotic.

The basic physical and chemical properties of these amines/alkaloids are consistent with amines which receive considerably less attention and which are typically not prone to abuse. It is well understood that the pKa values of the conjugate acid for each amine confirms their ability to produce organic acid addition salts. For comparative purposes between amines, a higher pKa (amine conjugate acid) indicates a lower basicity strength for the amine. Consequently, and by way of example without limiting the scope, the controlled substances listed, demonstrate the fundamental requirement (amine basicity) for producing an organic acid addition salt and indeed, amines having a conjugate acid pKa greater than approximately 1.5 are receptive to pamoate salt formation.

Interestingly, pamoate salts have been shown to exhibit polymorphism as described in U.S. Pat. No. 7,718,649 titled "Physical States of a Pharmaceutical Drug Substance", the disclosure of which is totally incorporated herein by reference. This property of a compound is its ability to solidify in different crystal structures, habits or lattices to yield polymorphs. Indeed, for a drug substance that exhibits polymorphism, different situations may exist: the material may solidify and be isolated from the reaction as 1) an amorphous solid; 2) a single polymorph may be obtained, or 3) a mixture of polymorphs and 4) combinations of the previous three possibilities. Therefore it is important, when polymorphism is suspected, to deliberately attempt to prepare, isolate and characterize the different polymorphs by techniques sufficient to differentiate between amorphous material and individual polymorphs or their mixtures. Often differential scanning calorimetry (DSC) can be employed to identify or monitor the creation of polymorphs. Indeed, when a salt candidate's stability profile can be correlated to a specific polymorph, appropriate synthetic process development activities can define the controlling conditions necessary to yield the single, desired polymorph or some other defined ratio of polymorphs exhibiting an acceptable stability profile.

API salts and their polymorphs often exhibit different dissolution characteristics. For instance the rate of dissolution is pH dependent, and therefore yields a different pharmacokinetic profile and/or therapeutic efficacy. Sometimes, a given drug product formulation expertise or technology can dominate any biological effects the API salt and/or polymorph present. Conversely, drug product formulation and the resulting mechanical properties of a tablet, capsule or bead can be dominated by the physical behavior of the API salt and/or its particular crystal structure. It is not unusual that difficult trade-offs must be made between the ease of manufacture of the drug product and the pharmacokinetics desired.

Drug product formulation can impact the pharmacokinetics of an API salt candidate (and potential polymorph) by a host of technologies, including but not limited to, preparing formulated beads, different sized beads, coated beads, combinations of various bead technologies, formulated matrix systems, addition of hydrophobic layers to tablets, capsules or beads (for example, as a control mechanism to limit the dissolution rate of hydrophilic gelatin capsules), coated tablets and capsules, capsules filled with beads, and different mixtures of beads with different coatings. These formulation techniques make available a wide range of drug product properties including, but not limited to, slow release, controlled release, and extended release drug pharmacokinetics. These activities are dependent upon the API salt selected (and potential polymorph issues) because of the salt's dissolution profile at the pH where drug release is to occur (for liberation of the API from its salt form). In fact, different API salts and formulation techniques can be selected based on where the desired release is to occur in the gastrointestinal tract and the formulator can use the API salt's pKa, solubility, melting point, shape and particle size as primary factors to utilize, moderate or overcome localized insolubility through the use of formulation techniques.

EXPERIMENTAL

Experimental Methods

Differential Scanning Calorimetry

Samples were evaluated using a Differential Scanning calorimeter from TA Instruments (DSC 2010). Prior to analysis of samples, a single-point calibration of the TA Instruments DSC 2010 Differential Scanning calorimeter (DSC 2010) with the element indium as calibration standard (156.6±0.25° C.) was completed.

Infrared Spectroscopy

IR Spectra were obtained in a KBr disc using a Perkin Elmer Spectrum BX Fourier Transform Infrared Spectrophotometer.

Powder X-Ray Diffraction (PXRD)

Powder X-Ray diffraction patterns were acquired on a Scintag XDS2000 powder diffractometer using a copper source and a germanium detector. A powder is defined herein as amorphous if the counts per second of the underlying broad (>2° 2θ at half height) absorption exceeds the counts per second of narrow (<5° 2θ at half height) peaks rising there above. A powder is defined herein as crystalline if the counts per second of the underlying broad (>20° 2θ at half height) absorption is less than the counts per second of narrow (<5° 2θ at half height) peaks rising there above. Crystalline and polycrystalline are not distinguished herein. Crystalline materials are defined as having a morphology even if the actual morphology is not elucidated. Polycrystalline materials are defined as being polymorphic.

High Pressure Liquid Chromatography (HPLC)

HPLC analyses were performed on a Waters 2695 HPLC system equipped with a Waters 2996 photo diode array detector.

$^1$H NMR Spectroscopy $^1$H NMR spectra were obtained on a 300 MHz Varian Gemini 2000 spectrometer. Spectra were referenced to solvent (DMSO-$d_6$).

Dissolution

Dissolution testing was performed using a Distek Dissolution System 2100 consisting of six 1000 mL dissolution vessels with covers containing sampling ports, six stainless steel paddles and spindles, RPM control unit, and a Distek TCS0200C Water Bath, Temperature Controller Unit.

EXAMPLES

Example 1

Preparation of Phentermine Pamoate

Figure 4:
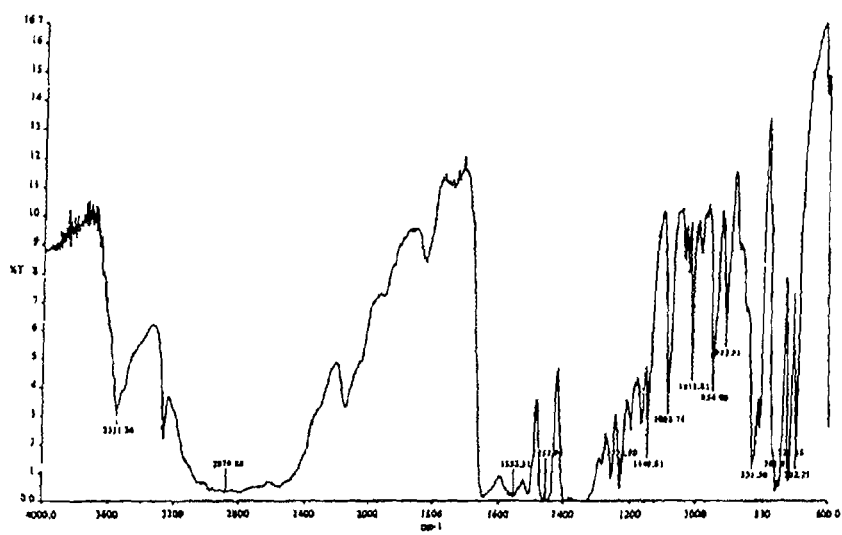
FIG. 4 is an FTIR spectrum phentermine pamoate.
Figure 7:
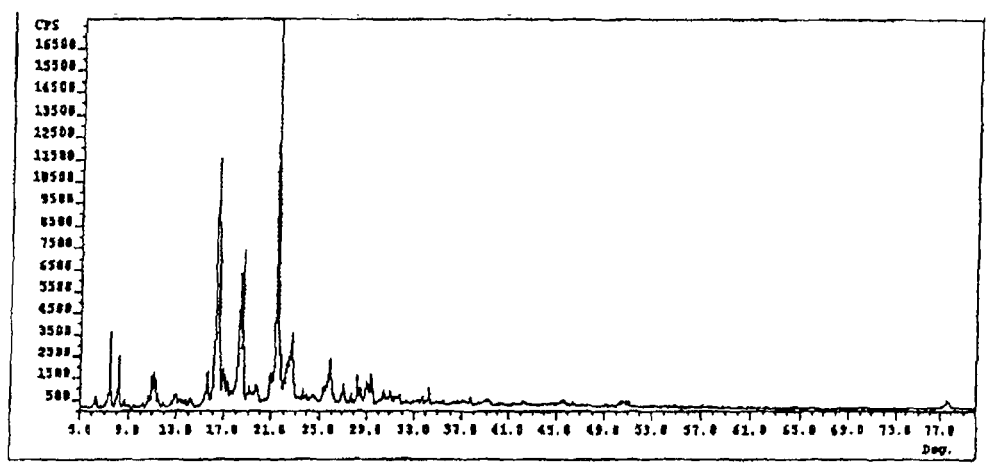
FIG. 7 is an PXRD diffractogram of phentermine pamoate.

Phentermine HCl (37.3 g) was suspended in USP $H_2O$ (700.0 g) and stirred to achieve a solution (0.05 g/g) and a pH 5.3. The solution was transferred to a metered addition funnel. A solution of disodium pamoate (45.0 g) was prepared by dissolving in USP water (902.0 g) to give a clear solution at a pH 10.4. The solution was adjusted to about pH 9.4 with 0.2N HCl and clarified by solution filtration. At 20° C., the Phentermine HCl solution was added to the stirred disodium pamoate solution at a controlled rate over about 2.5 hours and the addition funnel rinsed with USP H₂O (20.0 g) into the reaction mixture. The mixture was stirred for 1 h then warmed to 70° C. where more precipitation was observed. The mixture was heated from about 70° C. to 95° C. over about 1 h then cooled. Solids were collected by filtration and washed with USP H₂O (3×200 g) and dried on a vacuum Büchner for about 3 h. The solids collected (83.5 g) were transferred to a drying oven (50-55° C., vacuum/N₂ sweep) and dried about 48 h to give Phentermine Pamoate (64.7 g, 94.2%). The pamoate was characterized by DSC (FIG. 1), FTIR (FIG. 4) and PXRD (FIG. 7).

Example 2

Preparation of Ephedrine Pamoate

Ephedrine Hydrochloride (6.1 g) was stirred in USP water (45.0 g) to yield a solution pH of about 4.9. In a separate flask a disodium pamoate (6.5 g) solution was prepared using USP water (54.0 g) to yield a solution pH of about 9.5. The ephedrine HCl solution was transferred to a metered addition funnel and added to the disodium pamoate solution over approximately 1 h. When about one-half of the addition was completed, the solution became opaque. USP water (2.6 g) was used to rinse in the residue from the addition funnel. The opaque mixture was heated from about 26° C. to near 80° C. The reaction was stirred at about 80° C. for approximately 4.5 h. A thick residue settled in the reaction vessel as the solution cooled. The solution was decanted and the residue transferred to drying dishes. The residue was dried at about 100° C. under vacuum (nitrogen sweep) for about 5.5 h. Drying was continued for about 66 h, the solid ground with a mortar and pestle to give a dense powder (4.2 g, 39%). and a DSC analysis indicated a clear melt ($T_{max}$ 243.4° C., $T_{onset}$ 227.7° C., and heat of fusion 142.2 J/g).

Example 3

Alternate Preparation of Ephedrine Pamoate

Figure 2:
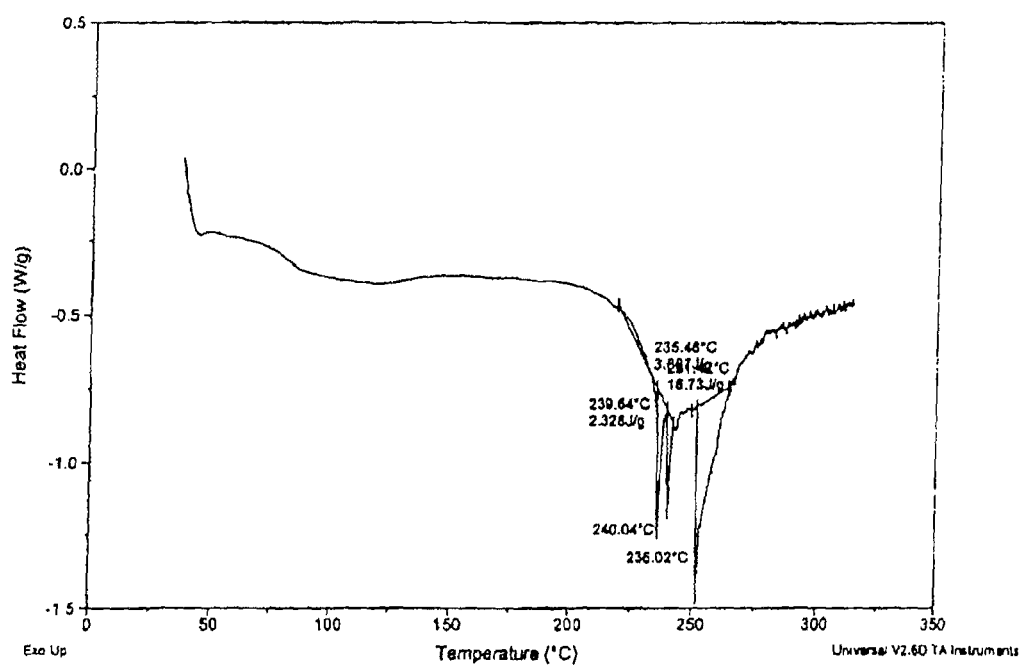
FIG. 2 is an DSC thermogram of ephedrine pamoate.
Figure 5:
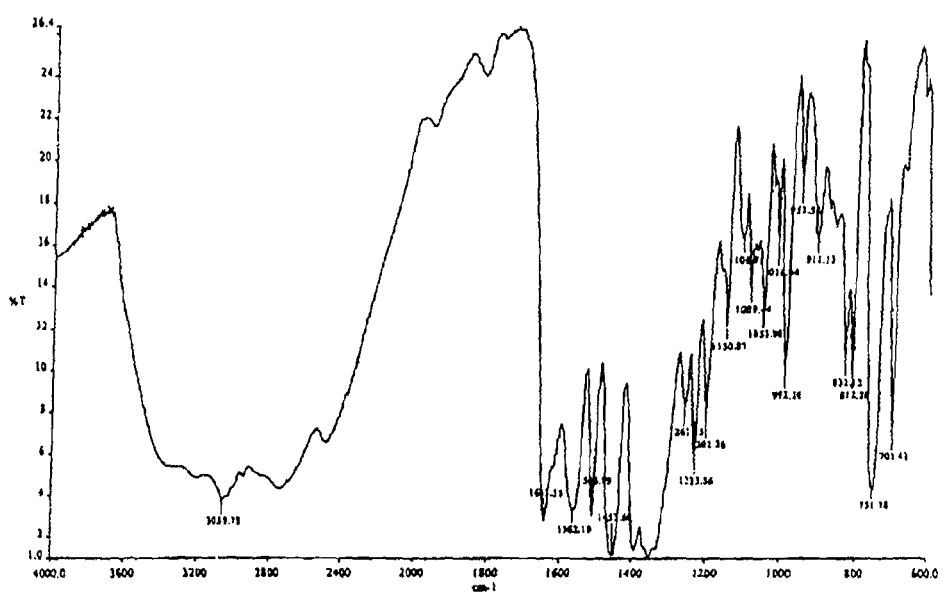
FIG. 5 is an FTIR spectrum of ephedrine pamoate.
Figure 8:
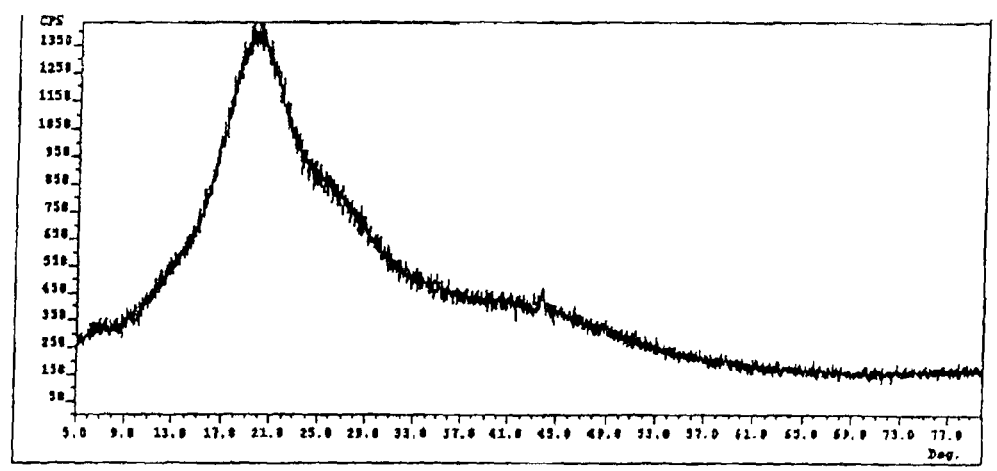
FIG. 8 is an PXRD diffractogram of ephedrine pamoate.

Ephedrine Hydrochloride (7.1 g) was stirred in methanol (62.6 g). Disodium pamoate (8.0 g) was stirred in USP water (71.0 g) and adjusted to about pH 9.5. The methanolic ephedrine hydrochloride solution was added to the disodium pamoate solution over a period of about 1.75 h. The reaction solution was heated to about 60° C. for around 4.5 h then cooled. The reactor was equipped with a distillation head and aqueous methanol was removed by heating. The opaque mixture was cooled and a residue settled to the bottom of the reaction vessel. The solution was carefully decanted and the residue was transferred to a drying dish. The material was placed in a vacuum drying oven (103° C.) for 24 h with a nitrogen sweep. Ephedrine Pamoate was obtained as a solid, 8.4 g (66.6%) 2:1 ephedrine pamoate (by HPLC assay) and characterized by DSC (FIG. 2), FTIR (FIG. 5) and PXRD (FIG. 8).

Example 4

Preparation of Pseudoephedrine Pamoate

Figure 3:
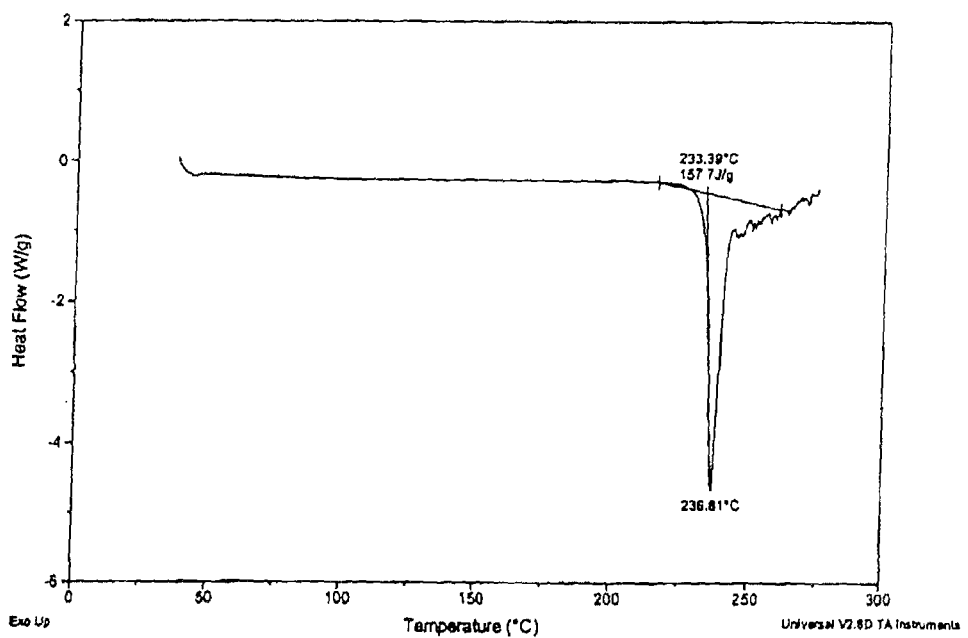
FIG. 3 is an DSC thermogram of pseudoephedrine pamoate.
Figure 6:
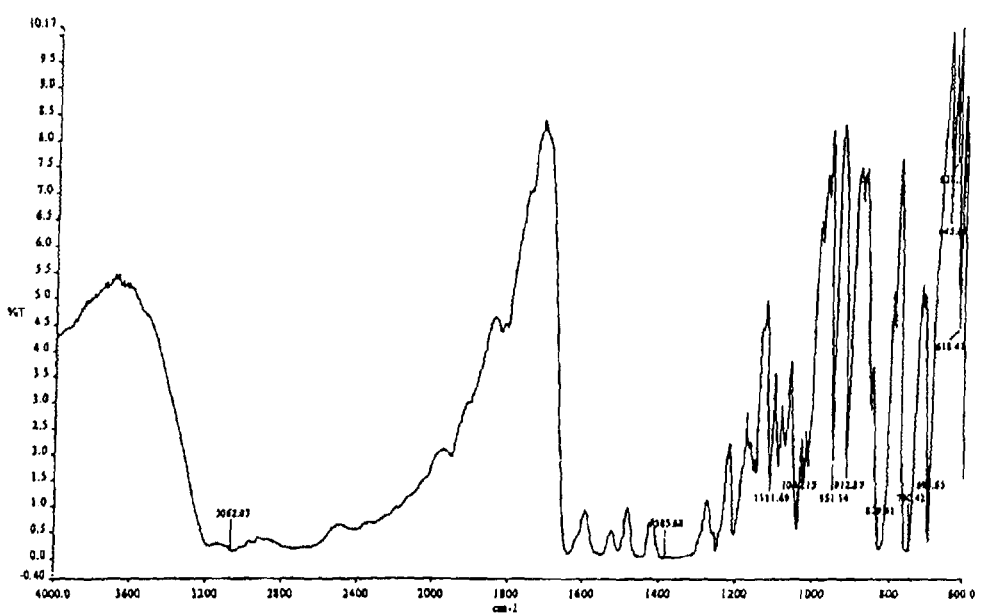
FIG. 6 is an FTIR spectrum of pseudoephedrine pamoate.
Figure 9:
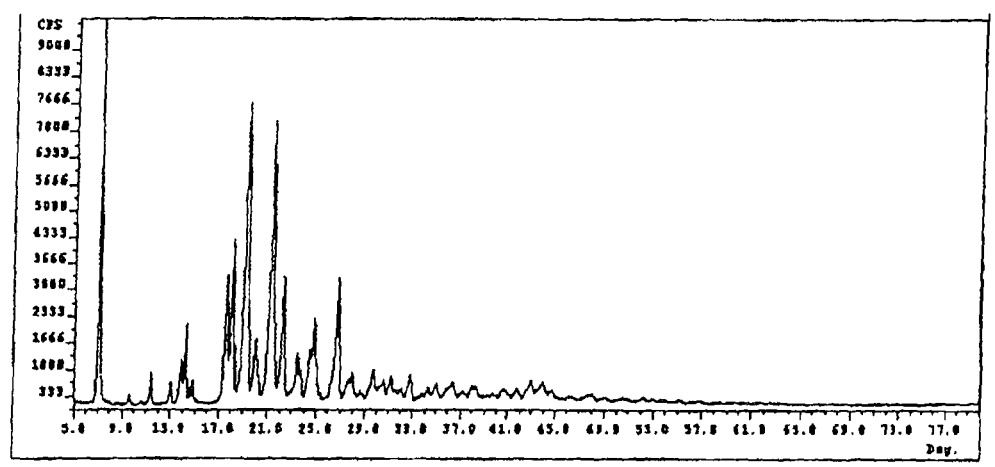
FIG. 9 is an PXRD diffractogram of pseudoephedrine pamaote.

Disodium pamoate (10.4 g) was dissolved in USP water (73.5 g) and filtered to clarify. The filtrate was returned to a rinsed reactor employing a water rinse (15 g). The solution of disodium pamoate exhibited a pH of about 9.5. Pseudoephedrine HCl (9.3 g) in USP water (53.1 g) was prepared and exhibited a pH of about 6.3. The pseudoephedrine HCl solution was added to the disodium pamoate solution. As the addition continued, the oily mixture became opaque. After complete addition (~1 h), the residue in the addition funnel was rinsed into the reaction vessel with USP water (5.0 g). The mixture was heated at about 84° C. for approximately 3.25 h. The mixture was then cooled overnight and solids were collected by filtration. The filter cake was washed with USP water (3×30 g) and dried in a vacuum oven (98-102° C.) for about 5.2 h with a nitrogen sweep. After cooling, the finely powdered 2:1 (by HPLC) pseudoephedrine pamoate solids (15.9 g, 87%) was characterized by DSC (FIG. 3), FTIR (FIG. 6) and PXRD (FIG. 9).

Example 5

Preparation of Benzphetamine Pamoate

Figure 10:
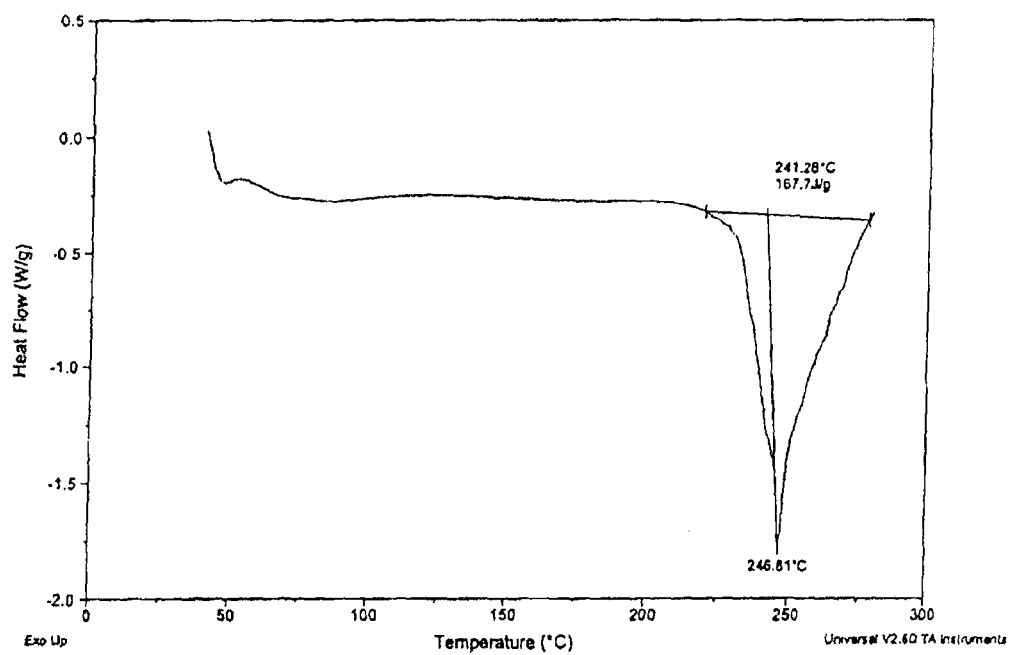
FIG. 10 is an DSC thermogram of benzphetamine pamoate.
Figure 11:
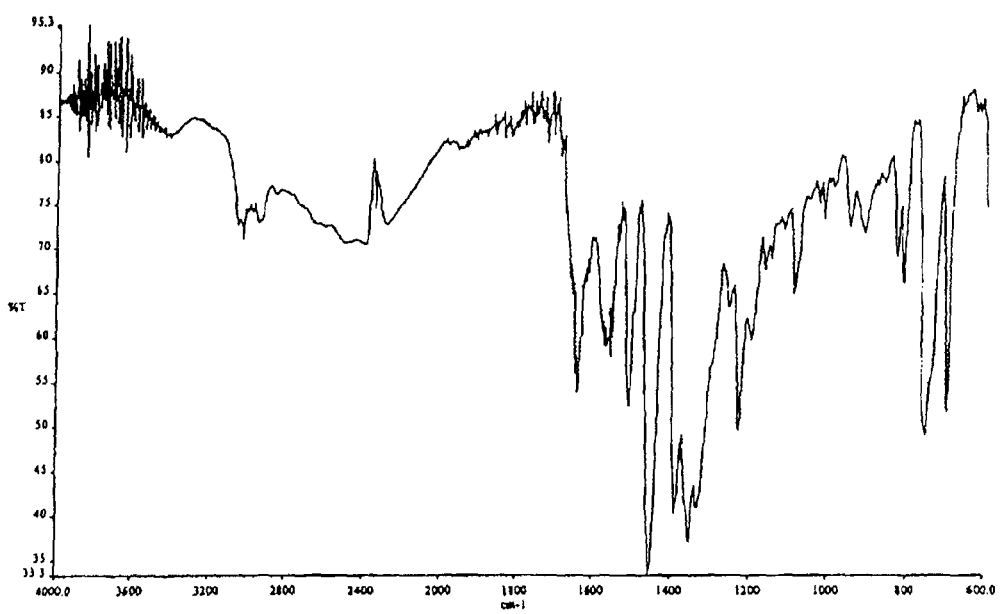
FIG. 11 is an FTIR spectrum benzphetamine pamoate.
Figure 12:
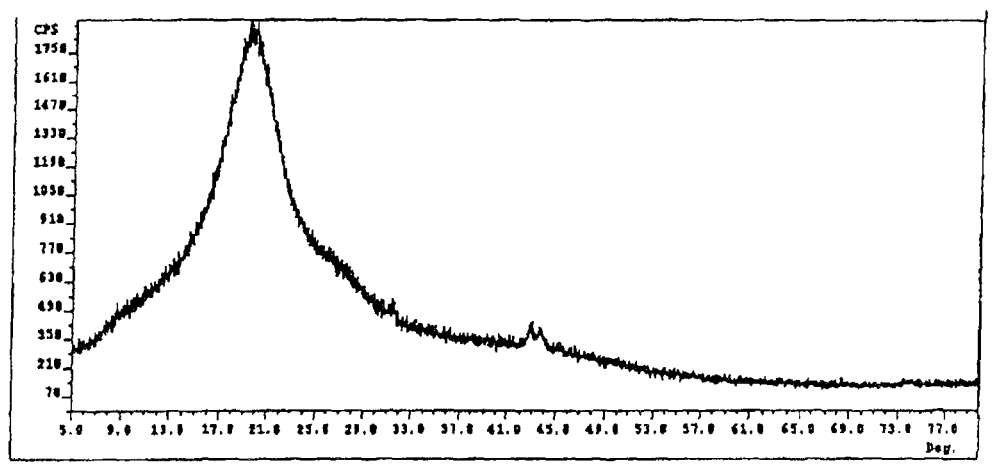
FIG. 12 is an PXRD diffractogram of benzphetamine pamoate.

To a solution containing disodium pamoate (19.1 g) in water (218.0 g) was added as needed dilute HCl or NaOH solution to adjust the solution to about pH 9.4. To a second solution of benzphetamine HCl (24.3 g) in water (211.0 g) was added dilute HCl or NaOH solution to adjust the solution to about pH 4.5. The benzphetamine HCl solution was added to the disodium pamoate solution over a period of about 3 h. The mixture was stirred and held at about 53° C. for at least 18 h. The mixture was cooled to below 25° C. and the solids were collected by filtration. The solid cake was washed with USP purified water. The wet cake was dried at 70° C. under reduced pressure to yield a solid (30.0 g). The 2:1 benzphetamine pamoate by HPLC assay was characterized by DSC (FIG. 10), FTIR (FIG. 11) and PXRD (FIG. 12).

Example 6

Solubility Recovery Comparison of Selected Amine Salts

A comparison of pseudoephedrine as its pamoate salt and as it hydrochloride was performed at 37° C. Each salt was tested for its solubility recovery at pH 4.5 and pH 7.0. For comparison equivalency, the amount of pamoate salt was adjusted to account for the molecular weight difference between the pamoate and the hydrochloride such that equal amounts of pseudoephedrine were compared at each pH condition.

A flask containing USP H₂O (10.0 mL at pH 4.5 having used HCl to adjust) was warmed to 37° C.±2° C. in a water bath. Pseudoephedrine HCl (1.0 g) was added to the solution at 37° C.±2° C. A visual observation indicated the immediate dissolution of about ⅔ of the bulk solids. Magnetic stirring was initiated and a solution was observed. The solution was stirred for 31 min then filtered. No solids were collected and flask was rinsed to the filter with USP H₂O (pH 4.5) (2×5.0 g). Pseudoephedrine HCl was completely soluble at pH 4.5.

In a second flask containing USP H₂O (10.0 mL at pH 4.5 having used HCl to adjust) was warmed to 37° C.±2° C. in a water bath. Pseudoephedrine pamoate (1.8 g) was added to the solution. The pamoate salt, as a solid, floated on top of the water and did not wet. Magnetic stirring was initiated and some solids were pulled below the surface and stirred. Approximately ½-⅔ of the solids remained above the water surface and the thermometer was used to push the remaining solids below the water surface. A bi-phasic mixture was observed which was stirred for 32 min and then filtered to collect the solids. The flask contents were rinsed to the filter with USP H₂O (pH 4.5) (3×5.0 g). The solids were dried under vacuum then transferred to a drying pan and into a vacuum oven (80±2° C.) under N₂. After 19.75 h, the solids were removed to cool and weighed yielding a mass recovery of peudoephedrine pamoate (1.76 g) (98%).

Pseudoephedrine pamoate was insoluble at pH 4.5.

A similar set of experiments was conducted whereby a flask containing USP H₂O (10.0 mL at pH 7.0 having used HCl and NaOH to adjust) was warmed to 37° C.±2° C. in a water bath. Pseudoephedrine HCl (1.02 g) was added to the solution at 37° C.±2° C. A visual observation indicated the immediate dissolution of about ⅔ of the bulk solids. Magnetic stirring was initiated and a solution was observed. The solution was stirred for 31 min then filtered. No solids were collected and flask was rinsed to the filter with USP H₂O (pH 7.0) (2×5.0 g). Pseudoephedrine HCl was completely soluble at pH 7.0.

In a second flask containing USP H₂O (10.0 mL at pH 7.0 having used HCl and NaOH to adjust) was warmed to 37° C.±2° C. in a water bath. Pseudoephedrine pamoate (1.80 g) was added to the solution. The solid pseudoephedrine pamoate floated on top of the water and did not wet. Magnetic stirring was initiated and some solids were pulled below the surface and stirred. Approximately ½-⅔ of the solids remained above the water surface and the thermometer was used to push the remaining solids below the water surface. A bi-phasic mixture was observed. The mixture was stirred for 31 min and then vacuum filtered to collect the solids. The flask contents were rinsed to the filter with USP H₂O (pH 7.0) (3×5 g). The solids were dried under vacuum then transferred to a drying pan and into a vacuum oven (80±2° C.) under N₂. After 14.75 h, the solids were removed to cool and weighed to yield a mass recovery of pseudoephedrine pamoate (1.76 g) (98%). Pseudoephedrine pamoate was insoluble at pH 7.0.

In a similar fashion, the recovery solubility comparisons were performed on benzphetamine, ephedrine, phentermine and imipramine as their hydrochloride and pamoate salts at the two pH conditions of 4.5 and 7.0 at 37° C. Imipramine xinafoate and salicylate were also tested under these conditions. The results from each of these comparative studies are summarized in the table below. It was consistently observed that the hydrochloride salt yielded a complete solution whereas the pamoate, xinafoate and salicylate within experimental error of handling and recovery manipulations, demonstrated insolubility at pH 4.5 and 7.0.

| Drug | pH | % Recovery |
| --- | --- | --- |
| Phentermine Pamoate | 4.5 | 98.4 |
| Phentermine HCl | 4.5 | 0 |
| Phentermine Pamoate | 7.0 | 97.3 |
| Phentermine HCl | 7.0 | 0 |
| Ephedrine Pamoate | 4.5 | 94.4 |
| Ephedrine HCl | 4.5 | 0 |
| Ephedrine Pamoate | 7.0 | 94.4 |
| Ephedrine HCl | 7.0 | 0 |
| Pseudoephedrine Pamoate | 4.5 | 98.9 |
| Pseudoephedrine HCl | 4.5 | 0 |
| Pseudoephedrine Pamoate | 7.0 | 97.8 |
| Pseudoephedrine HCl | 7.0 | 0 |
| Benzphetamine Pamoate | 4.5 | 91.1 |
| Benzphetamine HCl | 4.5 | 0 |
| Benzphetamine Pamoate | 7.0 | 92.7 |
| Benzphetamine HCl | 7.0 | 0 |
| Imipramine HCl | 4.5 | 0 |
| Imipramine Xinaforate | 4.5 | 97.0 |
| Imipramine Salicylate | 4.5 | 104 |
| Imipramine HCl | 7.0 | 0 |
| Imipramine Xinafoate | 7.0 | 97.0 |
| Imipramine Salicylate | 7.0 | 104 |

Example 7

Preparation of Imipramine Xinafoate

Figure 13:
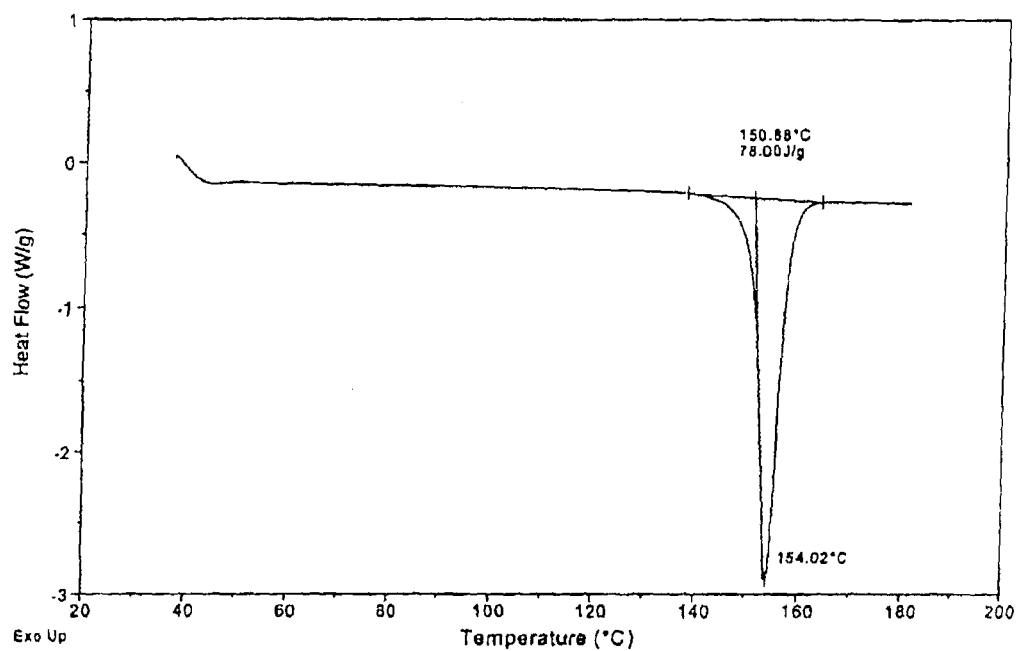
FIG. 13 is an DSC thermogram of imipramine xinafoate.
Figure 14:
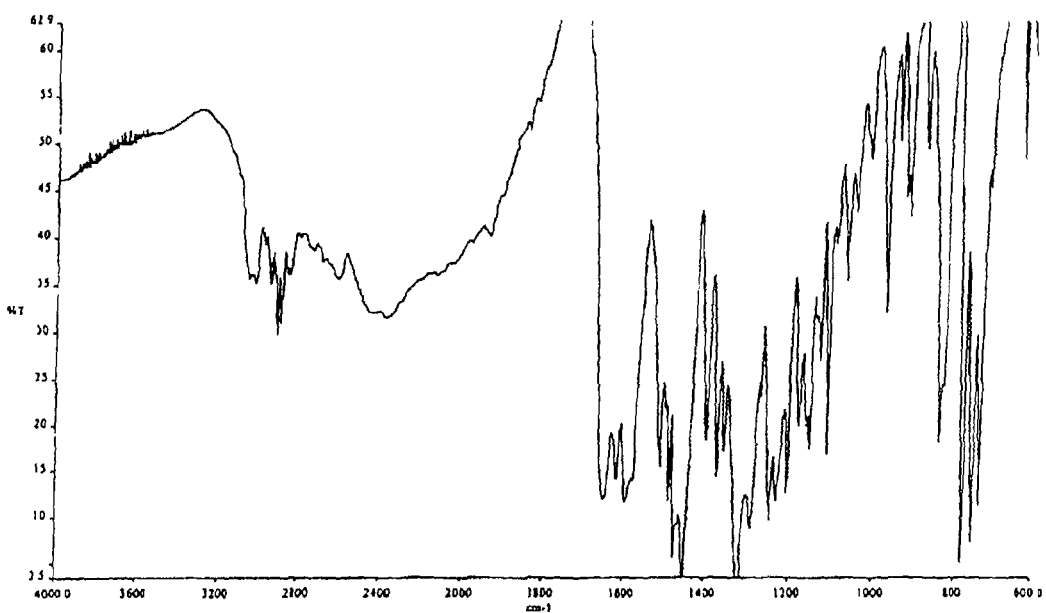
FIG. 14 is an FTIR spectrum of imipramine xinafoate.
Figure 15:
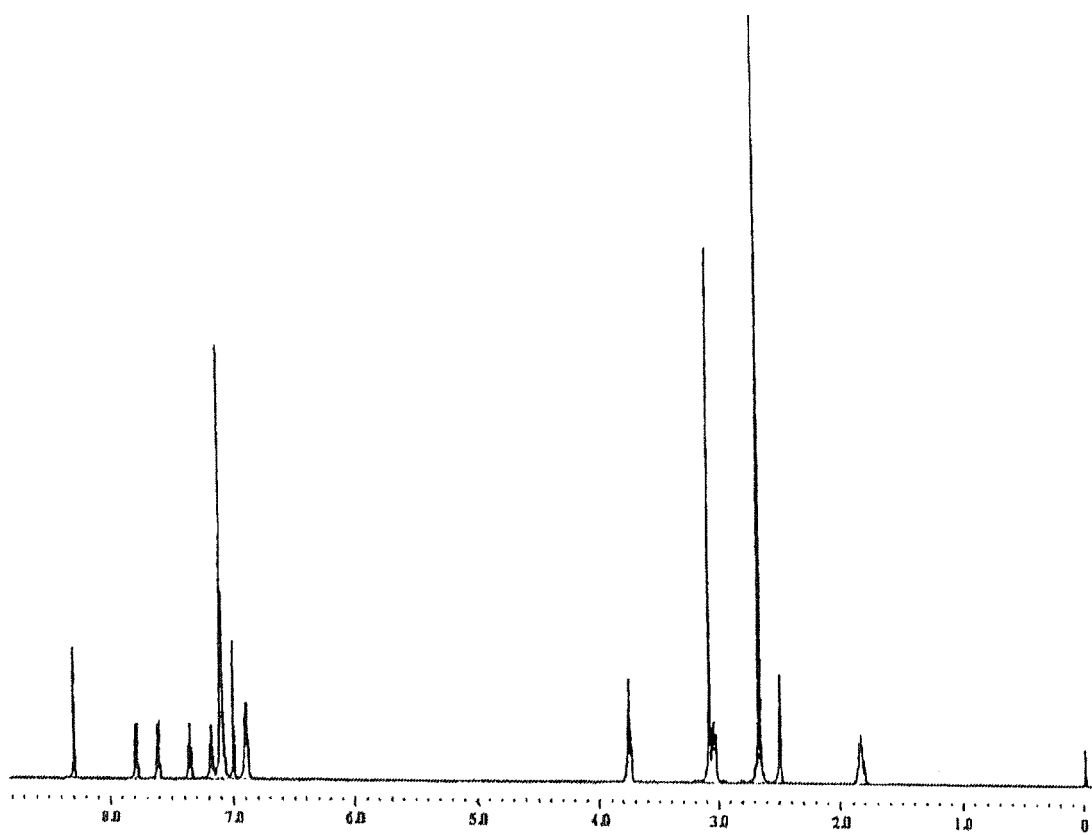
FIG. 15 is an $^1$H NMR spectrum of imipramine xinafoate.
Figure 16:
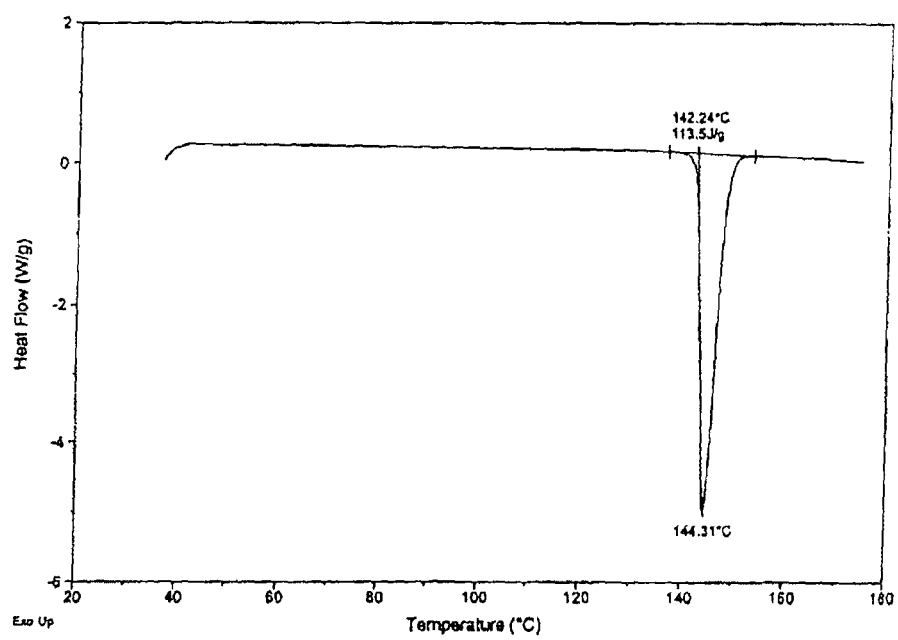
FIG. 16 is an DSC thermogram of imipramine salicylate.
Figure 17:
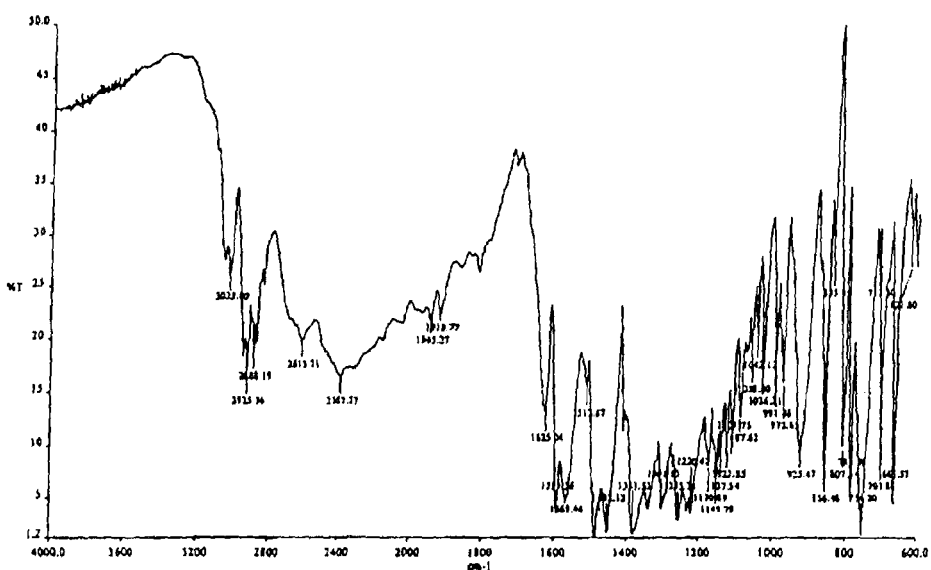
FIG. 17 is an FTIR spectrum of imipramine salicylate.
Figure 18:
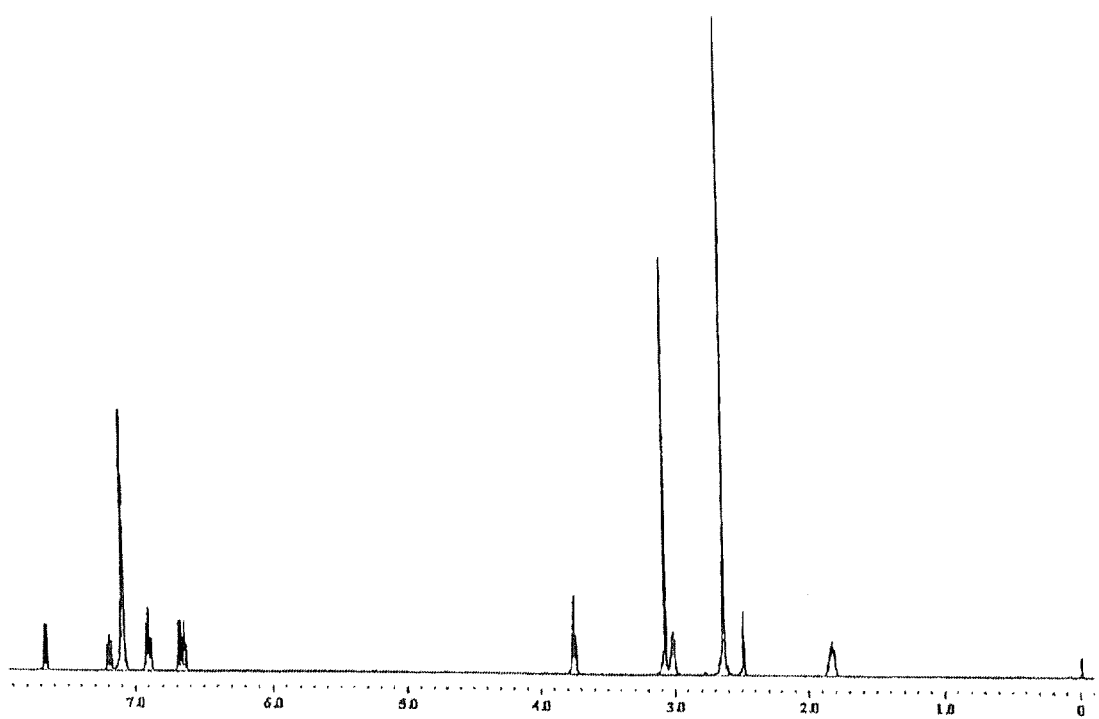
FIG. 18 is an $^1$H NMR spectrum of imipramine salicylate.
Figure 19:
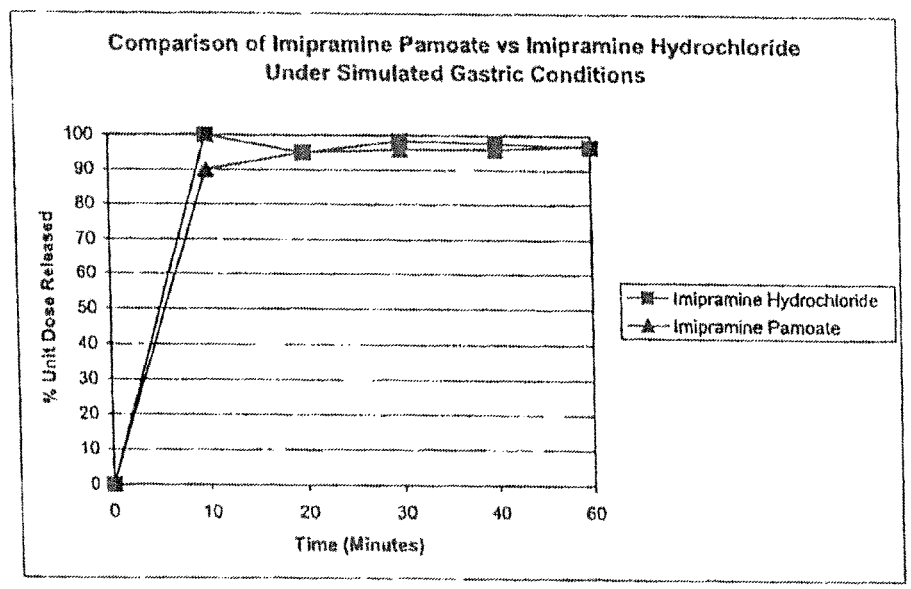
FIG. 19 is a graphical presentation of the dissolution profile comparison of imipramine pamoate vs. imipramine hydrochloride under simulated gastric conditions.
Figure 20:
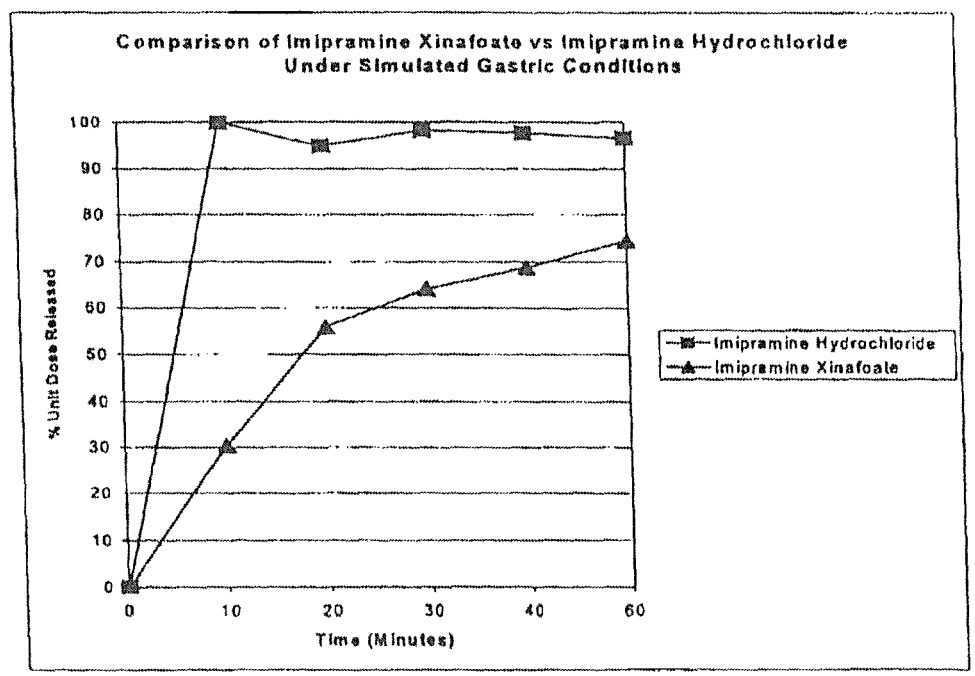
FIG. 20 is a graphical presentation of the dissolution profile comparison of imipramine xinafoate vs. imipramine hydrochloride under simulated gastric conditions.
Figure 21:
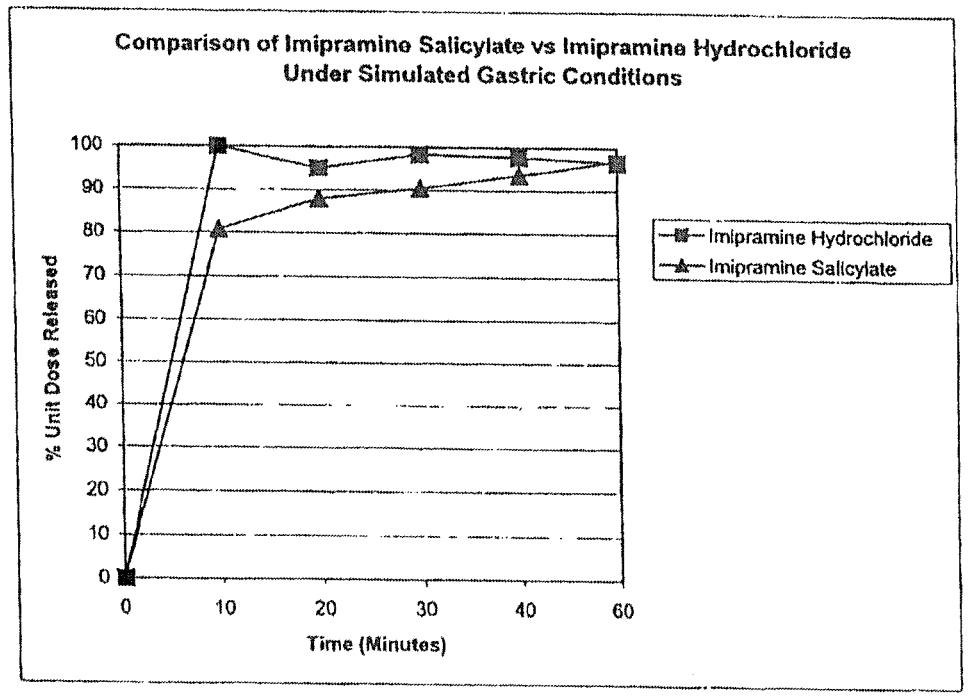
FIG. 21 is a graphical presentation of the dissolution profile comparison of imipramine salicylate vs. imipramine hydrochloride under simulated gastric conditions.
Figure 22:
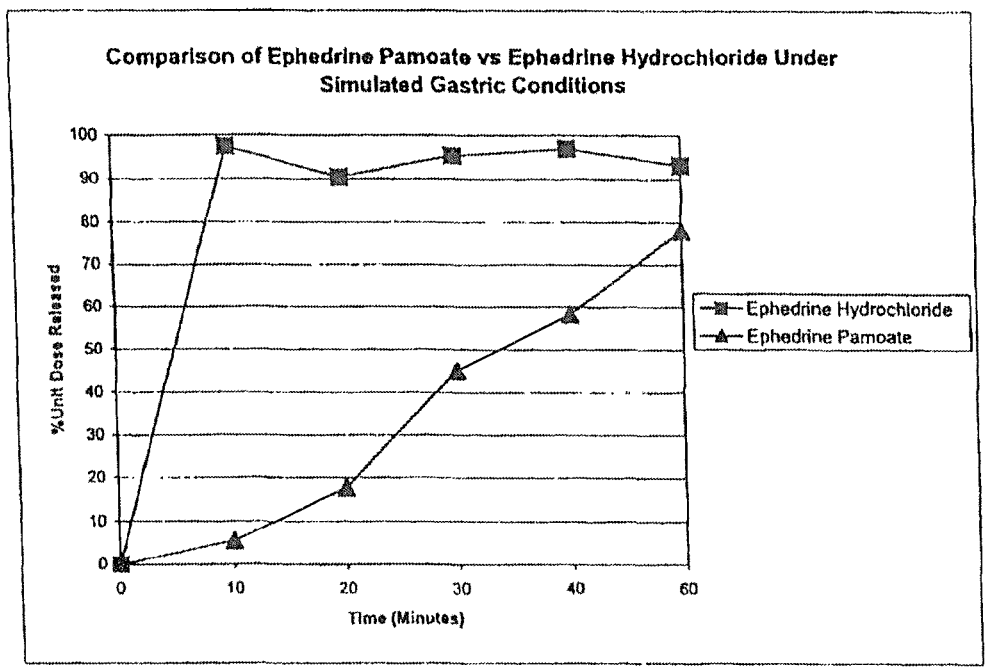
FIG. 22 is a graphical presentation of the dissolution profile comparison of ephedrine pamoate vs. ephedrine hydrochloride under simulated gastric conditions.
Figure 23:
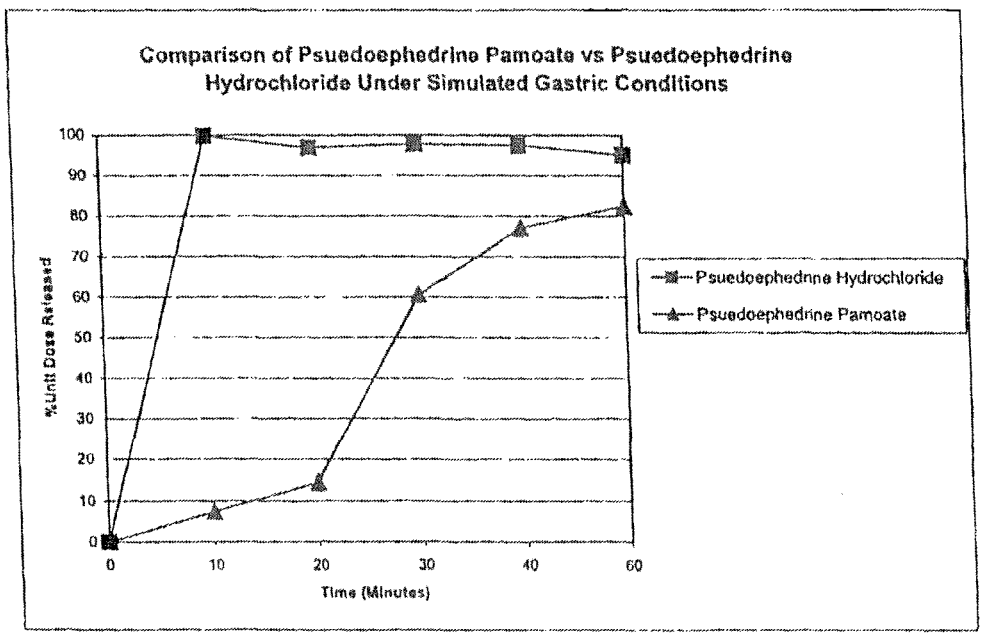
FIG. 23 is a graphical presentation of the dissolution profile comparison of pseudoephedrine pamoate vs pseudoephedrine hydrochloride under simulated gastric conditions.
Figure 24:
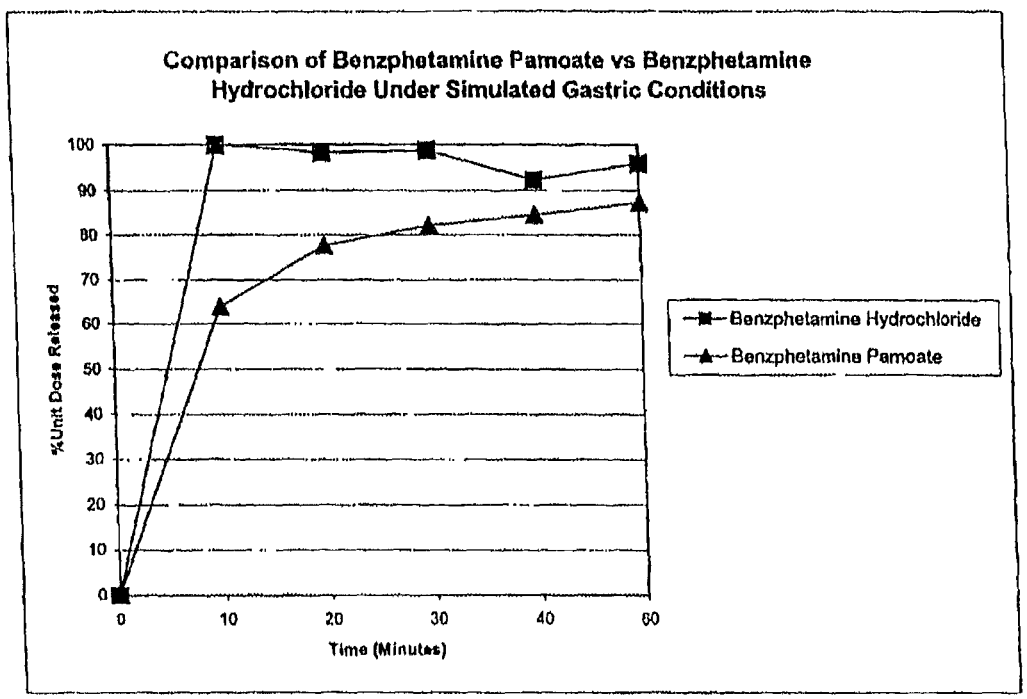
FIG. 24 is a graphical presentation of the dissolution profile comparison of benzphetamine pamoate vs. benzphetamine hydrochloride under simulated gastric conditions.
Figure 25:
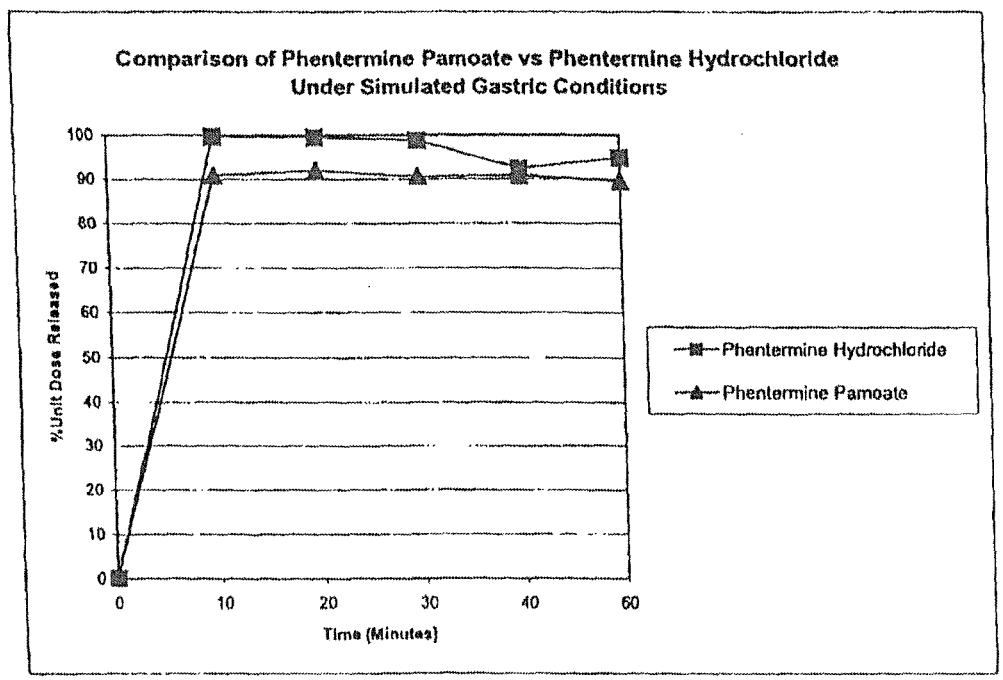
FIG. 25 is a graphical presentation of the dissolution profile comparison of phentermine pamoate vs. phentermine hydrochloride under simulated gastric conditions.
Figure 26:
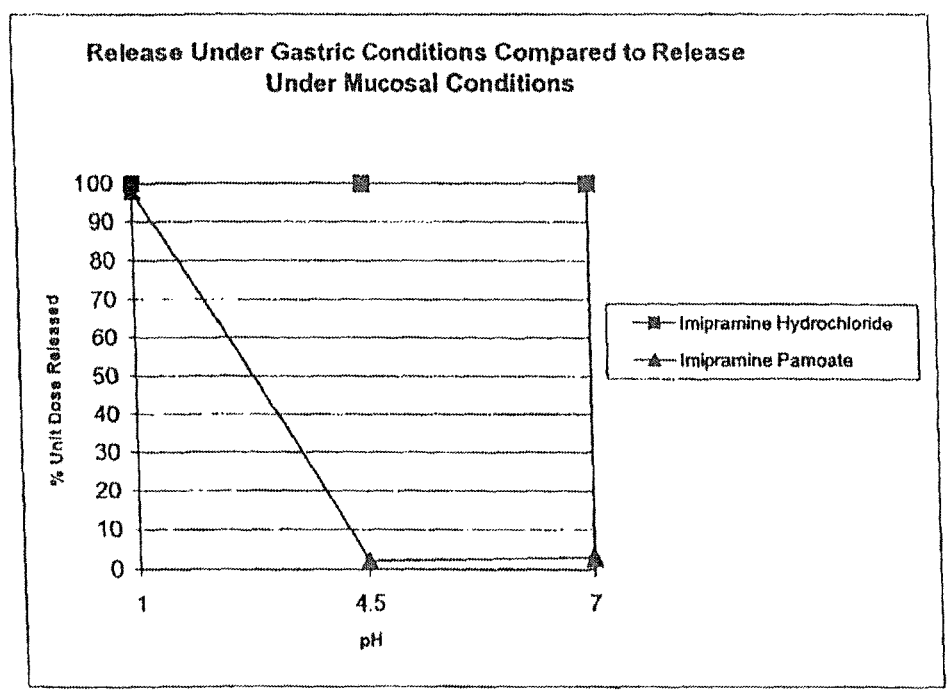
FIG. 26 is a graphical presentation of the release profile of imipramine hydrochloride vs. imipramine pamoate under gastric conditions compared to release under mucosal conditions.
Figure 27:
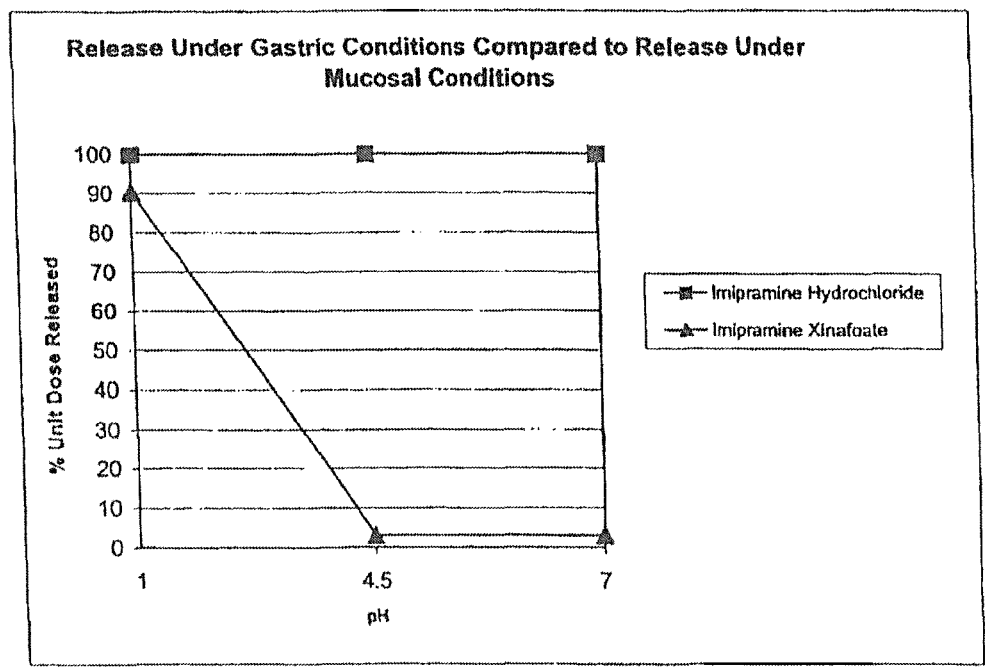
FIG. 27 is a graphical presentation of the release profile of imipramine hydrochloride vs. imipramine xinafoate under gastric conditions compared to release under mucosal conditions.
Figure 28:
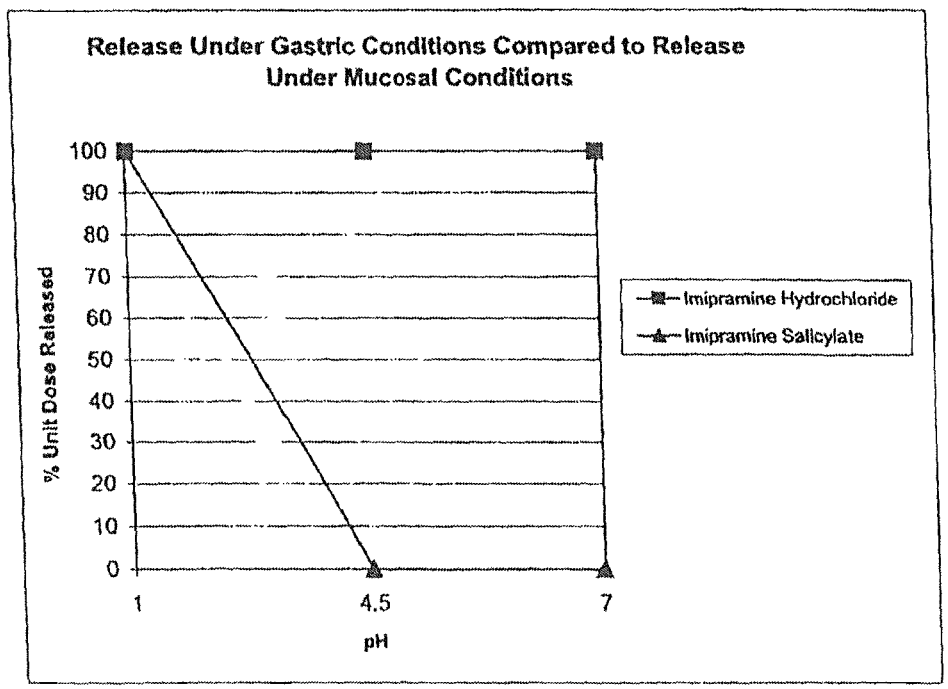
FIG. 28 is a graphical presentation of the release profile of imipramine hydrochloride vs. imipramine salicylate under gastric conditions compared to release under mucosal conditions.
Figure 29:
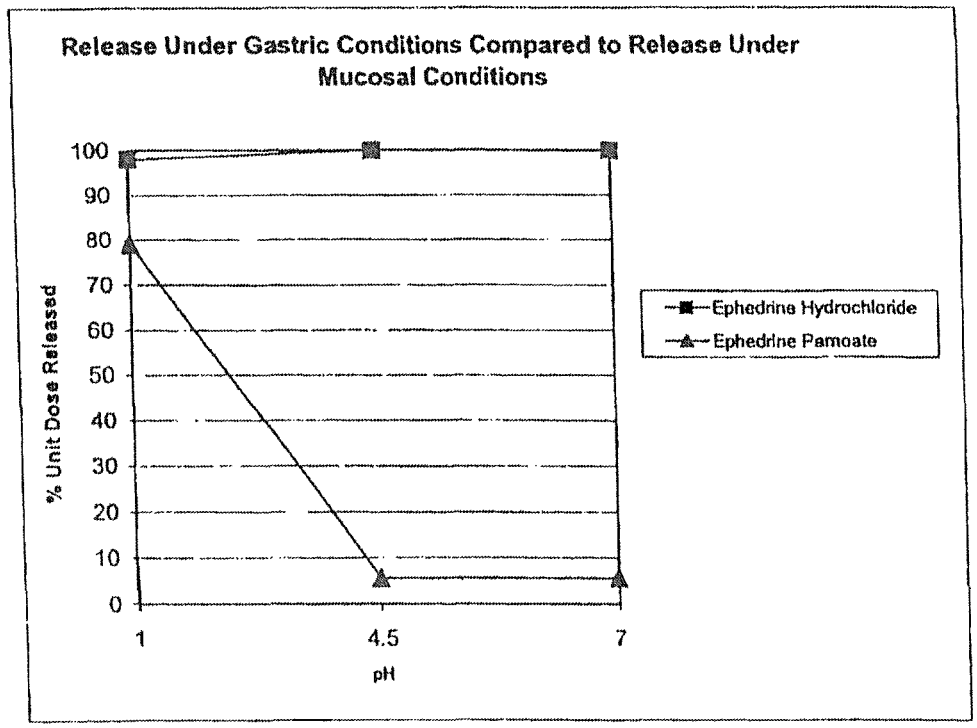
FIG. 29 is a graphical presentation of the release profile of ephedrine hydrochloride vs. ephedrine pamoate under gastric conditions compared to release under mucosal conditions.
Figure 30:
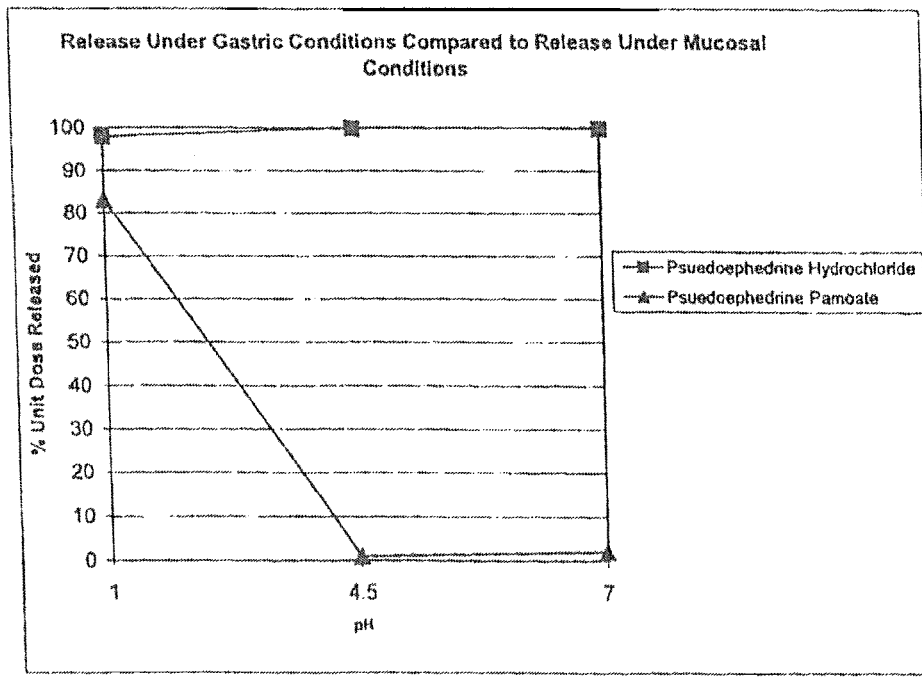
FIG. 30 is a graphical presentation of the release profile of pseudoephedrine hydrochloride vs. pseudoephedrine pamoate under gastric conditions compared to release under mucosal conditions.
Figure 31:
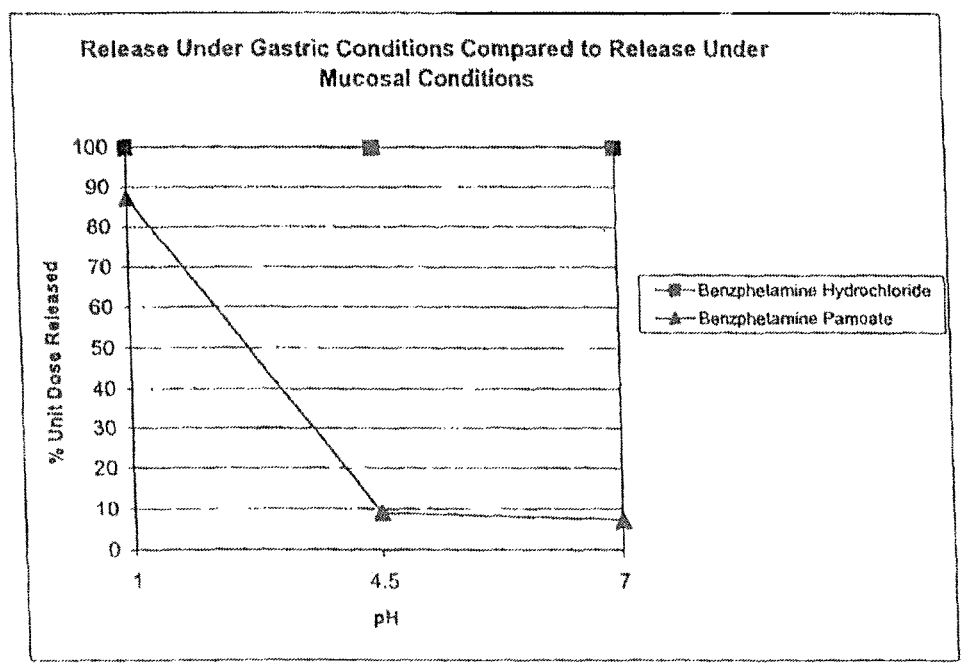
FIG. 31 is a graphical presentation of the release profile of benzphetamine hydrochloride vs. benzphetamine pamoate under gastric conditions compared to release under mucosal conditions.
Figure 32:
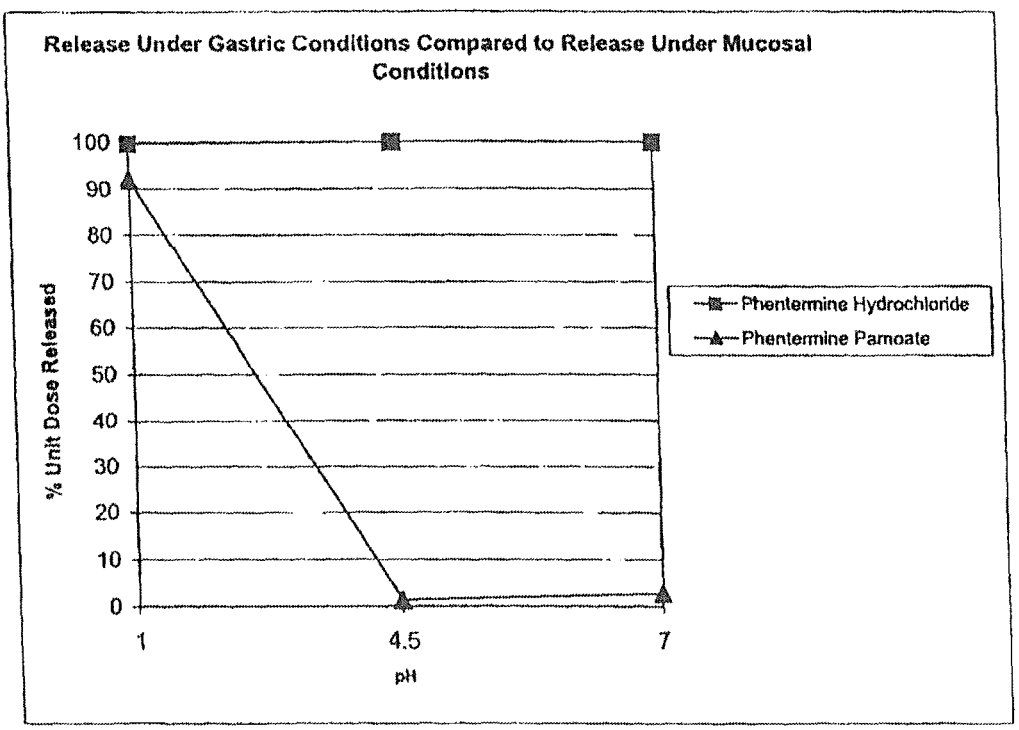
FIG. 32 is a graphical presentation of the release profile of phentermine hydrochloride vs. phentermine pamoate under gastric conditions compared to release under mucosal conditions.

To a solution containing 7.7 g of 3-hydroxy-2-napthoic acid in 75.0 g of USP water was added as necessary dilute HCl or NaOH solution to adjust the solution to about pH 9.4. To a second solution of 13.6 g of imipramine HCl in 100.0 g of USP water was added as necessary dilute HCl or NaOH solution to adjust the solution to about pH 4.5. The imipramine HCl solution was added to the 3-hydroxy-2-napthoic sodium salt solution over a period of about 2 h. The mixture was stirred and held at around 50° C. for at least 18 h. The mixture was cooled to below 25° C. and the solids were collected by filtration. The solid cake was washed with USP water (2×100 g). The solid cake was dried at 105° C. under vacuum to yield a powder (12.7 g) and characterized by DSC (FIG. 13), FTIR (FIG. 14) and ¹H NMR (FIG. 15).

Example 8

Preparation of Imipramine Salicylate

Sodium Salicylate (16.4 g) in USP water (118.0 g) was stirred at 20° C. in a 1 L reactor. After 15 min, the solution was checked and exhibited pH 6.23. In a Imipramine HCl (31.7 g) in USP water (320.0 g) was stirred at 22° C. in a 500 mL reactor until a solution was observed (>20 min). The Imipramine HCl solution was checked and exhibited a pH 4.54. The Imipramine HCl solution was added via metered addition funnel to the sodium salicylate solution at 20° C. over 1.75 h. The reactor and addition funnel was rinsed to the reaction with USP water (20.0 g). The reaction mixture was heated from about 20° C. to about 50° C. for 1.2 h. The mixture was heated to about 62° C. for 17 h. Solids were collected by filtration of the mixture at 50° C. Residue was rinsed from the reactor to the filter with USP water (4×110.0 g). After drying on the filter for 1 h, solids were dried at about 65° C. to about 78° C. for approximately a day. Imipramine salicylate, mp 141-143.6° C. (39.8 g, 95.1%). Recrystallization of imipramine salicylate from a solution of ethanol-water (98/2) provided solid, mp 142.2-144.2° C. The DSC thermogram (FIG. 16), FTIR analysis (FIG. 17) and ¹H NMR spectra (FIG. 18) were consistent with the expected structure.

Example 9

Dissolution Testing Procedure

Dissolution testing was performed according to the FDA's Guidance for Industry document entitled, "Waiver of In Vivo Bioavailability and Bioequivalence Studies for Immediate-Release Solid Oral Dosage Forms Based on a Biopharmaceutics Classification System and following the recommendations under section III C titled "Determining Drug Product Dissolution Characteristics and Dissolution Profile Similarity". A comparison dissolution test was performed for each active ingredient's hydrochloride salt versus its pamoate salt with concentrations adjusted for molecular weight differences. This adjustment provided an equal concentration of active ingredient (calculated as the free base) for both the hydrochloride and pamoate salts. A similar calculation and charge adjustment was performed in the case of xinafoate and salicylate salt comparisons to the corresponding hydrochloride salt.

The Distek Dissolution System was arranged in an Apparatus II configuration as per United States Pharmacopeia dissolution testing procedure USP <711> employing paddles and a 50 RPM spindle speed. The water bath temperature was set and controlled at 37±1° C.

The dissolution tests on drug hydrochlorides and the drug pamoates, xinafoate, and salicylate were performed as separate experimental sets. Each experimental set was subjected to simulated gastric conditions by employing a standardized (and traceable) buffered 0.1N HCl solution supplied by VWR.

Each test sample was filled into a clear gelatin capsule (Capsuline Size "2"). The pharmaceutical grade gelatin capsules are derived from bovine raw materials from BSE-free countries. The gelatin is 100% HIDE gelatin. A wire (~1.7-2.0 g) was coiled around each capsule to assure the capsule did not float in the test medium. The amount of each API filled into an individual capsule was determined based on the highest unit dose available for a commercialized drug product. By way of example, the highest dose commercialized drug product containing the active pharmaceutical ingredient phentermine hydrochloride contains 37.5 mg of the active ingredient as its hydrochloride. The following table summarizes the amount of each active ingredient loaded into a capsule. The amounts of the active ingredient for the pamoates, xinafoate and salicylate salts have been adjusted for their higher molecular weight contribution and for the actual stoichiometry within the salt. For instance, the pamoates herein exist as a 2:1 complex of amine-containing active ingredient to pamoate moiety.

| Drug Salt | MW g/mol | Weight (mg) | (Active as Free Base) (mg) |
|---|---|---|---|
| Drug Hydrochloride | | | |
| Ephedrine Hydrochloride | 201.69 | 47.6 | 39.4 |
| Pseudoephedrine Hydrochloride | 201.69 | 60.6 | 49.6 |
| Phentermine Hydrochloride | 185.70 | 37.5 | 30.1 |
| Benzphetamine Hydrochloride | 275.86 | 50.3 | 40.3 |
| Imipramine Hydrochloride | 316.88 | 150.7 | 133.1 |
| Drug Salt (Pamoate, Xinafoate, Salicylate)* | | | |
| Ephedrine Pamoate | 717.98 | 85.4 | 39.2 |
| Pseudoephedrine Pamoate | 717.98 | 107.0 | 49.2 |
| Phentermine Pamoate | 658.80 | 66.5 | 30.8 |
| Benzphetamine Pamoate | 866.32 | 78.5 | 43.3 |
| Imipramine Xinafoate | 468.16 | 221.0 | 132.1 |
| Imipramine Salicylate | 419.30 | 198.0 | 132.2 |
| Imipramine Pamoate | 949.18 | 225.0 | 132.7 |

*All Pamoate Salts are 2:1, Xinafoate Salt is 1:1, Salicylate Salt is 1:1, and Hydrochloride Salts are 1:1

Prior to use, the 0.1N HCl solution was warmed to 38-42° C. with adequate stirring and then degassed for 30 minutes with helium passed through a sparge stone attached to Tygon tubing. The degassed buffered solution was dispensed into each of five dissolution vessels (900 mL/vessel) using a volumetric flask. The vessels were immersed in the constant temperature bath and allowed to reach thermal equilibrium (37±1° C.). A single capsule (with wire weighting) and containing a specified drug salt was then added to each vessel, the paddles and spindles lowered into the solution and agitation initiated at 50 RPM. The covers with sampling ports were then placed on each vessel. Sampling was performed at regular time intervals on each vessel using a sampling syringe dedicated to each vessel. At each sampling time point about 10 mL of solution was removed from the vessel and filled into a test vial for HPLC analysis.

Example 10

Dissolution Monitoring by HPLC

Drug dissolution assays at specified time intervals were determined by a high pressure liquid chromatography (HPLC) method employing a Waters Atlantis column (dC18, 5 micron, 4.6×150 mm), or equivalent. The HPLC system was a Waters 2695 HPLC system equipped with a Waters 2996 photo diode array detector (detection wavelength: 265 nm extracted; 215 nm extracted). The eluant consisted of mobile phase A (0.1% TFA in water) and mobile phase B (acetonitrile). The gradient elution conditions were as tabulated below.

| Gradient Elution Table | | | |
|---|---|---|---|
| | Time min | % A | % B |
| 1 | | 80 | 20 |
| 2 | 6.00 | 80 | 20 |
| 3 | 10.00 | 52 | 48 |
| 4 | 25.00 | 52 | 48 |
| 5 | 25.10 | 80 | 20 |
| 6 | 33.00 | 80 | 20 |

The drug hydrochlorides were employed as reference comparisons for the dissolution of the corresponding organic acid addition salt of the drug. Reference standards are available from the United States Pharmacopeia; imipramine hydrochloride employed as reference standard was used "as is" and was available from Sigma-Aldrich Catalog #10899. Proceeding, 30-45 mg of the drug hydrochloride reference standard was accurately weighed into a 100 mL volumetric flask and diluted to volume with a previously prepared sample diluent consisting of a filtered 8:2 water:acetonitrile solution. Samples of the dissolution trial solutions were obtained at timed intervals and diluted prior to analysis to obtain targeted concentrations of approximately 45 micro grams/mL-75 micro grams/mL of active pharmaceutical ingredient (API). The prepared samples were then filtered through a 0.45 micron filter directly into an HPLC vial, labeled and loaded for injection into the HPLC system.

HPLC data collection was performed and concentrations determined for each dissolution time interval for each drug substance tested. Concentration assays were determined as a weight/weight percent based on the assay obtained from the reference standard. The data was plotted as a function of percent unit dose released versus the sampling interval time (FIGS. 19 through 25) wherein the percent unit dose released corresponds to a mass assay of the active species found by HPLC analysis of each dissolution time point divided by the available mass initially delivered to the test solution in the capsule. Pairs of data sets were plotted to assess the behavior of the hydrochloride salts versus the organic acid addition salts of the present invention under simulated gastric conditions. Similarly, the dissolution data from HPLC analyses was plotted along with the mass recovery data for each amine salt obtained at pH 4.5 and 7.0 (Example 6). Here also, data set pairs were plotted to assess the behavior of the hydrochloride salts versus the associated organic acid addition salts over a pH range encompassing gastric and mucosal conditions (FIGS. 26-32).

Example 11

Solubility Evaluation of the Pseudoephedrine Pamoate

The solubility of pseudoephedrine pamoate was evaluated in each of isopropanol, acetone and toluene. About 0.5 grams of the salt was added to approximately 5.0 grams of each solvent. The samples were stirred at room temperature for about 15 minutes, filtered and dried to determine a mass percent recovery of the salt. The filtrates appeared clear and without color with the exception of the acetone filtrate exhibiting some color. The mass recoveries for the salt from each solvent were: 97% (isopropanol); 92% (acetone); 99% (toluene). Similar results were obtained for the solubility evaluation of ephedrine pamoate.

Example 12

Dissolving Metal Reduction of Pseudoephedrine

Anhydrous ammonia (50 mL) was condensed into a dry ice cooled multi-neck round bottom flask. Anhydrous tetrahydrofuran (20 mL) was added and then lithium metal (0.103 g, 3 equivalents based on pseudoephedrine charge) was added portion wise with stirring and stirring continued until all the metal had dissolved. Pseudoephedrine free base (0.82 g) was added as a solution in 20 mL of anhydrous tetrahydrofuran over a period of about 10 minutes. After stirring for 10 additional minutes, the reaction mixture was quenched by adding 1.5 grams of solid ammonium chloride. The cooling was removed and the mixture allowed to warm to room temperature. The residue was diluted with about 30 mL of brine and about 30 mL of diethyl ether. The phases were separated and the aqueous phase was washed with two additional 30 mL aliquots of diethyl ether. The combined organic extracts were dried over anhydrous sodium sulfate and concentrated to 0.7 grams of colorless oil, which was re-dissolved in 125 mL of fresh ether and treated with gaseous HCl. The white solid which formed was filtered and dried. The weight yield was 0.8 grams (87%) of methamphetamine hydrochloride. The material was characterized by FTIR (FIG. 33) and DSC (FIG. 34).

Example 13

Dissolving Metal Reduction of Pseudoephedrine Pamoate (6 Equivalents of Lithium)

Anhydrous ammonia (30 mL) was condensed into a dry ice cooled multi-neck round bottom flask. Anhydrous tetrahydrofuran (20 mL) was added and then lithium metal (0.030 g, 6 equivalents) was added portion wise with stirring and stirring continued until all the metal had dissolved. Pseudoephedrine pamoate (0.5 g) was added as a solid in small aliquots over a period of about 10 minutes. After stirring for 10 additional minutes, the reaction mixture was quenched by adding 1.5 grams of solid ammonium chloride. The cooling was removed and the mixture allowed to warm to room temperature. The residue was diluted with about 30 mL of brine and about 30 mL of diethyl ether. The phases were separated and the aqueous phase was washed with two additional 30 mL aliquots of diethyl ether. The combined organic extracts were dried over anhydrous sodium sulfate and concentrated to a yellow residue which was re-dissolved in 125 mL of fresh ether and treated with gaseous HCl. The pale yellow solid which formed was filtered and dried. The weight yield was 0.2 grams. The material was characterized by HPLC (FIG. 35) and DSC (FIG. 36). HPLC indicated the solid to be 90% pseudoephedrine pamoate and 10% methamphetamine.

Example 14

Dissolving Metal Reduction of Pseudoephedrine Pamoate (15 Equivalents of Lithium)

Anhydrous ammonia (30 mL) was condensed into a dry ice cooled multi-neck round bottom flask. Anhydrous tetrahydrofuran (20 mL) was added and then lithium metal (0.072 g, 15 equivalents) was added portion wise with stirring and stirring continued until all the metal had dissolved. Pseudoephedrine pamoate (0.5 g) was added as a solid in small aliquots over a period of about 10 minutes. After stirring for about 30 additional minutes, the reaction mixture was quenched by adding 1.5 grams of solid ammonium chloride. The cooling was removed and the mixture and allowed to warm to room temperature. The residue was diluted with about 30 mL of brine and about 30 mL of diethyl ether. The phases were separated and the aqueous phase was washed with two additional 30 mL aliquots of diethyl ether. The combined organic extracts were dried over anhydrous sodium sulfate and concentrated to a yellow residue which was re-dissolved in 75 mL of dry ether and treated with gaseous HCl. The pale yellow solid which formed was filtered and dried. The weight yield was 0.2 grams. The material was characterized by HPLC (FIG. 37) and DSC (FIG. 38). HPLC indicated the solid to be principally methamphetamine contaminated with a small amount of pseudoephedrine and artifacts from the Birch reduction of pamoic acid.

Example 15

Dissolving Metal Reduction of Pamoic Acid

Anhydrous ammonia (50 mL) was condensed into a dry ice cooled multi-neck round bottom flask. Anhydrous tetrahydrofuran (20 mL) was added and then lithium metal (0.267 g, 15 equivalents) was added portion wise with stirring and stirring continued until all the metal had dissolved. Pamoic acid (1.0 g) was added as a solid in small aliquots over a period of about 2-3 minutes. After stirring for 10 additional minutes, the reaction mixture was quenched by adding 3.0 grams of solid ammonium chloride. The cooling was removed and the mixture allowed to warm to room temperature. The alkaline residue was diluted with about 30 mL of brine and about 30 mL of diethyl ether. Concentration of the ether extract resulted in almost no organic residues from the extraction of the alkaline mixture. The aqueous solution was acidified to about pH 2.0 resulting in a yellow precipitate which was largely soluble in diethyl ether. The solid precipitate was titrated with diethyl ether, filtered to remove a small amount of insoluble material and the ether extracts were concentrated resulting in a bright yellow-orange solid which was a mixture of several compounds by TLC. The weight yield was 0.41 grams. The material was analyzed by HPLC (FIG. 39).

Example 16

Hydriodic Acid/Red Phosphorous Reduction of Pseudoephedrine Hydrochloride

Pseudoephedrine hydrochloride (2.0 grams), 47% hydriodic acid (10 mL), and red phosphorus (1.0 grams) was charged to a 100 mL round bottom flask with stirring. The mixture was heated at reflux for about 18 hours and then cooled. The reaction mixture was diluted with about 20 mL water and the excess phosphorus was removed by filtration. The filter cake was washed with fresh water and the combined filtrate was made basic (pH 12) by addition of 20% sodium hydroxide solution. The basic solution was extracted with 3×40 mL diethyl ether and the combined extracts were treated with hydrogen chloride gas which resulted in the separation of a white crystalline solid. The dry solid weighed 1.5 grams and represents an 81% yield of methamphetamine. The material was characterized by DSC (FIG. 40), FTIR (FIG. 41), and HPLC (FIG. 42).

Example 17

Hydriodic Acid/Red Phosphorous Reduction of Pseudoephedrine Pamoate

Pseudoephedrine pamoate (3.2 grams), 47% hydriodic acid (10 mL), and red phosphorus (1.1 grams) was charged to a 100 mL round bottom flask with stirring. The mixture was heated at reflux for about 18 hours and then cooled. The reaction mixture was diluted with about 25 mL water and the solids were removed by filtration. The filter cake was washed with a fresh aliquot of water and the combined filtrate was made basic (pH 12) by addition of 20% sodium hydroxide solution. The basic solution was extracted with 3×40 mL diethyl ether and the combined extracts were treated with hydrogen chloride gas which resulted in the separation of a bright yellow oily phase. The ether mixture was concentrated to a residue on the rotary evaporator and the residues were re-dissolved in ethanol and re-concentrated to remove any moisture or other volatiles. The ethanol treatment was repeated a second time and the residues were re-slurried in fresh ether. The solid product which resulted was collected on a filter and washed with ether to remove most of the yellow color. The dry solid weighed 1.2 grams and represents a 77.4% yield of methamphetamine. The material was characterized by HPLC (FIG. 43).

Example 18

Dissolving Metal Reduction of Dibenzylidene Sorbitol

Anhydrous ammonia (40 mL) was condensed into a dry ice cooled multi-neck round bottom flask. Anhydrous tetrahydrofuran (20 mL) was added and then lithium metal (0.387 g, 10 equivalents) was added portion wise with stirring and stirring continued until all the metal had dissolved. Dibenzylidene sorbitol (2.0 g) was added as a solid in small aliquots over a period of about 10 minutes. After stirring for 10 additional minutes, the reaction mixture was quenched by adding 2.0 grams of solid ammonium chloride. The cooling was removed and the mixture allowed to warm to room temperature. The residue was diluted with about 30 mL of brine and about 100 mL of methyl tert-butyl ether. The phases were separated and the aqueous phase was washed with two additional 100 mL aliquots methyl tert-butyl ether. The combined organic extracts were back washed with 50 mL of brine. Analysis of the extracts by GC showed the presence of toluene, which would be expected if the acetal moiety of dibenzylidene sorbitol reduced under the reaction conditions. Concentration of the extracts resulted in a small residue weighing only 0.3 grams. Sorbitol itself would be water soluble and not extracted into the ether solvent.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An oral dosage drug product comprising a pharmaceutically active compound and an alditol acetal wherein said pharmaceutically active compound and said alditol acetal are in a dried solid form and said oral dosage drug product is in a solid form for oral administration wherein said pharmaceutically active compound is an amine-containing pharmaceutically active compound selected from the group consisting of acetorphine, acetylmethadol, allylprodine, alphacetylmethadol, bufotenine, dextromoramide, diethyltryptamine, etorphine, heroin, ibogaine, ketobemidone, lysergic acid diethylamide, mescaline, methaqualone, 3,4-methylenedioxyamphetamine, 3,4-methylenedioxymethamphetamine, N-ethyl-1-phenylcyclohexylamine, peyote, 1-(1-phenylcyclohexyl)pyrrolidine, psilocybin, psilocin, 1-{1-(2-thienyl)-cyclohexyl}-piperidine, alphaprodine, anileridine, cocaine, dextropropoxyphene, diphenoxylate, ethylmorphine, glutethimide, hydrocodone, hydromorphone, levoalphaaceytlmethadol, levorphanol, meperidine, methadone, morphine, opium, oxycodone, oxymorphone, poppy straw, thebaine, amphetamine, methamphetamine, methylphenidate, phencyclidine, codeine, benzphetamine, ketamine, alprazolam, chlorodiazepoxide, clorazepate, diethylpropion, fenfluramine, flurazepam, halazepam, lorazepam, mazindol, mebutamate, midazolam, oxazepam, pemoline, pentazocine, phentermine, prazepam, quazepam, temazepam, triazolam, zolpidem, and buprenorphine.

2. The oral dosage drug product of claim 1 comprising an organic acid salt of said amine-containing pharmaceutically active compound.

3. The oral dosage drug product of claim 2 wherein said organic acid addition salt of an amine-containing pharmaceutically active compound is selected from the group consisting of pseudoephedrine pamoate, ephedrine pamoate, pseudoephedrine xinafoate and ephedrine xinafoate.

4. The oral dosage drug product of claim 2 wherein said organic acid addition salt is defined by Structure A

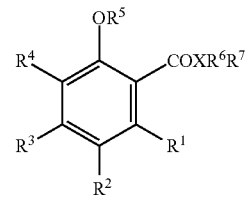

Structure A wherein $R^1$-$R^4$ are independently selected from H, alkyl of 1-6 carbons, adjacent groups may be taken together to form a cyclic alkyl, cyclic alkyl-aryl, or cyclic aryl moiety;

$R^5$ is selected from H, or an alkali earth cation;

$R^6$ and $R^7$ are independently selected from H, alkyl of 1-6 carbons, an alkali earth cation, and aryl of 6 to 12 carbons, in a number sufficient to complete the valence bonding of X, and wherein X is selected from nitrogen, oxygen or sulfur.

5. The oral dosage drug product of claim 4 wherein said organic acid addition salt is selected from the group consisting of:

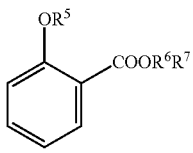

Structure B wherein $R^5$, $R^6$ and $R^7$ remain as defined for Structure A;

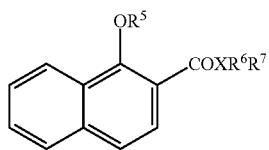

Structure C wherein X, $R^5$, $R^6$ and $R^7$ remain as defined above for Structure A;

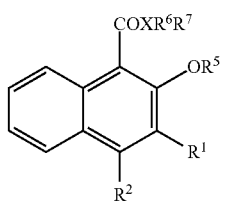

Structure D wherein X, $R^1$, $R^2$, $R^5$, $R^6$ and $R^7$ remain as defined above for Structure A;

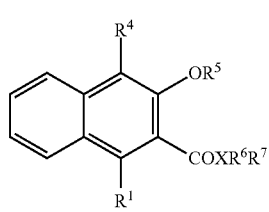

Structure E wherein X, $R^1$, $R^4$, $R^5$, $R^6$ and $R^7$ remain as defined above for Structure A;

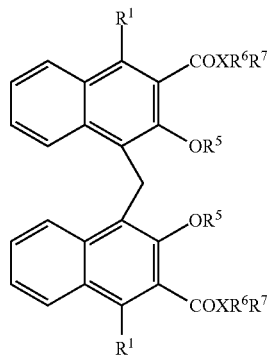

Structure F wherein X, $R^1$, $R^5$, $R^6$ and $R^7$ are independently defined as above for Structure A; and

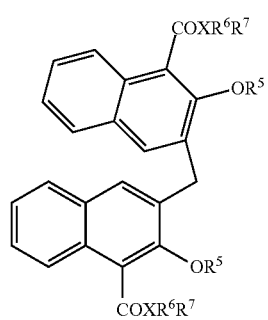

Structure G wherein X, $R^5$, $R^6$ and $R^7$ are independently defined as above for Structure A.

6. The oral dosage drug product of claim 5 wherein for Structure D, X is O; $R^1$ and $R^2$ are hydrogen.

7. The oral dosage drug product of claim 5 wherein for Structure E, X is O, $R^1$ and $R^4$ are hydrogen.

8. The oral dosage drug product of claim 5 wherein for Structure F, at least one X is O and at least one $R^1$ is hydrogen.

9. The oral dosage drug product of claim 5 wherein for Structure G, X is O and $R^5$ is hydrogen.

10. The oral dosage drug product of claim 5 wherein said organic acid addition salt comprises a material selected from the group consisting of pamoic acid, disodium pamoate, di-ammonium pamoate, di-potassium pamoate, lower molecular weight di-alkyl amine pamoate, lower molecular weight di-aryl amine pamoate, lower molecular weight di-alkyl esters of pamoic acid, lower molecular weight di-aryl esters of pamoic acid, lower molecular weight di-alkylacyl O-esters of pamoic acid and lower molecular weight di-arylacyl O-esters of pamoic acid.

11. The oral dosage drug product of claim 5 wherein the organic acid addition salt comprises a material selected from the group consisting of BON acid, ortho isomers of hydroxy naphthoic acid, sodium hydroxy naphthoic acid, ammonium hydroxy naphthoate, potassium hydroxy naphthoate, lower molecular weight alkyl amine salts of hydroxy naphthoic acid, lower molecular weight aryl amine salts of hydroxy naphthoic acid, lower molecular weight alkyl esters of hydroxy naphthoic acid, lower molecular weight aryl esters of hydroxy naphthoic acid, lower molecular weight alkylacyl O-esters of hydroxyl naphthoic acid and lower molecular weight arylacyl O-esters of hydroxyl naphthoic acid.

12. The oral dosage drug product of claim 5 wherein the organic acid addition salt is selected from the group consisting of salicylic acid, sodium salicylate, ammonium salicylate, potassium salicylate, lower molecular weight alkyl amine salts of salicylic acid, lower molecular weight aryl amine salts of salicylic acid, lower molecular weight alkyl esters of salicylic acid, lower molecular weight aryl esters of salicylic acid, lower molecular weight alkylacyl O-esters of salicylic acid and lower molecular weight arylacyl O-esters of salicylic acid.

13. The oral dosage drug product of claim 5 wherein said organic acid addition salt comprises an acid selected from pamoic acid or a synthetic equivalent thereof; salicylic acid or a synthetic equivalent thereof and hydroxy naphthoic acid or a synthetic equivalent thereof.

14. The oral dosage drug product of claim 1 wherein said pharmaceutically active compound comprises an active ingredient selected from pseudoephedrine and ephedrine.

15. The oral dosage drug product of claim 1 further comprising an additive.

16. The oral dosage drug product of claim 15 wherein said additive is selected from the group consisting of binder, colorant, flow agent, disintegrants, release agent, surfactant, buffer, wetting agent and particle coating.

17. The oral dosage drug product of claim 15 wherein said additive is an aromatic organic acid.

18. The oral dosage drug product of claim 17 wherein said aromatic organic acid is defined by Structure H:

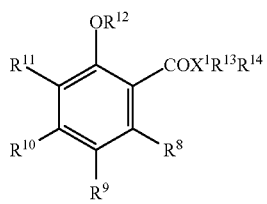

Structure H wherein $R^8$-$R^{11}$ are independently selected from H, alkyl or substituted alkyl of 1-6 carbons, adjacent groups may be taken together to form a cyclic alkyl, cyclic alkyl-aryl, or cyclic aryl moiety;
$R^{12}$ is selected from H, or an alkali earth cation;
$R^{13}$ and $R^{14}$ are independently selected from H, alkyl of 1-6 carbons, an alkali earth cation, and aryl of 6 to 12 carbons, in a number sufficient to complete the valence bonding of $X^1$; and
wherein $X^1$ is selected from nitrogen, oxygen or sulfur.

19. The oral dosage drug product of claim 18 wherein at least one of $R^{12}$ and $R^{13}$ is an alkali earth cation.

20. The oral dosage drug product of claim 18 wherein said additive is selected from the group consisting of pamoic acid, an alkali earth salt of pamoate, BON acid and an alkali earth salt of BON acid.

21. The oral dosage drug product of claim 18 wherein said additive and said opioid are present in a molar ratio of at least 0.5:1.

22. The oral dosage drug product of claim 20 wherein said additive and said opioid are present in a molar ratio of between 0.5:1 and 1:1.

23. The oral dosage drug product of claim 21 wherein said additive and said opioid are present in a molar ratio of at least 2:1.

24. The oral dosage drug product of claim 21 wherein said additive and said opioid are present in a molar ratio of no more than 3:1.

25. The oral dosage drug product of claim 1 wherein said alditol acetal is defined by the formula:

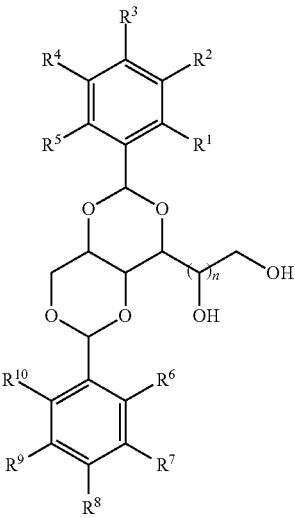

wherein $R^1$-$R^{10}$ are each independently selected from hydrogen, lower alkyl groups containing 1-18 carbon atoms, hydroxy, methoxy, mono- or dialkylamino, nitro and halogen or together form a heterocyclic ring containing up to 5 carbon atoms and n may be 0, 1 or 2.

26. The oral dosage drug product of claim 1 wherein said alditol acetal is selected from the group consisting of 1,3:2,4-dibenzylidene sorbitol; 1,3:2,4-bis(p-methylbenzylidene) sorbitol; 1,3:2,4-bis(p-chlorobenzylidene)sorbitol; 1,3:2,4-bis(2,4-dimethyldibenzylidene)sorbitol; 1,3:2,4-bis(p-ethylbenzylidene)sorbitol; 1,3:2,4-bis(3,4-dimethyldibenzylidene)sorbitol; 1,3:2,4-bis(3,4-diethylbenzylidene) sorbitol; 1,3;2,4-bis(3-ethyl4-methylbenzylidene)sorbitol; 1,3:2,4-bis(4-chloro-3-methylbenzylidene)sorbitol; 1,3:2,4-bis(3-chloro-4-methylbenzylidene)sorbitol; 1,3:2,4-bis(3-bromo-4-isopropylbenzylidene)sorbitol; 1,3:2,4-bis(3-bromo-4-methylbenzylidene)sorbitol; and 1,3:2,4-bis(3-bromo-4-ethylbenzylidene)sorbitol; 2,4-mono(3,4-dimethylbenzylidene)sorbitol; 2,4-mono(4-fluoro-3-methylbenzylidene)sorbitol; 1,3-O-(3,4-dichlorobenzylidene):2,4-O-(3,4-dimethylbenzylidene) sorbitol; 1,3-O-(3,4-difluorobenzylidene):2,4-O-(3,4-dimethylbenzylidene)sorbitol; 1,3-O-(3,4-dichlorobenzylidene):2,4-O-(3,4-dimethoxybenzylidene) sorbitol; 1,3-O-(3,4-dichlorobenzylidene):2,4-O-(5-indanylidene)sorbitol; 1,3-O-(4-nitrobenzylidene):2,4-O-(3,4dimethylbenzylidene)sorbitol; 1,3-O-(4-nitrobenzylidene): 2,4-O-(3,4-methylenedioxybenzylidene)sorbitol; 1,3-O-(4-fluoro-3-methylbenzylidene): 2,4-O-(3,4-dimethylbenzylidene)sorbitol; 1,3-O-(3,4-dimethylbenzylidene): 2,4-O-(4-fluoro-3-methylbenzylidene)sorbitol; 1,3-O-(4-fluoro-3-methylbenzylidene): 2,4-O-(3-fluoro-4-methylbenzylidene) sorbitol; 1,3-O-(3-fluoro-4-methylbenzylidene): 2,4-O-(4-fluoro-3-methylbenzylidene)sorbitol; 1,3-O-(4-fluoro-3-methylbenzylidene):2,4-O-(4-chlorobenzylidene)sorbitol; 1,3-O-(4-chlorobenzylidene):2,4-O-(4-fluoro-3-methylbenzylidene)sorbitol; 1,3-O-(4-chloro-3-methylbenzylidene): 2,4-O-(3-chloro-4-methylbenzylidene)sorbitol; 1,3-O-(3-chloro-4-methylbenzylidene): 2,4-O-(4-chloro-3-methylbenzylidene)sorbitol; 1,3-O-(4-fluoro-3-methylbenzylidene): 2,4-O-(5',6',7',8tetrahydro-2-napthylidene) sorbitol; 1,3-O-(5',6',7',8'-tetrahydronapthylidene): 2,4-O-fluoro-3-methylbenzylidene)sorbitol; 1,3-O-(4-Chloro-3-methylbenzylidene)-2,4-O-(5',6', 7',8'-tetrahydro-2-napthylidene)sorbitol; 1,3-O-(5',6',7',8'-tetrahydronapthylidene): 2,4-O-(4-chloro-3- methylbenzylidene)sorbitol; 1,3-O-(3-bromo-4-ethylbenzylidene): 2,4-O-(3,4-dimethylbenzylidene)sorbitol; 1,3-O-(3-bromo-4-isopropylbenzylidene): 2,4-O-(3,4-dimethylbenzylidene)sorbitol; 1,3-O-(3-bromo-4-methylbenzylidene): 2,4-O-(3,4-dimethylbenzylidene) sorbitol; 1,3-O-(4-chlorobenzylidene): 2,4-O-(3-bromo-4-isopropylbenzylidene)sorbitol; 1,3-O-(4-t-butylbenzylidene):2,4-O-(3,4-dimethylbenzylidene) sorbitol; 1,3-O-(3,4-dimethylbenzylidene):2,4-O-(t-butylbenzylidene)sorbitol; 1,3-O-(3,4-dimethoxybenzylidene):2,4-O-(3,4-dimethylbenzylidene) sorbitol; 1,3-O-(3,4-dimethylbenzylidene):2,4-O-(3,4-dimethoxybenzylidene)sorbitol; 1,3-O-(3,4-methylenedioxybenzylidene): 2,4-O-(3,4-dimethylbenzylidene)sorbitol; 1,3-O-(3,4-dimethylbenzylidene): 2,4-O-(3,4-methylenedioxybenzylidene)sorbitol; 1,3-O-(4-isopropylbenzylidene):2,4-O-(3,4-dimethylbenzylidene) sorbitol; 1,3-O-(3,4-dimethylbenzylidene):2,4-O-(4-isopropylbenzylidene)sorbitol; 1,3-O-(3,4-dimethylbenzylidene):2,4-O-(2-naphthylbenzylidene) sorbitol; 1,3-O-(2-naphthylbenzylidene):2,4-O-(3,4-dimethylbenzylidene)sorbitol; 1,3:2,4-bis(4-ethylbenzylidene)-1-allyl-sorbitol, 1,3,2,4-bis)3'methyl-4'fluorobenzylidene)-1-propyl-sorbitol, 1,3,2,4-bis(5'6'7'8'-tetrahydro-2-naphthaldehydebenzylidene)-1-allyl-xylitol, bis-1,3,2,4-(3'4'-dimethylbenzylbenzylidene-1"-methyl-2"-propyl-sorbitol and 1,3,2,4-bis(3',4'-dimethylbenzylidene-1-proplyl-xylitol.

27. The oral dosage drug product of claim 26 wherein said pharmaceutically active compound comprises an active ingredient selected from the group consisting of pseudoephedrine and ephedrine.

28. The oral dosage drug product of claim 27 wherein said pharmaceutically active compound is selected from the group consisting of pseudoephedrine pamoate, ephedrine pamoate, pseudoephedrine xinafoate and ephedrine xinafoate.

29. The oral dosage drug product of claim 28 wherein said alditol acetal is 1,3:2,4-dibenzylidene sorbitol.

30. A drug product comprising:
a drug substance consisting of an organic acid addition salt of an active pharmaceutical wherein said active pharmaceutical is selected from the group consisting of pseudoephedrine and ephedrine and said organic acid addition salt is defined by Structure A Structure A wherein $R^1$-$R^4$ are independently selected from H, alkyl of 1-6 carbons, adjacent groups may be taken together to form a cyclic alkyl, cyclic alkyl-aryl, or cyclic aryl moiety;
$R^5$ is selected from H, or an alkali earth cation;
$R^6$ and $R^7$ are independently selected from H, alkyl of 1-6 carbons, an alkali earth cation, and aryl of 6 to 12 carbons, in a number sufficient to complete the valence bonding of X, and
wherein X is selected from nitrogen, oxygen or sulfur;
an additive selected from the group consisting of alditol acetal and an organic acid defined by Structure H:

Structure H wherein $R^8$-$R^{11}$ are independently selected from H, alkyl or substituted alkyl of 1-6 carbons, adjacent groups may be taken together to form a cyclic alkyl, cyclic alkyl-aryl, or cyclic aryl moiety;
$R^{12}$ is selected from H, or an alkali earth cation;
$R^{13}$ and $R^{14}$ are independently selected from H, alkyl of 1-6 carbons, an alkali earth cation, and aryl of 6 to 12 carbons, in a number sufficient to complete the valence bonding of $X^1$; and
wherein $X^1$ is selected from nitrogen, oxygen or sulfur;
wherein said drug substance and said additive are taken together in a dried solid form; and
wherein said drug product is in a solid dose form for oral administration.

31. The drug product of claim 30 wherein at least one of $R^{12}$ and $R^{13}$ is an alkali earth cation.

32. The drug product of claim 30 wherein said additive is selected from the group consisting of pamoic acid, an alkali earth salt of pamoate, BON acid and an alkali earth salt of BON acid.

33. The drug product of claim 30 wherein said additive and said active pharmaceuticals are present in a molar ratio of between 0.5:1 and 1:1.

34. The drug product of claim 30 wherein said alditol acetal is defined by the formula:

wherein $R^1$-$R^{10}$ are each independently selected from hydrogen, lower alkyl groups containing 1-18 carbon atoms, hydroxy, methoxy, mono- or dialkylamino, nitro and halogen or together form a heterocyclic ring containing up to 5 carbon atoms and n may be 0, 1 or 2.

35. The drug product of claim 30 wherein said alditol acetal is selected from the group consisting of 1,3:2,4-dibenzylidene sorbitol; 1,3:2,4-bis(p-methylbenzylidene) sorbitol; 1,3:2,4-bis(p-chlorobenzylidene)sorbitol; 1,3:2,4- bis(2,4-dimethyldibenzylidene)sorbitol; 1,3:2,4-bis(p-ethylbenzylidene)sorbitol; 1,3:2,4-bis(3,4-dimethyldibenzylidene)sorbitol; 1,3:2,4-bis(3,4-diethylbenzylidene)sorbitol; 1,3;2,4-bis(3-ethyl4-methylbenzylidene)sorbitol; 1,3:2,4-bis(4-chloro-3-methylbenzylidene)sorbitol; 1,3:2,4-bis(3-chloro-4-methylbenzylidene)sorbitol; 1,3:2,4-bis(3-bromo-4-isopropylbenzylidene)sorbitol; 1,3:2,4-bis(3-bromo-4-methylbenzylidene)sorbitol; and 1,3:2,4-bis(3-bromo-4-ethylbenzylidene)sorbitol; 2,4-mono(3,4-dimethylbenzylidene)sorbitol; 2,4-mono(4-fluoro-3-methylbenzylidene)sorbitol; 1,3-O-(3,4-dichlorobenzylidene):2,4-O-(3,4-dimethylbenzylidene)sorbitol; 1,3-O-(3,4-difluorobenzylidene):2,4-O-(3,4-dimethylbenzylidene)sorbitol; 1,3-O-(3,4-dichlorobenzylidene):2,4-O-(3,4-dimethoxybenzylidene)sorbitol; 1,3-O-(3,4-dichlorobenzylidene):2,4-O-(5-indanylidene)sorbitol; 1,3-O-(4-nitrobenzylidene):2,4-O-(3,4dimethylbenzylidene)sorbitol; 1,3-O-(4-nitrobenzylidene): 2,4-O-(3,4-methylenedioxybenzylidene)sorbitol; 1,3-O-(4-fluoro-3-methylbenzylidene): 2,4-O-(3,4-dimethylbenzylidene)sorbitol; 1,3-O-(3,4-dimethylbenzylidene): 2,4-O-(4-fluoro-3-methylbenzylidene)sorbitol; 1,3-O-(4-fluoro-3-methylbenzylidene): 2,4-O-(3-fluoro-4-methylbenzylidene)sorbitol; 1,3-O-(3-fluoro-4-methylbenzylidene): 2,4-O-(4-fluoro-3-methylbenzylidene)sorbitol; 1,3-O-(4-fluoro-3-methylbenzylidene):2,4-O-(4-chlorobenzylidene)sorbitol; 1,3-O-(4-chlorobenzylidene):2,4-O-(4-fluoro-3-methylbenzylidene)sorbitol; 1,3-O-(4-chloro-3-methylbenzylidene): 2,4-O-(3-chloro-4-methylbenzylidene)sorbitol; 1,3-O-(3-chloro-4-methylbenzylidene): 2,4-O-(4-chloro-3-methylbenzylidene)sorbitol; 1,3-O-(4-fluoro-3-methylbenzylidene): 2,4-O-(5',6',7',8tetrahydro-2-napthylidene)sorbitol; 1,3-O-(5',6',7',8'-tetrahydronapthylidene): 2,4-O-fluoro-3-methylbenzylidene)sorbitol; 1,3-O-(4-Chloro-3-methylbenzylidene)-2,4-O-(5',6', 7',8'-tetrahydro-2-napthylidene)sorbitol; 1,3-O-(5',6',7',8'-tetrahydronapthylidene): 2,4-O-(4-chloro-3-methylbenzylidene)sorbitol; 1,3-O-(3-bromo-4-ethylbenzylidene): 2,4-O-(3,4-dimethylbenzylidene)sorbitol; 1,3-O-(3-bromo-4-isopropylbenzylidene): 2,4-O-(3,4-dimethylbenzylidene)sorbitol; 1,3-O-(3-bromo-4-methylbenzylidene): 2,4-O-(3,4-dimethylbenzylidene)sorbitol; 1,3-O-(4-chlorobenzylidene): 2,4-O-(3-bromo-4-isopropylbenzylidene)sorbitol; 1,3-O-(4-t-butylbenzylidene):2,4-O-(3,4-dimethylbenzylidene)sorbitol; 1,3-O-(3,4-dimethylbenzylidene):2,4-O-(t-butylbenzylidene)sorbitol; 1,3-O-(3,4-dimethoxybenzylidene):2,4-O-(3,4-dimethylbenzylidene)sorbitol; 1,3-O-(3,4-dimethylbenzylidene):2,4-O-(3,4-dimethoxybenzylidene)sorbitol; 1,3-O-(3,4-methylenedioxybenzylidene): 2,4-O-(3,4-dimethylbenzylidene)sorbitol; 1,3-O-(3,4-dimethylbenzylidene): 2,4-O-(3,4-methylenedioxybenzylidene)sorbitol; 1,3-O-(4-isopropylbenzylidene):2,4-O-(3,4-dimethylbenzylidene)sorbitol; 1,3-O-(3,4-dimethylbenzylidene):2,4-O-(4-isopropylbenzylidene)sorbitol; 1,3-O-(3,4-dimethylbenzylidene):2,4-O-(2-naphthylbenzylidene)sorbitol; 1,3-O-(2-naphthylbenzylidene):2,4-O-(3,4-dimethylbenzylidene)sorbitol; 1,3,2,4-bis(4-ethylbenzylidene)-1-allyl-sorbitol, 1,3,2,4-bis)3'methyl-4'fluorobenzylidene)-1-propyl-sorbitol, 1,3,2,4-bis(5'6'7'8'-tetrahydro-2-naphthaldehydebenzylidene)-1-allyl-xylitol, bis-1,3,2,4-(3'4'-dimethylbenzylbenzylidene-1"-methyl-2"-propyl-sorbitol and 1,3,2,4-bis(3',4'-dimethylbenzylidene-1-proplyl-xylitol.

36. The drug product of claim 35 wherein said drug substance is selected from the group consisting of pseudoephedrine pamoate, ephedrine pamoate, pseudoephedrine xinafoate and ephedrine xinafoate.

37. The drug product of claim 36 wherein said alditol acetal is 1,3:2,4-dibenzylidene sorbitol.

38. The drug product of claim 30 wherein said organic acid addition salt is selected from the group consisting of:

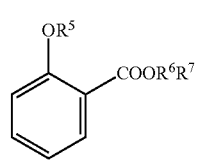

Structure B wherein $R^5$, $R^6$ and $R^7$ remain as defined for Structure A;

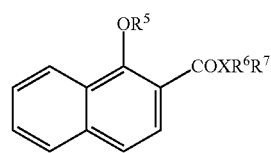

Structure C wherein X, $R^5$, $R^6$ and $R^7$ remain as defined above for Structure A;

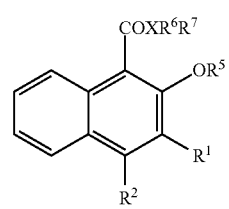

Structure D wherein X, $R^1$, $R^2$, $R^5$, $R^6$ and $R^7$ remain as defined above for Structure A;

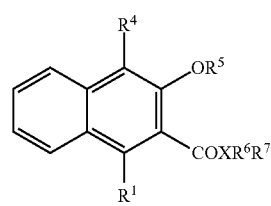

Structure E wherein X, $R^1$, $R^4$, $R^5$, $R^6$ and $R^7$ remain as defined above for Structure A;

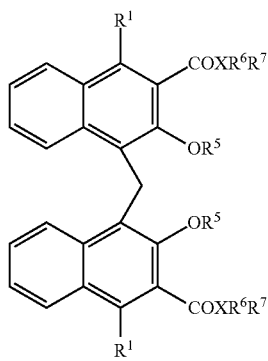

Structure F wherein X, $R^1$, $R^5$, $R^6$ and $R^7$ are independently defined as above for Structure A; and

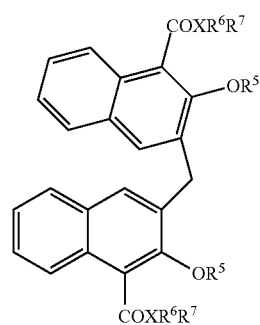

Structure G wherein X, $R^5$, $R^6$ and $R^7$ are independently defined as above for Structure A.

39. The drug product of claim 38 wherein for Structure D X is O; $R^1$ and $R^2$ are hydrogen.

40. The drug product of claim 38 wherein for Structure E X is O, $R^1$ and $R^4$ are hydrogen.

41. The drug substance of claim 38 wherein for Structure F at least one X is O and at least one $R^1$ is hydrogen.

42. The drug product of claim 38 wherein for Structure G X is O and $R^5$ is hydrogen.

43. The drug product of claim 38 wherein said organic acid comprises a material selected from the group consisting of pamoic acid, disodium pamoate, di-ammonium pamoate, di-potassium pamoate, lower molecular weight di-alkyl amine pamoate, lower molecular weight di-aryl amine pamoate, lower molecular weight di-alkyl esters of pamoic acid, lower molecular weight di-aryl esters of pamoic acid, lower molecular weight di-alkylacyl O-esters of pamoic acid and lower molecular weight di-arylacyl O-esters of pamoic acid.

44. The drug product of claim 38 wherein the organic acid comprises a material selected from the group consisting of BON acid, ortho isomers of hydroxy naphthoic acid, sodium hydroxy naphthoic acid, ammonium hydroxy naphthoate, potassium hydroxy naphthoate, lower molecular weight alkyl amine salts of hydroxy naphthoic acid, lower molecular weight aryl amine salts of hydroxy naphthoic acid, lower molecular weight alkyl esters of hydroxy naphthoic acid, lower molecular weight aryl esters of hydroxy naphthoic acid, lower molecular weight alkylacyl O-esters of hydroxyl naphthoic acid and lower molecular weight arylacyl O-esters of hydroxyl naphthoic acid.

45. The drug product of claim 38 wherein the organic acid is selected from the group consisting of salicylic acid, sodium salicylate, ammonium salicylate, potassium salicylate, lower molecular weight alkyl amine salts of salicylic acid, lower molecular weight aryl amine salts of salicylic acid, lower molecular weight alkyl esters of salicylic acid, lower molecular weight aryl esters of salicylic acid, lower molecular weight alkylacyl O-esters of salicylic acid and lower molecular weight arylacyl O-esters of salicylic acid.

46. The drug product of claim 38 wherein said organic acid salt comprises an acid selected from pamoic acid or a synthetic equivalent thereof; salicylic acid or a synthetic equivalent thereof and hydroxy naphthoic acid or a synthetic equivalent thereof.

47. The oral dosage drug product of claim 1 wherein said oral dosage drug product is selected from the group consisting of a pill, a tablet and a capsule containing said dried solid.

48. The drug product of claim 30 wherein said oral dosage drug product is selected from the group consisting of a pill, a tablet and a capsule containing said dried solid.

* * * * *